US012653899B2

(12) United States Patent
Grodzinsky et al.

(10) Patent No.: US 12,653,899 B2
(45) Date of Patent: Jun. 16, 2026

(54) MULTI-TARGETED, TUNABLE, SUSTAINED DELIVERY OF PAYLOADS TO CHARGED AVASCULAR TISSUES

(71) Applicant: Massachusetts Institute of Technology, Cambridge, MA (US)

(72) Inventors: Alan Grodzinsky, Lexington, MA (US); Yamini Krishnan, Telangana (IN)

(73) Assignee: Massachusetts Institute of Technology, Cambridge, MA (US)

( * ) Notice: Subject to any disclaimer, the term of this patent is extended or adjusted under 35 U.S.C. 154(b) by 405 days.

(21) Appl. No.: 16/883,419

(22) Filed: May 26, 2020

(65) Prior Publication Data

US 2021/0023236 A1 Jan. 28, 2021

Related U.S. Application Data

(60) Provisional application No. 62/879,311, filed on Jul. 26, 2019.

(51) Int. Cl.
*A61K 47/64* (2017.01)
*A61K 31/573* (2006.01)
(Continued)

(52) U.S. Cl.
CPC ........ *A61K 47/6455* (2017.08); *A61K 31/573* (2013.01); *A61K 38/2006* (2013.01);
(Continued)

(58) Field of Classification Search
CPC .............. A61K 47/6455; A61K 31/573; A61K 38/2006; A61K 38/30; C07K 14/43595; C07K 2319/60; C07K 14/65; A61P 19/02
See application file for complete search history.

(56) References Cited

U.S. PATENT DOCUMENTS 5,908,626 A * 6/1999 Chang ..................... A61P 31/12 424/134.1
2014/0193508 A1* 7/2014 Bajpayee ............. A61K 47/551 424/501
2015/0030593 A1* 1/2015 Bowdish .......... A61K 39/39558 435/254.2

FOREIGN PATENT DOCUMENTS

WO WO 2009/134808 A2 11/2009
WO WO 2017/155945 A1 9/2017

OTHER PUBLICATIONS

Bajpayee et al, Cartilage-targeting drug delivery: can electrostatic interactions help?, Nature Reviews | Rheumatology, 2017, 13, pp. 183-193.*

(Continued)

*Primary Examiner* — David W Berke-Schlessel
*Assistant Examiner* — Trent R Clarke
(74) *Attorney, Agent, or Firm* — Wolf, Greenfield & Sacks, P.C.

(57) ABSTRACT

Provided here in are methods and compositions for delivering a payload molecule to a charged avascular tissue or charged partially vascularized tissue in a subject, the method including administering to a subject in need thereof an effective amount of a carrier, wherein the carrier is a cationic carrier and/or has a surface charge distribution such that about 40% or greater of a continuous region of the surface is positively charged, and wherein the carrier is linked with a payload molecule, to deliver the payload molecule to the charged avascular tissue and/or the charged partially vascularized tissue.

12 Claims, 26 Drawing Sheets

Specification includes a Sequence Listing.

(51) Int. Cl.
*A61K 38/20* (2006.01)
*A61K 38/30* (2006.01)
*A61P 19/02* (2006.01)
*C07K 14/435* (2006.01)
*C07K 14/65* (2006.01)

(52) U.S. Cl.
CPC .............. *A61K 38/30* (2013.01); *A61P 19/02* (2018.01); *C07K 14/43595* (2013.01); *C07K 14/65* (2013.01); *C07K 2319/60* (2013.01); *C07K 2319/92* (2013.01)

(56) References Cited

OTHER PUBLICATIONS

Yamini Krishnan et al., Green fluorescent proteins engineered for cartilage-targeted drug delivery: Insights for transport into highly charged avascular tissues, 2018, Biomaterials, vol. 183, pp. 218-233 + Supplementary Material (pp. 1-31), published online Aug. 25, 2018 (Year: 2018).*

Zhang X, Wu S, Naccarato T, Prakash-Damani M, Chou Y, Chu C-Q, et al., Regeneration of hyaline-like cartilage in situ with SOX9 stimulation of bone marrow-derived mesenchymal stem cells. PLoS ONE, vol. 12, No. 6, e0180138 (Year: 2017).*

Y. Li, Y. Wang, S. Chubinskaya, B. Schoeberl, E. Florine, P. Kopesky, A.J. Grodzinsky, Effects of insulin-like growth factor-1 and dexamethasone on cytokine-challenged cartilage: relevance to post-traumatic osteoarthritis, 2015, Osteoarthritis and Cartilage, vol. 23, pp. 266-274 (Year: 2015).*

Xiaoying Chen, Jennica L. Zaro, Wei-Chiang Shen, Fusion protein linkers: Property, design and functionality, 2013, Advanced Drug Delivery Reviews, vol. 65, pp. 1357-1369 (Year: 2013).*

Lan E. Gentle, David P. De Souza, and Manuel Baca, Direct Production of Proteins with N-Terminal Cysteine for Site-Specific Conjugation, 2004, Bioconjugate Chem., vol. 15, pp. 658-663 (Year: 2004).*

Ulrike Billmeier, Walburga Dieterich, Markus F Neurath, Raja Atreya, Molecular mechanism of action of anti-tumor necrosis factor antibodies in inflammatory bowel diseases, 2016, World J Gastroenterol, vol. 22(42), pp. 9300-9313 (Year: 2016).*

Instant SEQ 13 (Query) aligned to Liu +15GFP (Sbjct) performed on NCBI Blast Jun. 4, 2025 (Year: 2025).*

Instant SEQ 13 (Query) aligned to Liu +15GFP with N-term Cys (Sbjct) performed with NCBI Blast Jun. 4, 2025 (Year: 2025).*

David B. Thompson, James J. Cronican and David R. Liu, Engineering and Identifying Supercharged Proteins for Macromolecule Delivery into Mammalian Cells, 2012, Chapter 12, Methods in Enzymology, vol. 503, pp. 293-319 (Year: 2012).*

Instant SEQ 13 (Query) aligned with Liu +15GFP with (GGS)9 linker and N-term Cys (Sbjct) performed with NCBI Blast on Jun. 4, 2025 (Year: 2025).*

Instant SEQ 1 (Query) aligned to SEQ 5 of Bowdish (Sbjct) with NCBI blastp tool on Nov. 19, 2025 (Year: 2025).*

Bajpayee et al., Avidin as a model for charge driven transport into cartilage and drug delivery for treating early stage post-traumatic osteoarthritis. Biomaterials. Jan. 2014;35(1):538-49. doi: 10.1016/j.biomaterials.2013.09.091. Epub Oct. 10, 2013. PMID: 24120044; PMCID: PMC3863604.

Byun et al., Silibrium uptake of a peptide inhibitor of PACE4 into articular cartilage is dominated by electrostatic interactions. Arch Biochem Biophys. Jul. 2010;499(1-2):32-9. doi: 10.1016/j.abb.2010.04.019. Epub May 4, 2010. PMID: 20447377; PMCID: PMC2885539.

Chen et al., Fusion protein linkers: property, design and functionality. Adv Drug Deliv Rev. Oct. 2013;65(10):1357-69. doi: 10.1016/j.addr.2012.09.039. Epub Sep. 29, 2012. PMID: 23026637; PMCID: PMC3726540.

Eppstein et al., Biological activity of liposome-encapsulated murine interferon gamma is mediated by a cell membrane receptor. Proc Natl Acad Sci U S A. Jun. 1985;82(11):3688-92. doi: 10.1073/pnas.82.11.3688. PMID: 3159018; PMCID: PMC397852.

Hwang et al., Hepatic uptake and degradation of unilamellar sphingomyelin/cholesterol liposomes: a kinetic study. Proc Natl Acad Sci U S A. Jul. 1980;77(7):4030-4. doi: 10.1073/pnas.77.7.4030. PMID: 6933450; PMCID: PMC349762.

Levick et al., Fluid movement across synovium in healthy joints: role of synovial fluid macromolecules. Ann Rheum Dis. May 1995;54(5):417-23. doi: 10.1136/ard.54.5.417. PMID: 7794053; PMCID: PMC1005608.

Malda et al., Of mice, men and elephants: the relation between articular cartilage thickness and body mass. PLoS One. 2013;8(2):e57683. doi: 10.1371/journal.pone.0057683. Epub Feb. 21, 2013. PMID: 23437402; PMCID: PMC3578797.

Reddy et al., Linkers in the structural biology of protein-protein interactions. Protein Sci. Feb. 2013;22(2):153-67. doi: 10.1002/pro.2206. Epub Jan. 8, 2013. PMID: 23225024; PMCID: PMC3588912.

Thompson et al., Cellular uptake mechanisms and endosomal trafficking of supercharged proteins. Chem Biol. Jul. 27, 2012;19(7):831-43. doi: 10.1016/j.chembiol.2012.06.014. PMID: 22840771; PMCID: PMC3408882.

International Search Report and Written Opinion for PCT/US2013/073062, mailed on May 20, 2014.

International Preliminary Report on Patentability for PCT/US2013/073062, mailed on Jun. 9, 2015.

Krishnan et al., Green fluorescent proteins engineered for cartilage-targeted drug delivery: Insights for transport into highly charged avascular tissues. Biomaterials. Nov. 2018;183:218-233. doi: 10.1016/j.biomaterials.2018.08.050. Epub Aug. 25, 2018. PMID: 30173104; PMCID: PMC6141342.

* cited by examiner

MULTI-TARGETED, TUNABLE, SUSTAINED DELIVERY OF PAYLOADS TO CHARGED AVASCULAR TISSUES

CROSS-REFERENCE TO RELATED APPLICATIONS

This application claims priority under 35 U.S.C. § 119(e) to U.S. Provisional Application No. 62/879,311, filed on Jul. 26, 2019, which is hereby incorporated by reference in its entirety.

FEDERALLY SPONSORED RESEARCH

This invention was made with Government support under Grant No. R01 EB026344 awarded by the National Institutes of Health (NIH), Grant No. DMR1419807 awarded by the National Science Foundation (NSF), and Grant No. W81XWH-14-1-0544 awarded by the U.S. Army Medical Research and Material Command (USAMRMC). The Government has certain rights in the invention.

BACKGROUND

Avascular tissues and/or partially vascularized tissues such as articular cartilage and intervertebral discs have a very low cell density and a densely packed extracellular matrix (ECM) that has high levels of macromolecules containing fixed negative charge groups. In addition to the dense ECM, these tissues either lack blood vessels altogether or have some vasculature that does not completely penetrate the tissue. Such tissue structures make it difficult to get drugs and other molecules/particles into the tissue, and particularly to the cells, in a sustained manner for prolonged periods of time. It is therefore of interest to develop a carrier based delivery system for payload molecule delivering to avascular tissue and/or partially vascularized tissue.

SUMMARY

The present disclosure, at least in part, relates to methods and compositions for delivering payload molecules (e.g., therapeutic or diagnostic agents) to a tissue (e.g., charged avascular tissue or charged partially vascularized tissue) using a carrier (e.g., charged carrier).

In some aspects, the disclosure provides a method for delivering a payload molecule to a charged avascular tissue or a charged partially vascularized tissue in a subject, the method including: administering to a subject in need thereof an effective amount of a carrier, wherein the carrier is a cationic carrier and/or has a surface charge distribution such that about 40% or greater of a continuous region of the surface is positively charged, and wherein the carrier is linked with a payload molecule, to deliver the payload molecule to the charged avascular tissue or charged partially vascularized tissue. In some embodiments, the carrier is a synthetic carrier or a natural carrier. In some embodiments, the carrier is a peptide carrier or a nanoparticle. In some embodiments, the charged avascular tissue is articular cartilage, an intervertebral disc, meniscus, cornea, tracheal cartilage, costal cartilage, nasal cartilage, auricular cartilage, a tendon, or a ligament. In some embodiments, the carrier has a hydrodynamic diameter of less than 15 nm.

In some embodiments, the payload molecule is delivered to the extracellular space of the charged avascular tissue or the charged partially vascularized tissue. In some embodiments, the carrier has a net neutral charge. In some embodiments, the carrier has a surface charge distribution such that about 40% or greater of a continuous region of the surface is positively charged. In some embodiments, the carrier is an engineered green fluorescence protein (GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 5. In some embodiments, the carrier has a net positive charge. In some embodiments, the carrier has a net positive charge of +6 to +20. In some embodiments, the carrier has a net positive charge of +9 to +15. In some embodiments, the carrier has a net positive charge of +9. In some embodiments, the carrier is an engineered super charged green fluorescence protein (S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 1. In some embodiments, the carrier has a net positive charge of +15. In some embodiments, the carrier is an engineered super charged green fluorescent protein (S-GFP) having an amino acid sequence that is at least 80% identical, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 2, SEQ ID NO: 12, or SEQ ID NO: 13.

In some embodiments, the payload molecule is delivered to cells in the charged avascular tissue. In some embodiments, the payload molecule is delivered to the cell surface. In some embodiments, the payload molecule is delivered to the intracellular space of the cells. In some embodiments, the carrier has a net positive charge. In some embodiments, the carrier has a net positive charge of +21 to +48. In some embodiments, the carrier has a net positive charge of +25 to +36. In some embodiments, the carrier has a net positive charge of +25. In some embodiments, the carrier is an engineered super charged green fluorescence protein (S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 3. In some embodiments, the engineered super charged green fluorescence protein (S-GFP) has a net positive charge of +36. In some embodiments, the carrier is an engineered super charged green fluorescence protein (GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 4.

In some embodiments, the payload molecule is a protein, a small molecule, a nucleic acid, or an imaging molecule. In some embodiments, the payload molecule is a protein. In some embodiments, the protein is an insulin growth factor-1 (IGF-1), a Cas protein, FGF-18, an antibody, or IL-1Ra. In some embodiments, the antibody is an anti-TNF antibody, an anti-SOST antibody, an anti-matrix metalloproteinase antibody, or an antiaggrecanase antibody.

In some embodiments, the payload molecule is a small molecule or a pharmaceutically acceptable salt thereof. In some embodiments, the small molecule is dexamethasone, a corticosteroid (e.g., triamcinolone, prednisolone), a TLR inhibitor (e.g., TAK-242, o-vanillin), a senolytic (e.g., navitoclax), a kinase inhibitor (e.g., SP600125 (JNK1/2 inhibitor), an ERK-5 inhibitor (e.g., XMD8-92), a JAK3 inhibitor (e.g., CP690550), strontium ranelate, or kartogenin. In some embodiments, the small molecule is dexamethasone.

In some embodiments, the carrier further comprises a cysteine at the N-terminus. In some embodiments, the carrier further comprises a linker. In some embodiments, the linker is a flexible linker or a rigid linker. In some embodiments, the flexible linker is $(GGGGS)_4$ (SEQ ID NO: 27), $(GGGGS)_3$ (SEQ ID NO: 28) or $(GGS)_9$ (SEQ ID NO: 29). In some embodiments, the rigid linker is $(EAAAK)_3$ (SEQ ID NO: 30) or $A(EAAAK)_4ALEA(EAAAK)_4A$ (SEQ ID NO: 31). In some embodiments, the linker is an acid cleavable linker or an enzyme cleavable linker. In some embodiments, the linker is positioned between the carrier and the payload molecule. In some embodiments, the payload molecule is released from the carrier by cleavage of the linker.

In some embodiments, the administration of the carrier is by local injection. In some embodiments, the subject is a human. In some embodiments, the subject has or is at risk of having joint disease, pseudogout, an orphan disease, a genetic disorder, an autoimmune disorder, or a cancer. In some embodiments, the joint disease is osteoarthritis, intervertebral disc degeneration or a muscularskeletal disease. In some embodiments, the genetic disorder is chondrodysplasia, or mucopolysaccharidosis. In some embodiments, the autoimmune disorder is relapsing polychondritis. In some embodiments, the joint disease is osteoarthritis, and the method comprises administering the subject a first carrier linked with a pro-anabolic protein and/or a second carrier linked with an anti-catabolic and/or anti-inflammatory small molecule. In some embodiments, the first carrier linked with a pro-anabolic protein is a +9 super charged green fluorescent protein (+9 S-GFP) linked with an IGF-1. In some embodiments, the second carrier linked with an anti-catabolic and/or anti-inflammatory small molecule is a +15 super charged green fluorescent protein (+15 S-GFP) linked with dexamethasone. In some embodiments, the carrier comprises an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any one of the amino acid sequences of SEQ ID NOs: 6-13. In some embodiments, the (+9 S-GFP) linked with an IGF-1 comprises an amino acid sequence that is at least 80% identical to the amino acid sequence of any one of SEQ ID NOs: 6-11 and/or the +15 S-GFP comprises an amino acid sequence that is at least 80% identical to the amino acid sequence of SEQ ID NO: 12 or SEQ ID NO: 13. In some embodiments, the subject is a non-human mammal.

In some aspects, the present disclosure also provides a composition, comprising: a carrier, wherein the carrier is a cationic peptide and/or has a surface charge distribution such that about 40% or greater of a continuous region of the surface is positively charged, and wherein the carrier is linked with a payload molecule. In some embodiments, the carrier is a synthetic carrier or a natural carrier. In some embodiments, the carrier is a peptide carrier or a nanoparticle. In some embodiments, the carrier is capable of delivering the payload molecule to a charged avascular tissue and/or a charged partially vascularized tissue. In some embodiments, the charged avascular tissue is articular cartilage, an intervertebral disc, meniscus, cornea, tracheal cartilage, costal cartilage, nasal cartilage, auricular cartilage, a tendon, or a ligament. In some embodiments, the carrier has a hydrodynamic diameter of less than 15 nm. In some embodiments, the carrier is capable of delivering the payload molecule to the extracellular space of the charged avascular tissue. In some embodiments, the carrier has a net neutral charge. In some embodiments, the carrier has a surface charge distribution such that about 40% or greater of a continuous region of the surface is positively charged.

In some embodiments, the carrier is a engineered green fluorescence protein (GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 5. In some embodiments, the carrier has a net positive charge. In some embodiments, the carrier has a net positive charge of +6 to +20. In some embodiments, the carrier has a net positive charge of +9 to +15. In some embodiments, the carrier has a net positive charge of +9. In some embodiments, the carrier is a engineered super charged green fluorescence protein (S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 1. In some embodiments, the carrier has a net positive charge of +15. In some embodiments, the carrier is an engineered super charged green fluorescence protein (S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 2. In some embodiments, the carrier is capable of delivering the payload molecule to cells in the charged avascular tissue. In some embodiments, the carrier is capable of delivering the payload molecule to the cell surface. In some embodiments, the carrier is capable of delivering the payload molecule to the intracellular space of the cells. In some embodiments, the carrier has a net positive charge. In some embodiments, the carrier has a net positive charge of +21 to +48. In some embodiments, the carrier has a net positive charge of +25 to +36. In some embodiments, the carrier has a net positive charge of +25. In some embodiments, the carrier is an engineered super charged green fluorescence protein (S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 3. In some embodiments, the carrier has a net positive charge of +36. In some embodiments, the carrier is an engineered super charged green fluorescence protein (S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 4. In some embodiments, the payload molecule is a protein, a small molecule, a nucleic acid, or an imaging molecule. In some embodiments, the payload molecule is a protein. In some embodiments, the protein is an insulin growth factor-1 (IGF-1), a Cas protein, FGF-18, an antibody, or IL-1Ra. In some embodiments, the antibody is an anti-TNF antibody, an anti-SOST antibody, an anti-matrix metalloproteinase antibody, or an anti-aggrecanase antibody. In some embodiments, the payload molecule is a small molecule or a pharmaceutically acceptable salt thereof. In some embodiments, the small molecule is dexamethasone, a corticosteroid (e.g., triamcinolone, prednisolone), a TLR inhibitor (e.g., TAK-242, o-vanillin), a senolytic (e.g., navitoclax), a kinase inhibitor (e.g., SP600125 (JNK1/2 inhibitor), an ERK-5 inhibitor (e.g., XMD8-92), a JAK3 inhibitor (e.g., CP690550), strontium ranelate, or kartogenin. In some embodiments, the small molecule is dexamethasone. In some embodiments, the carrier further comprises a cysteine at the N-terminus. In some embodiments, the carrier further comprises a linker. In some embodiments, the linker is a flexible linker or a rigid linker. In some embodiments, the flexible linker is $(GGGGS)_4$ (SEQ ID NO: 27), $(GGGGS)_3$ (SEQ ID NO: 28) or $(GGS)_9$ (SEQ ID NO: 29). In some embodiments, the rigid linker is $(EAAAK)_3$ (SEQ ID NO: 30) or $A(EAAAK)_4ALEA(EAAAK)_4A$ (SEQ ID NO: 31). In some embodiments, the linker is an acid cleavable linker or an enzyme cleavable linker. In some embodiments, the linker is positioned between the carrier and the payload molecule. In some embodiments, the payload molecule is released from the carrier by cleavage of the linker. In some embodiments, the carrier comprises an amino acid sequence that is at least 80%, at least 85%, at least 90%, at least 91%, at least 92%, at least 93%, at least 94%, at least 95%, at least 96%, at least 97%, at least 98%, at least 99%, or 100% identical to any one of the amino acid sequences of SEQ ID NOs: 6-13. In some embodiments, the (+9 S-GFP) linked with an IGF-1 comprises an amino acid sequence that is at least 80% identical to the amino acid sequence of any one of SEQ ID NOs: 6-11 and/or the +15 S-GFP comprises an amino acid sequence that is at least 80% identical to the amino acid sequence of SEQ ID NO: 12 or SEQ ID NO: 13. In some embodiments, the composition further comprises a pharmaceutically acceptable carrier. In some embodiments, the composition is formulated for local injection. In some embodiments, the composition is formulated for sustained release of the payload molecule.

In some aspects, the present disclosure also provides an isolated nucleic acid comprising a nucleic acid sequence that is at least 80%, at least 85%, at least 90%, at least 91%, at least 92%, at least 93%, at least 94%, at least 95%, at least 96%, at least 97%, at least 98%, at least 99%, or 100% identical to any one of the nucleotide sequences of SEQ ID NOs: 14-26.

In some aspects, the present disclosure also provides a method for treating a disease associated with charged avascular tissue in a subject in need thereof, comprising: administering to a subject a therapeutically effective amount of the aforementioned composition, or the aforementioned isolated nucleic acid.

In some aspects, the present disclosure also provides a method for identifying a carrier suitable for delivering a payload molecule to a charged avascular tissue, comprising: determining the net surface charge of the carrier for optimized tissue uptake; determining the surface charge distribution of the carrier for optimized tissue uptake; and determining the linker for optimized tissue uptake.

In some embodiments, the nanoparticles of the present disclosure are comprised of peptides but specifically exclude a positively charged peptide carrier comprised of avidin, albumin, gelatin, lysozyme, and amphiphilic triblock peptides. In some embodiments, the nanoparticles of the present disclosure are comprised of peptides but specifically exclude a positively charged peptide carrier having a net + charge of 6-20.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

FIG. 1A shows at the 3-day time point, the aggrecan biosynthesis rate for the 500 nM (+9GFP)-$(GGGGS)_4$-(IGF-1) (SEQ ID NO: 7) group is significantly higher compared to the untreated control. The aggrecan biosynthesis rates for the 2 μM (+9GFP)-$(GGGGS)_4$-(IGF-1) (SEQ ID NO: 7) group and the 500 nM (+9GFP)-$(EAAAK)_3$-(IGF-1) (SEQ ID NO: 8) group are not statistically significantly different from the untreated control group, but the p-values are 0.0685 and 0.061 respectively (these are close to the 0.05 cutoff value for significance). The biosynthesis rate for the continuous free IGF-1 treatment is significantly higher than the rate for the untreated control, but it is not statistically significantly different from the rates for the 500 nM (+9GFP)-$(GGGGS)_4$-(IGF-1) (SEQ ID NO: 7) group, the 2 μM (+9GFP)-$(GGGGS)_4$-(IGF-1) (SEQ ID NO: 7) group and the 500 nM (+9GFP)-$(EAAAK)_3$-(IGF-1) (SEQ ID NO: 8) group. These results demonstrate that the (+9GFP)-$(GGGGS)_4$-(IGF-1) (SEQ ID NO: 7) fusion protein is bioactive and a 500 nM dose is sufficient to get a response. They also indicate that the (+9GFP)-$(EAAAK)_3$-(IGF-1) (SEQ ID NO: 8) is potentially bioactive as well. FIG. 1B shows at the 7-day time point, the biosynthesis rate for the continuous free IGF-1 treatment is significantly higher than the rate for the untreated control. At the same time point, the aggrecan biosynthesis rates for the 500 nM (+9GFP)-$(GGGGS)_4$-(IGF-1) (SEQ ID NO: 7) group and the 2 μM (+9GFP)-$(GGGGS)_4$-(IGF-1) (SEQ ID NO: 7) group are not statistically significantly different from the untreated control, but they are also not different compared to the continuous free IGF-1 treatment group. FIG. 1C shows the comparison between the 3-day time point (dark gray bars) and the 7-day time point (light gray bars) for all the treatment groups. The mean aggrecan biosynthesis rate at Day 7 is the same as the rate on Day 3 for the 500 nM and 2 μM doses of (+9GFP)-$(GGGGS)_4$-(IGF-1) (SEQ ID NO: 7). This indicates that a single dose on Day 0 of this fusion protein is able to maintain a prolonged response in cartilage tissue. Bars: Mean±Std. Dev. *: $p<0.05$, : $p<0.01$, *: $p<0.001$ FIG. 2A shows at the 3-day time point, the aggrecan biosynthesis rate for the continuous free IGF-1 group, the 500 nM and 2 μM doses of (+9GFP)-$(GGGGS)_4$-(IGF-1) (SEQ ID NO: 7) as well as the 1 μM and 2 μM doses of (+9GFP)-$(EAAAK)_3$-(IGF-1) (SEQ ID NO: 8) are all statistically significantly higher compared to the untreated control. These results demonstrate that both (+9GFP)-$(GGGGS)_4$-(IGF-1) (SEQ ID NO: 7) and (+9GFP)-$(EAAAK)_3$-(IGF-1) (SEQ ID NO: 8) are bioactive in human cartilage at doses equal to or greater than 500 nM. There are no statistically significant differences between the continuous free IGF-1 group and any of the fusion protein treatment groups. FIG. 2B shows at the 7-day time point, the aggrecan biosynthesis rate for the continuous free IGF-1 group, the 1 μM and 2 μM doses of (+9GFP)-$(GGGGS)_4$-(IGF-1) (SEQ ID NO: 7) as well as the 1 μM and 2 μM doses of (+9GFP)-$(EAAAK)_3$-(IGF-1) (SEQ ID NO: 8) are all statistically significantly higher compared to the untreated control. The aggrecan biosynthesis rate for the continuous free IGF-1 group is significantly higher than all groups except for the 2 μM dose of (+9GFP)-$(GGGGS)_4$-(IGF-1) (SEQ ID NO: 7) and the 2 μM dose of (+9GFP)-$(EAAAK)_3$-(IGF-1) (SEQ ID NO: 8). These results provide additional evidence that (+9GFP)-$(GGGGS)_4$-(IGF-1) (SEQ ID NO: 7) and (+9GFP)-$(EAAAK)_3$-(IGF-1) (SEQ ID NO: 8) are bioactive in human cartilage, and a single dose of both these fusion proteins has a prolonged effect that lasts for at least 1 week after administration. FIG. 2C shows the comparison between the 3-day time point (dark gray bars) and the 7-day time point (light gray bars) for all the treatment groups. Bars: Mean±Std. Dev. *: $p<0.05$, : $p<0.01$, *: $p<0.001$ FIG. 3A shows at the 3-day time point, the aggrecan biosynthesis rate for the continuous free IGF-1 group as well as the 500 nM and 2 μM doses of (+9GFP)-$(GGGGS)_4$-(IGF-1) (SEQ ID NO: 7) are all statistically significantly higher compared to the untreated control. These results demonstrate that the (+9GFP)-$(GGGGS)_4$-(IGF-1) (SEQ ID NO: 7) fusion protein is bioactive in human ankle cartilage. There are no statistically significant differences between the continuous free IGF-1 group and any of the fusion protein treatment groups. This indicates that (+9GFP)-$(EAAAK)_3$-(IGF-1) (SEQ ID NO: 8) is also potentially bioactive. The three +9 GFP control groups are not statistically significantly different from the untreated control group. This indicates that the carrier domain in the fusion protein does not have any effect on the biosynthesis rate at doses between 500 nM and 2 μM. Any changes in the biosynthesis rate are only due to the IGF-1 domain. FIGS. 3B-3C show at the 7-day time point, the aggrecan biosynthesis rate for the continuous free IGF-1 group, the 500 nM and 1 μM doses of (+9GFP)-$(GGGGS)_4$-(IGF-1) (SEQ ID NO: 7) as well as all three doses of (+9GFP)-$(EAAAK)_3$-(IGF-1) (SEQ ID NO: 8) are statistically significantly higher compared to the untreated control. This demonstrates that both (+9GFP)-$(GGGGS)_4$-(IGF-1) (SEQ ID NO: 7) and (+9GFP)-$(EAAAK)_3$-(IGF-1) (SEQ ID NO: 8) are bioactive in human ankle cartilage at dose levels greater than or equal to 500 nM. The aggrecan biosynthesis rate for the continuous free IGF-1 group is not statistically significantly different from any of the 6 groups with the fusion proteins. This indicates that a single dose of these fusion proteins at the start of the experiment can provide a sustained effect that is comparable to continuous dosing of free IGF-1 for a duration of 1 week. Similar to the 3-day experiment, the three +9 GFP control groups are not statistically significantly different from the untreated control group. FIG. 3D shows comparison of aggrecan biosynthesis rate at the 3-day time point and the 7-day timepoint. Bars: Mean±Std. Dev. *: $p<0.05$, : $p<0.01$, *: $p<0.001$ FIGS. 4A and 4B show 36 hour uptake ratios and 108 hour uptake ratios. FIG. 4C show a comparison of 36 hour and 108 hour uptake ratios. Bars: Mean±Std. Dev. *: $p<0.05$, : $p<0.01$, *: $p<0.001$ (Statistics: 1-way ANOVA with post-hoc Tukey's HSD test)

FIGS. 6A-6B show 40 nM free IGF-1 is able to completely rescue the biosynthesis loss caused by 100 pg/ml of human IL-1β. At 500 pg/ml and 1000 pg/ml doses of human IL-1β, adding 40 nM of free IGF-1 is less effective, and it only leads to a partial rescue of biosynthesis. Based on these experiments, 100 pg/ml of IL-1β was chosen as the optimal dose to simulate osteoarthritis in human cartilage explants and screen various drugs for disease modifying effects. FIG. 6C shows 40 nM free IGF-1 is able to completely rescue the biosynthesis loss caused by 100 pg/ml of human IL-1β. Both dose levels of (+9GFP)-$(EAAAK)_3$-(IGF-1) (SEQ ID NO: 8) are also able to rescue the biosynthesis loss caused by 100 pg/ml of human IL-1β.

FIG. 8B shows that fusion proteins were expressed in *E. coli* and purified using immobilized metal affinity chromatography (with Nickel NTA resin) followed by ion-exchange chromatography. FIG. 8C shows the NuPAGETM 4-12% Bis-Tris Protein gel (Invitrogen) showing recombinant human IGF-1 (PeproTech), purified +9GFP-IGF-1 fusion proteins, and purified +9GFP.

FIG. 10A shows confocal microscopy images of cartilage explants treated with single 1 μM doses of three different +9GFP-IGF-1 fusion protein variants. An untreated control and a group with continuous free IGF-1 dosage are included for comparison. (Scale bar: 200 μm.) FIG. 10B shows the fluorescence intensities of the images in FIG. 10A. The X-axis is the distance in pixels from left to right of each image. The figures in the second column show the fluorescence intensities along a line within each image in FIG. 10A. The fluorescence intensities were also vertically averaged over the entire height of each image and these are shown as a function of distance along the X-axis in the figures in the first column.

FIG. 11A shows confocal microscopy images of cartilage explants treated with single 1 μM doses of two +9GFP-IGF-1 fusion protein variants. An untreated control is shown for comparison. (Scale bar: 200 μm.) FIG. 11B shows fluorescence intensities of the images in FIG. 11A. The X-axis is the distance in pixels from left to right of each image. The figures in the second column show the fluorescence intensities along a line within each image in FIG. 11A. The fluorescence intensities were also vertically averaged over the entire height of each image and these are shown as a function of distance along the X-axis in the figures in the first column.

FIGS. 13A-13B show the cumulative percent sGAG loss and final explant sGAG content (normalized to wet weight) for the ankle cartilage dose response experiments in FIG. 12A. FIGS. 13C-13D show the cumulative percent sGAG loss and final explant sGAG content (normalized to wet weight) for the knee cartilage dose response experiments in FIG. 12B. All bars represent least squares means with 95% confidence intervals.

FIG. 15A shows the normalized sulfate incorporation rate measured during day 5 to 7 of a 7-day long experiment with explants from five ankle donors (N=6 to 10 explants/condition/donor). FIG. 15B shows the normalized sulfate incorporation rate measured during day 7 to 10 of a 10-day long experiment with explants from two ankle donors (N=8 to 11 explants/condition/donor). FIG. 15C shows the cumulative percent sGAG loss from the explants in FIGS. 15A-15B. FIG. 15D shows the total explant sGAG content normalized to wet weight at the end of the experiments in FIGS. 15A-15B.

FIG. 19A shows that only the free IGF-1 group had a significantly increased sulfate incorporation rate compared to the untreated control. FIG. 19B shows that there were no differences between the proline incorporation rates of any of the groups. Bars represent least squares mean values with 95% confidence interval.

DETAILED DESCRIPTION

Figure 1A:
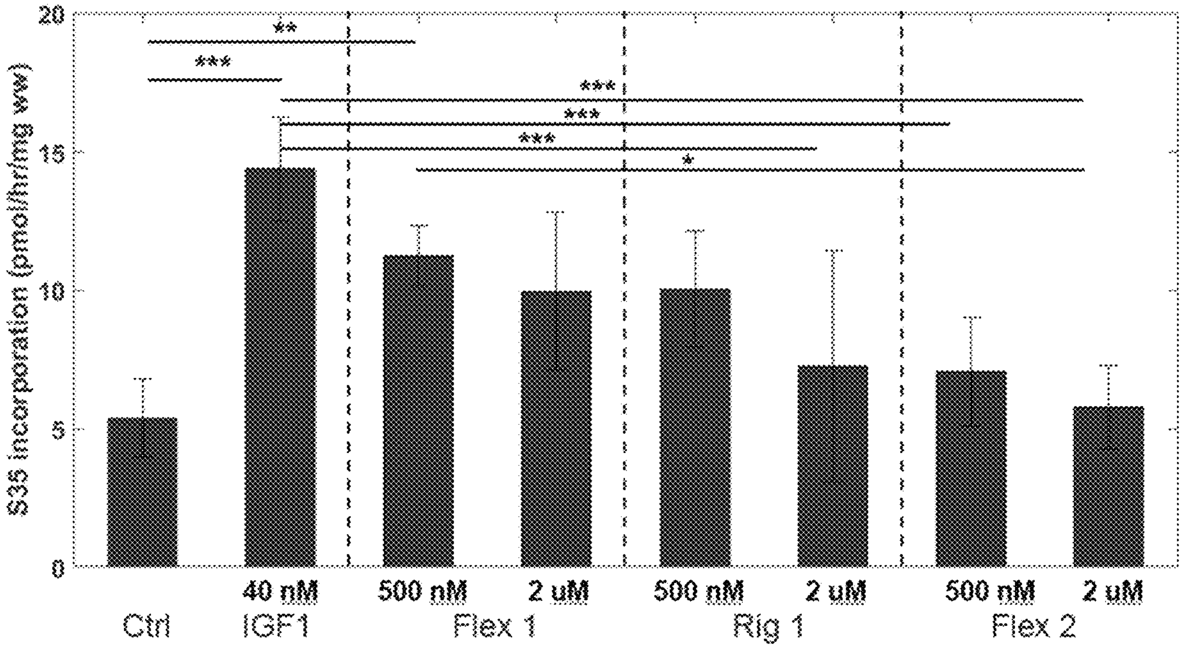
FIGS. 1A-1C show aggrecan biosynthesis rate measured between days 0 and 3; days 5 and 7, and at the 7-day time point and the 3-day time point in experiment 3.

Methods and compositions facilitating carrier based payload molecule delivery for the prevention and/or treatment of disease are provided according to the present disclosure. In particular, the carrier described herein can be useful for delivering payload molecules to a charged avascular tissue or a charged partially vascularized tissue for sustained release of the payload molecule to the tissue for long periods of time.

I. Carrier Based Payload Delivery

The present disclosure, at least in part, relates to a carrier for delivery of payload molecules to a charged avascular tissue or a charged partially vascularized tissue. It is difficult to get drugs and other molecules/particles into such tissues and/or to cells in such tissues, in a sustained manner for prolonged periods of time. It is demonstrated herein that the carriers of the present disclosure are advantageously able to penetrate the full thickness of a charged vascular tissue or a charged partially vascularized tissue (e.g, cartilage) within a short period of time (e.g., about 24-48 hours). The ability of the carrier to penetrate the tissues within a short period of time reduces the risk of clearance from the subject when administered in vivo. Further, the payload molecules delivered using the carriers of the disclosure stay within the targeted tissue (e.g., cartilage) for a prolonged period of time (greater than 3 days, greater than 4 days, greater than 5 days, greater 6 days, greater than 7 days, greater than 8 days, greater than 9 days, greater than 10 days, greater than 11 days, greater than 12 days, greater than 13 days, greater than 14 days, or greater than 15 days) after a single administration, thus allowing sustained delivery. The carriers of the disclosure can be used to effectively deliver a broad range of payload molecules that may have their targets in the extracellular matrix, on cell surfaces, or in the intracellular space. The carriers help to create a depot of payload molecules in the tissues where they can subsequently act either on targets in the tissue or be released over a prolonged period of time to neighboring cell and tissue targets. Without wishing to be bound by theory, since the carriers have such a high affinity for constituents inside the charged tissues, most of the carrier-payload conjugate will be sequestered inside the tissues. This would enable the use of minimal doses of drugs that can have therapeutic effects without undesirable off-target side effects. Additional advantages include the tunability of carrier properties to achieve different transport, uptake, penetration and/or localization profiles in a variety of charged avascular or partially vascularized tissue and the ability to deliver both small molecule and large macromolecular payloads.

(i) Carrier

A carrier, as used herein, refers to a molecule that is capable of facilitating the delivery of a payload molecule to a target tissue. The carrier provided herein may contain a net surface charge. In some embodiments, the carrier has a net positive charge. In some embodiments, the carrier is a cationic carrier. In some embodiments, the carrier has a surface net positive charge of +1 to +50. In some embodiments, the carrier has a surface net positive charge of +6 to +48. In some embodiments, the carrier has a surface net positive charge of +6, +7, +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38, +39, +40, +41, +42, +43, +44, +45, +46, +47, or +48. In some embodiments, the carrier has a surface net positive charge of +9. In some embodiments, the carrier has a surface net positive charge of +10. In some embodiments, the carrier has a surface net positive charge of +15. In some embodiments, the carrier has a surface net positive charge of +25. In some embodiments, the carrier has a surface net positive charge of +36.

Alternatively or in addition, the carrier described herein may have a surface charge distribution such that a continuous region of the surface of the carrier is positively charged. In some embodiments, the carrier has a surface charge distribution such that at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or greater of a continuous region of the surface is positively charged. In some embodiments, the carrier has a surface charge distribution such that at least 40% or greater of a continuous region of the surface is positively charged.

The carrier of the present disclosure may have a hydrodynamic diameter of less than 15 nm. In some embodiments, the diameter of the carrier is less than 15 nm, less than 14 nm, less than 13 nm, less than 12 nm, less than 11 nm, less than 10 nm, less than 9 nm, less than 8 nm, less than 7 nm, less than 6 nm, less than 5 nm, less than 4 nm, less than 3 nm, less than 2 nm, less than nm or smaller. In some embodiments, the carrier has a hydrodynamic diameter of 5 nm.

In some embodiments, the carrier is a synthetic carrier. In some embodiments, the carrier is a natural carrier. Non-limiting exemplary carriers are peptide or nanoparticles. In some embodiments, the carrier is a peptide carrier. A peptide carrier, as used herein, refers to a carrier that is a polypeptide and/or a protein. A "peptide" or "protein" refers to a string of at least three amino acids linked together by peptide bonds which may be used interchangeably. Peptide may refer to an individual peptide or a collection of peptides, including only natural amino acids, as well as, non-natural amino acids (i.e., compounds that do not occur in nature but that can be incorporated into a polypeptide chain) and/or amino acid analogs. Also, one or more of the amino acids may be modified, for example, by the addition of a chemical entity such as a carbohydrate group, a phosphate group, a farnesyl group, an isofarnesyl group, a fatty acid group, a linker for conjugation, functionalization, or other modification, etc. Other modifications may include cyclization of the peptide, the incorporation of D-amino acids, etc.

In some embodiments, the carrier is a supercharged protein. A supercharged protein, as used herein, refers to proteins that are engineered to carry a wide range of net theoretical charge and/or surface charge distribution while maintaining almost identical mass, structure and function. Supercharged proteins can be produced by changing non conserved amino acids on the surface of a protein to more polar or charged amino acid residues. The amino acid residues to be modified may be hydrophobic, hydrophilic, charged, or a combination thereof.

In some embodiments, the carriers of the present disclosure exclude a positively charged peptide carrier comprised of avidin, albumin, gelatin, lysozyme, and amphiphilic tri-block peptides. In some embodiments, the carriers of the present disclosure exclude a positively charged peptide carrier having a net + charge of 6-20.

In some embodiments, the carrier is a supercharged green fluorescent protein (S-GFP). A supercharged green fluorescent protein (S-GFP), as used herein, refers to a group of engineered green fluorescent protein that possesses a range of net surface charge. The surface charge of the peptide carrier (e.g., S-GFP) can be a positive net charge, a negative net charge or neutral. In some embodiments, the peptide carrier (e.g., S-GFP) has a positive surface charge. In some embodiments, the peptide carrier (e.g., S-GFP) has a surface net positive charge of +1 to +50. In some embodiments, the peptide carrier (e.g., S-GFP) has a surface net positive charge of +6 to +48. In some embodiments, the peptide carrier (e.g., S-GFP) has a surface net positive charge of +9 to +36. In some embodiments, the peptide carrier (e.g., S-GFP) has a surface net positive charge of +6, +7, +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38, +39, +40, +41, +42, +43, +44, +45, +46, +47, or +48. In some embodiments, the peptide carrier (e.g., S-GFP) has a surface net positive charge of +9. In some embodiments, the peptide carrier (e.g., S-GFP) has a surface net positive charge of +10. In some embodiments, the peptide carrier (e.g., S-GFP) has a surface net positive charge of +15. In some embodiments, the peptide carrier (e.g., S-GFP) has a surface net positive charge of +25. In some embodiments, the peptide carrier (e.g., S-GFP) has a surface net positive charge of +36. In some embodiments, the +9 GFP comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 1. In some embodiments, the +15 GFP comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 2. In some embodiments, the +25 GFP comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 3. In some embodiments, the +36 GFP comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99% or 100% identical to the amino acid sequence of SEQ ID NO: 4.

```
An exemplary +9 GFP amino acid sequence is set forth in SEQ ID NO: 1.
MGHHHHHHGGASKGEELFTGVVPILVELDGDVNGHKFSVRGEGEGDATNGKLTLKFICTTGKLP
VPWPTLVTTLTYGVQCFSRYPDHMKRHDFFKSAMPKGYVQERTISFKKDGKYKTRAEVKFEGRT
LVNRIKLKGRDFKEKGNILGHKLRYNFNSHKVYITADKQKNGIKANFKIRHNVEDGSVQLADHY
QQNTPIGDGPVLLPDNHYLSTQSALSKDPNEKRDHMVLLEFVTAAGITHGMDELYK (SEQ ID
NO: 1)

An exemplary nucleotide sequence encoding +9 GFP is set forth in SEQ ID NO: 14.
ATGGGTCATCACCACCACCATCACGGTGGCGCTAGCAAAGGTGAAGAGCTGTTTACGGGTGTAG
TACCGATCTTAGTGGAATTAGACGGCGACGTGAACGGTCACAAATTTAGCGTGCGCGGCGAAGG
CGAAGGTGACGCTACCAATGGTAAATTGACCCTGAAGTTTATTTGCACAACAGGCAAATTACCC
GTTCCGTGGCCCACCTTAGTGACCACCCTGACCTATGGCGTTCAGTGCTTCAGTCGTTACCCAG
ATCATATGAAACGTCACGATTTTTTCAAATCAGCCATGCCTAAAGGATATGTTCAAGAGCGTAC
AATCAGCTTCAAGAAGGATGGCAAATATAAAACGCGTGCGGAAGTGAAATTTGAAGGCCGCACA
TTAGTAAATCGTATCAAACTGAAAGGTCGTGACTTCAAAGAAAAAGGCAACATTTTAGGCCATA
AACTGCGTTATAACTTTAATTCTCATAAGGTGTATATTACGGCCGATAAACAGAAAAACGGTAT
CAAGGCAAATTTCAAAATTCGCCATAACGTGGAAGACGGCAGCGTTCAATTAGCGGATCATTAT
CAACAAAACACGCCGATTGGTGACGGGCCTGTACTGTTACCTGACAACCACTACCTGAGCACCC
AGTCAGCACTGAGCAAAGATCCGAACGAAAAACGCGATCACATGGTTCTGTTAGAATTCGTGAC
CGCTGCAGGCATTACTCACGGAATGGACGAACTCTACAAG (SEQ ID NO: 14)

An exemplary +15 GFP amino acid sequence is set forth in SEQ ID NO: 2.
MGHHHHHHGGASKGERLFTGVVPILVELDGDVNGHKFSVRGEGEGDATRGKLTLKFICTTGKLP
VPWPTLVTTLTYGVQCFSRYPKHMKRHDFFKSAMPEGYVQERTISFKKDGTYKTRAEVKFEGRT
LVNRIELKGRDFKEKGNILGHKLEYNFNSHNVYITADKRKNGIKANFKIRHNVKDGSVQLADHY
QQNTPIGRGPVLLPRNHYLSTRSALSKDPKEKRDHMVLLEFVTAAGITHGMDELYK (SEQ ID
NO: 2)

An exemplary nucleotide sequence encoding +15 GFP is set forth in SEQ ID NO: 15
ATGGGTCATCACCACCACCATCACGGTGGCGCTAGCAAAGGTGAACGTCTGTTTACGGGTGTAG
TACCGATCTTAGTGGAATTAGACGGCGACGTGAACGGTCACAAATTTAGCGTGCGCGGCGAAGG
CGAAGGTGACGCTACCCGTGGTAAATTGACCCTGAAGTTTATTTGCACAACAGGCAAATTACCC
GTTCCGTGGCCCACCTTAGTGACCACCCTGACCTATGGCGTTCAGTGCTTCAGTCGTTACCCTA
AACATATGAAACGTCACGATTTTTTCAAATCAGCCATGCCTGAAGGATATGTTCAAGAGCGTAC
AATCAGCTTCAAGAAGGATGGCACCTATAAAACGCGTGCGGAAGTGAAATTTGAAGGCCGCACA
TTAGTAAACCGTATCGAACTGAAAGGTCGTGACTTCAAAGAAAAAGGCAACATTTTAGGCCATA
AGCTGGAATATAACTTTAATTCTCATAACGTGTATATTACGGCCGATAAACGCAAGAATGGTAT
CAAGGCAAATTTCAAAATTCGCCATAACGTGAAAGACGGCAGCGTTCAATTAGCGGATCATTAT
CAACAAAACACGCCGATTGGTCGCGGGCCTGTACTGTTACCTCGCAACCACTACCTGAGCACCC
GTTCAGCACTGAGCAAAGATCCGAAAGAAAAACGCGATCACATGGTTCTGTTAGAATTCGTGAC
CGCTGCAGGCATTACTCACGGAATGGACGAACTCTACAAG (SEQ ID NO: 15)

An exemplary +25 GFP amino acid sequence is set forth in SEQ ID NO: 3.
MGHHHHHHGGASKGERLFTGVVPILVELDGDVNGHKFSVRGKGKGDATRGKLTLKFICTTGKLP
VPWPTLVTTLTYGVQCFSRYPKHMKRHDFFKSAMPKGYVQERTISFKKDGTYKTRAEVKFEGRT
```

-continued

LVNRIKLKGRDFKEKGNILGHKLRYNFNSHNVYITADKRKNGIKANFKIRHNVKDGSVQLADHY
QQNTPIGRGPVLLPRNHYLSTRSALSKDPKEKRDHMVLLEFVTAAGTHGMDELYK (SEQ ID
NO: 3)

An exemplary nucleotide sequence encoding +25 GFP is set forth in SEQ ID NO: 16
ATGGGTCATCACCACCACCATCACGGTGGCGCTAGCAAAGGTGAACGTCTGTTTACGGGTGTAG
TACCGATCTTAGTGGAATTAGACGGCGACGTGAACGGTCATAAATTTAGCGTGCGCGGCAAAGG
CAAAGGTGACGCTACCCGTGGTAAATTGACCCTGAAGTTTATTTGCACAACAGGCAAATTACCC
GTTCCGTGGCCCACCTTAGTGACCACCCTGACCTATGGCGTTCAGTGCTTCAGTCGTTACCCTA
AACATATGAAACGTCACGATTTTTTCAAATCAGCCATGCCTAAAGGATATGTTCAAGAGCGTAC
AATCAGCTTCAAGAAGGATGGCACCTATAAAACGCGTGCGGAAGTGAAATTTGAAGGCCGCACA
TTAGTAAATCGTATCAAACTGAAAGGTCGTGACTTCAAAGAAAAAGGCAACATTTTAGGCCATA
AGCTGCGTTATAACTTTAATTCTCATAACGTGTATATTACGGCCGATAAACGCAAGAATGGTAT
CAAGGCAAATTTCAAAATTCGCCATAACGTGAAAGACGGCAGCGTTCAATTAGCGGATCATTAT
CAACAAAACACGCCGATTGGTCGCGGGCCTGTACTGTTACCTCGCAACCACTACCTGAGCACCC
GTTCAGCACTGAGCAAAGATCCGAAAGAAAAACGCGATCACATGGTTCTGTTAGAATTCGTGAC
CGCTGCAGGCATTACTCACGGAATGGACGAACTCTACAAG (SEQ ID NO: 16)

An exemplary +36 GFP amino acid sequence is set forth in SEQ ID NO: 4.
MGHHHHHHGGASKGERLFRGKVPILVELKGDVNGHKFSVRGKGKGDATRGKLTLKFICTTGKLP
VPWPTLVTTLTYGVQCFSRYPKHMKRHDFFKSAMPKGYVQERTISFKKDGKYKTRAEVKFEGRT
LVNRIKLKGRDFKEKGNILGHKLRYNFNSHKVYITADKRKNGIKAKFKIRHNVKDGSVQLADHY
QQNTPIGRGPVLLPRNHYLSTRSKLSKDPKEKRDHMVLLEFVTAAGIKHGRDERYK (SEQ ID
NO: 4)

An exemplary nucleotide sequence encoding +36 GFP is set forth in SEQ ID NO: 17
ATGGGTCATCACCACCACCATCACGGTGGCGCTAGCAAAGGTGAACGTCTGTTTCGTGGTAAAG
TACCGATCTTAGTGGAATTAAAGGGCGACGTGAACGGTCATAAATTTAGCGTGCGCGGCAAAGG
CAAAGGTGACGCTACCCGTGGTAAATTGACCCTGAAGTTTATTTGCACAACAGGCAAATTACCC
GTTCCGTGGCCCACCTTAGTGACCACCCTGACCTATGGCGTTCAGTGCTTCAGTCGTTACCCTA
AACATATGAAACGTCACGATTTTTTCAAATCAGCCATGCCTAAAGGATATGTTCAAGAGCGTAC
AATCAGCTTCAAGAAGGATGGCAAATATAAAACGCGTGCGGAAGTGAAATTTGAAGGCCGCACA
TTAGTAAATCGTATCAAACTGAAAGGTCGTGACTTCAAAGAAAAAGGCAACATTTTAGGCCATA
AACTGCGTTATAACTTTAATTCTCATAAGGTGTATATTACGGCCGATAAACGCAAGAATGGTAT
CAAGGCAAAATTCAAAATTCGCCATAACGTGAAAGACGGCAGCGTTCAATTAGCGGATCATTAT
CAACAAAACACGCCGATTGGTCGCGGGCCTGTACTGTTACCTCGCAACCACTACCTGAGCACCC
GTTCTAAACTGAGCAAAGATCCGAAAGAAAAACGCGATCACATGGTTCTGTTAGAATTCGTGAC
CGCTGCAGGCATTAAGCACGGACGCGACGAACGCTACAAG (SEQ ID NO: 17)

Alternatively or in addition, the carrier is a peptide carrier with a surface charge distribution such that a continuous region of the surface of the carrier is positively charged. In some embodiments, the peptide carrier has a surface charge distribution such that at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or greater of a continuous region of the surface is positively charged. In some embodiments, the peptide carrier has a net positive charge, and/or greater than 40% of a continuous region of the surface of the peptide carrier is positively charged. In some embodiments, the peptide carrier has a net neutral charge, and/or greater than 40% of a continuous region of the surface of the peptide carrier is positively charged. In some embodiments, the peptide carrier has a net negative charge, and/or greater than 40% of a continuous region of the surface of the peptide carrier is positively charged. In some instances, the peptide carrier is an engineered green fluorescence protein (GFP) having a net neutral charge, and/or a greater than 40% of a continuous region of the surface of the carrier is positively charged. An exemplary amino acid sequence of a net neutral charge with more than 40% continuous surface positive charge GFP is set forth in SEQ ID NO: 5. In some embodiments, the net neutral charge with more than 40% continuous surface positive charge GFP comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99% or 100% identical to the amino acid sequence of SEQ ID NO: 5.

An exemplary net charge neutral with more than 40% continuous surface positive charge GFP amino acid sequence is set forth in SEQ ID NO: 5.

(SEQ ID NO: 5)
MGHHHHHHGSACELMVSKGEELFEGDVPILVELDGDVNGHEFSVRGEGEG
DATKGELTLKFICTTGELPVPWPTLVTTLTYGVQCFSRYPKHMKQHDFFK
SAMPEGYVQERTISFKDDGTYKTRAEVKFEGDTLVNRIELKGKDFKEKGN
ILGHKLEYNFNSHRVYITADKRKNGIKAEFKIRHNVKDGSVQLADHYQQN
TPIGRGPVLLPRRHYLSTRSALSKDPKEERDHMVLLEFVTAAGIDHGMDE
LYK

An exemplary nucleotide sequence encoding a net charge neutral with more than 40% continuous surface positive charge GFP is set forth in SEQ ID NO: 18.

(SEQ ID NO: 18)
ATGGGTCACCACCACCACCACCACGGTAGCGCGTGCGAGCTGATGGTTAG
CAAAGGCGAGGAACTGTTCGAGGGTGACGTGCCGATCCTGGTTGAACTGG
ACGGCGATGTGAACGGTCACGAATTTAGCGTTCGTGGTGAGGGCGAAGGT
GATGCGACCAAGGGCGAGCTGACCCTGAAATTCATTTGCACCACCGGTGA
ACTGCCGGTGCCGTGGCCGACCCTGGTTACCACCCTGACCTACGGTGTGC
AGTGCTTTAGCCGTTATCCGAAGCACATGAAACAACACGACTTCTTTAAG
AGCGCGATGCCGGAGGGCTACGTTCAGGAACGTACCATCAGCTTCAAGGA

-continued

```
CGATGGTACCTATAAAACCCGTGCGGAAGTGAAGTTTGAAGGCGACACCC
TGGTTAACCGTATCGAGCTGAAGGGTAAAGATTTCAAGGAAAAAGGCAAC
ATTCTGGGTCACAAACTGGAGTACAACTTTAACAGCCACCGTGTGTATAT
CACCGCGGATAAGCGTAAAAACGGCATCAAGGCGGAATTTAAAATTCGTC
ACAACGTGAAGGACGGTAGCGTTCAACTGGCGGATCACTACCAGCAAAAC
ACCCCGATTGGTCGTGGTCCGGTTCTGCTGCCGCGTCGTCACTATCTGAG
CACCCGTAGCGCGCTGAGCAAGGACCCGAAAGAGGAACGTGATCACATGG
TGCTGCTGGAGTTCGTTACCGCGGCGGGCATTGACCACGGTATGGATGAA
CTGTACAAA
```

In other embodiments, the carrier is a nanoparticle. A nanoparticle, as used herein, refers to particles between 1 and 100 nanometres (nm) in size. Non-limiting examples of nanoparticles are lipid nanoparticles, protein nanoparticles, polymer nanoparticles, gold nanoparticles, metal nanoparticles, or quantum dots.

In some embodiments, the nanoparticles of the present disclosure are comprised of peptides but specifically exclude a positively charged peptide carrier comprised of avidin, albumin, gelatin, lysozyme, and amphiphilic triblock peptides. In some embodiments, the nanoparticles of the present disclosure are comprised of peptides but specifically exclude a positively charged peptide carrier having a net + charge of 6-20.

In some embodiments, the nanoparticle is net charge neutral. In some embodiments, the carrier has a net positive charge. In some embodiments, the carrier is a cationic nanoparticle. In some embodiments, the nanoparticle has a surface net positive charge of +1 to +50. In some embodiments, the nanoparticle has a surface net positive charge of +6 to +48. In some embodiments, the carrier has a surface net positive charge of +6, +7, +8, +9, +10, +11, +12, +13, +14, +15, +16, +17, +18, +19, +20, +21, +22, +23, +24, +25, +26, +27, +28, +29, +30, +31, +32, +33, +34, +35, +36, +37, +38, +39, +40, +41, +42, +43, +44, +45, +46, +47, or +48. In some embodiments, the carrier has a surface net positive charge of +9. In some embodiments, the carrier has a surface net positive charge of +10. In some embodiments, the carrier has a surface net positive charge of +15. In some embodiments, the carrier has a surface net positive charge of +25. In some embodiments, the carrier has a surface net positive charge of +36.

Alternatively or in addition, the nanoparticle described herein may have a surface charge distribution such that a continuous region of the surface of the carrier is positively charged. In some embodiments, the nanoparticle has a surface charge distribution such that at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or greater of a continuous region of the surface is positively charged. In some embodiments, the nanoparticle has a surface charge distribution such that at least 40% or greater of a continuous region of the surface is positively charged.

The carrier described herein is capable of delivering a payload molecule to a charged avascular tissue or charged partially vascularized tissue. An avascular tissue, as used herein, refers to tissues that do not contain blood vessels or lymphatics. A partially vascularized tissue, as used herein, refers to tissues that have some vasculature that does not completely penetrate the tissue. Avascular tissue and partially vascularized tissue may have low cell density and a densely packed matrix (ECM) that has high levels of macromolecules containing fixed negative charge groups. Non-limiting examples of an avascular tissue and/or a partially vascularized tissue are articular cartilage, an intervertebral disc, meniscus, cornea, tracheal cartilage, costal cartilage, nasal cartilage, auricular cartilage, a tendon, or a ligament. Such tissue structures make it difficult to get drugs and other molecules/particles into the tissue and/or to the cells, in a sustained manner for prolonged periods of time.

Carriers with various net surface charges and surface charge distributions can be selected for delivery to different target tissues. In some embodiments, the selection step involves determining the optimal surface net charge and surface charge distribution of a carrier that can either deliver the payload molecule to the extracellular matrix, the cell surface, or the intracellular space. In some embodiments, the selection step involves determining optimal surface net charge and surface charge distribution of a carrier according to the intended depth of tissue penetration. In some embodiments, the selection step involves determining the optimal surface net charge and surface charge distribution of a carrier according to the amount of the payload molecule to be delivered to the tissue. Accordingly, in some aspects, the disclosure provides tunable and multi-targeted carriers for selected delivery to different target tissues.

In some embodiments, the carrier is capable of delivering the payload molecule to the extracellular space of a charged avascular tissue or a charged partially vascularized tissue. In some embodiments, the carrier that is capable of delivering the payload molecule to the extracellular space of a charged avascular tissue or a charged partially vascularized tissue has neutral net surface charge and/or a surface charge distribution such that about 40% or greater of a continuous region of the surface is positively charged. In some embodiments, the carrier that has neutral net surface charge and/or a surface charge distribution such that about 40% or greater of a continuous region of the surface is positively charged is an engineered green fluorescent protein. An non-limiting example of the amino acid sequence of the green fluorescent protein that has a neutral net surface charge and/or a surface charge distribution such that about 40% or greater of a continuous region of the surface is positively charged is set forth in SEQ ID NO: 5. In some embodiments, the carrier that is capable of delivering the payload molecule to the extracellular space of a charged avascular tissue or a charged partially vascularized tissue has a net positive surface charge. In some embodiments, the carrier that is capable of delivering the payload molecule to the extracellular space of a charged avascular tissue or a charged partially vascularized tissue has a net positive surface charge of +6 to +20. In some embodiments, the carrier that is capable of delivering the payload molecule to the extracellular space of a charged avascular tissue or a charged partially vascularized tissue has a net positive surface charge of +9 to +15. In some embodiments, the carrier that is capable of delivering the payload molecule to the extracellular space of a charged avascular tissue or a charged partially vascularized tissue has a net positive surface charge of +6, +7, +8, +9, +10, +11, +12, +13, +15, +16, +17, +18, +19, or +20. In some embodiments, the carrier capable of delivering a payload molecule to the extracellular space of a charged avascular tissue or a charged partially vascularized tissue has a net positive charge of +9. In some embodiments, the +9 net positive carrier is an engineered super charged green fluorescence protein (+9 S-GFP) having an amino acid sequence at least 80%, at least 85%, at least 90%, at least 91%, at least 92%, at least 93%, at least 94%, at least 95%, at least 96%, at least 97%, at least 98%, at least 99%, or 100% identical to amino acid sequence of SEQ ID NO: 1. In other embodiments, the carrier capable of delivering a payload molecule to the extracellular space of a charged avascular tissue or a charged partially vascularized tissue has net positive charge of +15. In some embodiments, the +15 net positive carrier is an engineered super charged green fluorescence protein (+15 S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 2.

In some embodiments, the carrier is capable of delivering the payload molecule to the cells of a charged avascular tissue or a charged partially vascularized tissue. In some embodiments, the carrier is capable of delivering the payload molecule to the cell surface of a charged avascular tissue or a charged partially vascularized tissue. In some embodiments, the carrier is capable of delivering the payload molecule to the intracellular space of a charged avascular tissue or a charged partially vascularized tissue. In some embodiments, the carrier that is capable of delivering the payload molecule to the extracellular space of a charged avascular tissue or a charged partially vascularized tissue has a net positive surface charge. In some embodiments, the carrier that is capable of delivering the payload molecule to the extracellular space of a charged avascular tissue or a charged partially vascularized tissue has a net positive surface charge of +12 to +48. In some embodiments, the carrier that is capable of delivering the payload molecule to the extracellular space of a charged avascular tissue or a charged partially vascularized tissue has a net positive surface charge of +15 to +36. In some embodiments, the carrier that is capable of delivering the payload molecule to the extracellular space of a charged avascular tissue or a charged partially vascularized tissue has a net positive surface charge of +12, +13, +14, +15, +16, +17, +18, +19, +20, +21, +22, +23, +24, +25, +26, +27, +28, +29, +30, +31, +32, +33, +34, +35, +36, +37, +38, +39, +40, +41, +42, +43, +44, +45, +46, +47 or +48. In some embodiments, the carrier capable of delivering a payload molecule to the extracellular space of a charged avascular tissue or a charged partially vascularized tissue has net positive charge of +15. In some embodiments, the +15 net positive carrier is an engineered super charged green fluorescence protein (+15 S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 2. In other embodiments, the carrier capable of delivering a payload molecule to the extracellular space of a charged avascular tissue or a charged partially vascularized tissue has net positive charge of +25. In some embodiments, the +25 net positive carrier is an engineered super charged green fluorescence protein (+25 S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 3. In other embodiments, the carrier capable of delivering a payload molecule to the extracellular space of a charged avascular tissue or a charged partially vascularized tissue has a net positive charge of +36. In some embodiments, the +36 net positive carrier is an engineered super charged green fluorescence protein (+36 S-GFP) having an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO: 4.

Additional amino acids can be included at either end of the carrier to facilitate the conjugation of the payload molecule, detection of the molecule, or downstream purification process. In some embodiments, the carrier is a super charged green fluorescence protein, which has an additional cysteine at either the N-terminus or the C-terminus. In other embodiments, the carrier is a super charged green fluorescence protein, which includes a HHHHHH (SEQ ID NO: 32) tag at either the N-terminus or the C-terminus.

(ii) Payload Molecules

The carrier described herein is linked to a payload molecule. A payload molecule, as described herein, refers to a biologically active molecule capable of eliciting a function at the target tissue. Non-limiting examples of the payload molecules are proteins, small molecules, nucleic acids, or imaging molecules.

In some embodiments, the payload molecule is a protein. Non-limiting examples of proteins are growth factors, cytokine/chemokines, antibodies, enzymes, cancer antigens, regulatory proteins, protein based antagonists, protein bases agonists, and gene editing proteins In some embodiments, the protein is a growth factor. Non-limiting examples of growth factors are insulin-growth factor-1 (IGF-1), fibroblast growth factor-18 (FGF-18), those of the transforming growth factor beta (TGF-beta) superfamily, those of the epidermal growth factor (EGF) Family, platelet-derived growth factors (PDGFs), vascular endothelial growth factors (VEGFs), hepatocyte growth factors (HGFs), or colony-stimulating factors (CSFs).

In some embodiments, the payload molecule is a cytokine/chemokine. Non-limiting examples of cytokine/chemokines are: tumor necrosis factors (TNFs), interferons (IFNs), IL1A, IL1B, IL1RN, IL1F5, IL1F6, IL1F7, IL1F8, IL1F9, IL1F10, IL18, IL33, IL2, IL4, IL7, IL9, IL15, IL21, IL3, IL4, IL5, IL13, IL6, IL11, IL12A, IL23A, IL27A, IL31, IL10, IL19, IL20, IL22, IL24, IL26, IL17A, IL17B, IL17C, IL17D, IL25, IL17F, IL8, IL16, IL32, IL34, CCL14, CCL19, CCL20, CCL21, CCL25, CCL27, CXCL12, CXCL13, CXCL-8, CCL2, CCL3, CCL4, CCL5, CCL11, and CXCL10.

In some embodiments, the payload molecule is an enzyme. Suitable enzymes (for operably linking to a synthetic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases.

In some embodiments, the payload molecule is an antibody. Non-limiting examples of antibodies and fragments thereof include: an anti-TNF antibody, an anti-SOST antibody, an anti-matrix metalloproteinases antibody, an anti-aggrecanase antibody, bevacizumab (AVASTIN®), trastuzumab (HERCEPTIN®), alemtuzumab (CAM- PATH®, indicated for B cell chronic lymphocytic leukemia,), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®), Gliomab-H (indicated for brain cancer, melanoma). In some embodiments, the antibody is an antibody that inhibits an immune check point protein, e.g., an anti-PD-1 antibody such as pembrolizumab (Keytruda®) or nivolumab (Opdivo®), or an anti-CTLA-4 antibody such as ipilimumab (Yervoy®).

In some embodiments, the payload molecule is a regulatory protein. A regulatory protein may be, in some embodiments, a transcription factor or an immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1.

In some embodiments, the payload molecule is a protein based antagonist or a protein based agonist such as IL-1Ra, tumor necrosis factor (TNF) antagonist, IL-1 antagonist, IL-6 antagonist, IL-8 antagonist, matrix metalloproteinase (MMP) antagonist, or aggrecanase antagonist.

In some embodiments, the payload molecule is a cancer antigen. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-05. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, 1mp-1, PIA, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, CD20 and c-erbB-2.

In some embodiments, the payload molecule is a gene editing protein. In some embodiments, the gene editing protein is a CRISPR/Cas protein. In some embodiments, the CRISPR/Cas protein is a Cas9 protein, a nickase protein, a Cas endoribonuclease, or a dCas fusion protein.

In some embodiments, the payload molecule is a nucleic acid. Non-limiting examples of nucleic acid are DNA, RNA, viral replicons, anti-sense nucleic acid, microRNA (miRNA), small interference RNA (siRNA), short hairpin RNA (shRNA) or non-coding RNAs.

In some embodiments, the payload molecule is an imaging molecule. Non-limiting examples of imaging molecules include radionuclides, fluorescent reporters; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium.

In some embodiments, the payload molecule is a small molecule or a pharmaceutically acceptable salt thereof. A small molecule, as used herein, refers to any molecule that has a molecular weight lower than 900 daltons. Non-limiting examples of small molecules are dexamethasone, corticosteroids (e.g., triamcinolone, prednisolone), TLR inhibitors (e.g., TAK-242, o-vanillin), senolytics (e.g., navitoclax), kinase inhibitors (e.g., SP600125 (JNK1/2 inhibitor), XMD8-92 (ERK-5 inhibitor), JAK3 inhibitors (e.g., CP690550), strontium ranelate, or kartogenin.

(iii) Linkers

The carrier described herein is linked to a payload molecule. In some embodiments, the carrier and the payload molecule are directly linked. In some embodiments, the carrier and the payload molecule are linked by a linker.

A linker, as described herein, refers to a moiety that connects two separate parts together. In some embodiments, the linker is a peptide linker. In some embodiments, the linker between the carrier and the payload molecule is a rigid linker. A rigid linker, as used herein, refers to a linker that is capable of maintaining a fixed distance between the domains and preventing them from moving relative to each other. Non-limiting examples of the rigid linker are $(EAAAK)_3$ (SEQ ID NO: 30), $A(EAAAK)_4ALEA(EAAAK)_4A$ (SEQ ID NO: 31), PAPAP (SEQ ID NO: 33), or AEAAAKEAAAKA (SEQ ID NO: 34). In some embodiments, the rigid linker is $(EAAAK)_3$ (SEQ ID NO: 30) or $A(EAAAK)_4ALEA(EAAAK)_4A$ (SEQ ID NO: 31). In some embodiments, the linker is a flexible linker. A flexible linker, as used herein, refers to a linker that is capable of allowing the two domains to move relative to each other and interact with each other. Exemplary flexible linkers may comprise glycine (G) and/or serine (S) groups. Other amino acids that can be found in flexible linkers include threonine, alanine and sometimes lysine and glutamic acid. Non limiting examples of a flexible linker are $(GGGGS)_4$ (SEQ ID NO: 27), $(GGGGS)_3$ (SEQ ID NO: 28), $(GGS)_9$ (SEQ ID NO: 29), (GGGGS), (SEQ ID NO: 49), wherein n=1-4, KESGSVSSEQLAQFRSLD (SEQ ID NO: 35), EGKSSGSGSESKST (SEQ ID NO: 36), $(Gly)_8$ (SEQ ID NO: 37), $(Gly)_6$ (SEQ ID NO: 38), or GSAGSAAGSGEF (SEQ ID NO: 39). In some embodiments, the flexible linker is $(GGGGS)_4$ (SEQ ID NO: 27), $(GGGGS)_3$ (SEQ ID NO: 28) or $(GGS)_9$ (SEQ ID NO: 29). In some embodiments, the peptide linker is 10-15, 15-20, 20-25, 25-30, 30-35, 35-40, or 40-50 amino acids in length. In some embodiments, the peptide linker is 15-20 amino acids in length. In some embodiments, the peptide linker is 10, 11, 12, 13, 14, 15, 16, 17, 18, 19, or 20 amino acids in length. In some embodiments, the peptide linker may comprise a combination of a flexible linker and a rigid linker.

In some embodiments, the carrier is a +9 S-GFP and the payload molecule is a peptide. In some embodiments, the carrier is a +9 S-GFP and the payload molecule is IGF-1. In some embodiments, the +9 S-GFP is directly linked with IGF-1. An exemplary amino acid sequence for (+9GFP)-(IGF-1) is set forth in SEQ ID NO: 6. In some embodiments, the +9 S-GFP is directly linked with IGF-1 via a flexible linker, such as $(GGGGS)_4$ (SEQ ID NO: 27), $(GGGGS)_3$ (SEQ ID NO: 28) or $(GGS)_9$ (SEQ ID NO: 29). In some embodiments, the +9 S-GFP is linked with IGF-1 via a rigid linker, such as $(EAAAK)_3$ (SEQ ID NO: 30) or $A(EAAAK)_4ALEA(EAAAK)_4A$ (SEQ ID NO: 31). Exemplary amino acid sequences for (+9GFP)-$(GGGGS)_4$-(IGF-1) (SEQ ID NO: 7), (+9GFP)-$(EAAAK)_3$-(IGF-1) (SEQ ID NO: 8), (+9GFP)-$(GGGGS)_3$-(IGF-1) (SEQ ID NO: 9), (+9GFP)-$(GGS)_9$-(IGF-1) (SEQ ID NO: 10), (+9GFP)-(A $(EAAAK)_4ALEA(EAAAK)_4A$)-(IGF-1) (SEQ ID NO: 11) are set forth in SEQ ID NOs: 7 to 11. In some embodiments, a carrier of the present disclosure comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to the amino acid sequence of any one of SEQ ID NOs: 6-11.

In some embodiments, the linker is an enzyme cleavable linker. Non-limiting examples of an enzyme cleavable linker include Val-Clt-PABC linker, glucuronide-MABC linker, pyrophosphate diester linkers, linkers that can be cleaved in the extracellular space such as MMP sensitive linkers, aggrecanase sensitive linkers, VSQTSKLTRAETVFPDV (SEQ ID NO: 40), PLGLWA (SEQ ID NO: 41), RVLAEA (SEQ ID NO: 42), EDVVCCSMSY (SEQ ID NO: 43), GGIEGRGS (SEQ ID NO: 44), TRHRQPRGWE (SEQ ID NO: 45), AGNRVRRSVG (SEQ ID NO: 46), RRRRRRRRR (SEQ ID NO: 47) or GFLG (SEQ ID NO: 48). In some embodiments, the linker is an acid cleavable linker. An acid cleavable linker is normally stable at neutral pH, but can be cleaved in low pH environment (e.g., endosome, lysosome). Non-limiting examples of an acid cleavable linker include Kemp's triacid amide of doxorubicin (DOX), hydrazone linker, or cis-Aconityl linker. Various linkers have been described in the literature. (See, e.g., Chen et al., Advanced Drug Delivery Reviews, *Advanced Drug Delivery Reviews* 65 (2013) 1357-1369; Chichili et al., Linkers in the structural biology of protein—protein interactions, *PROTEIN SCIENCE* 2013 VOL 22:153-167 153; Li et al., Construction of a linker library with widely controllable flexibility for fusion protein design, Appl Microbiol Biotechnol (2016) 100:215-225, the entire contents of which are incorporated herein by reference).

In some embodiments, the carrier is a +15 GFP and the payload molecule is a small molecule (e.g., dexamethasone). In some embodiments, the carrier is a +15 GFP that comprises a cysteine at its N terminus and is linked to a small molecule (e.g., dexamethasone) via a thiol group (SEQ ID NO: 12). In some embodiments, the carrier is a +15 GFP that comprises a cysteine and a flexible peptide linker (e.g., $(GGS)_9$ (SEQ ID NO: 29)) at its N-terminus and is linked to a small molecule (e.g., dexamethasone) (SEQ ID NO: 13). In some embodiments, the +15 GFP is linked to the small molecule (e.g., dexamethasone) via an acid cleavable linker (e.g., hydrazone linker). In some embodiments, the +15 GFP is linked to the small molecule (e.g., dexamethasone) via an enzyme cleavable linker (e.g., pyrophosphate diester linker). In some embodiments, a carrier of the present disclosure comprises an amino acid sequence that is at least 70%, at least 75%, at least 80%, at least 85%, at least 90%, at least 91%, at least 92%, at least 93%, at least 94%, at least 95%, at least 96%, at least 97%, at least 98%, at least 99% or 100% identical to the amino acid sequence of SEQ ID NO: 12 or SEQ ID NO: 13. In some embodiments, the carrier is a +15 GFP that comprises a cysteine at its N terminus (SEQ ID NO: 12) linked to dexamethasone via a hydrazine linker. In some embodiments, the carrier is a +15 GFP that comprises a cysteine at its N terminus (SEQ ID NO: 12) linked to dexamethasone via a pyrophosphate diester linker. In some embodiments, the carrier is a +15 GFP that comprises a cysteine and $(GGS)_9$ (SEQ ID NO: 29) linker at its N-terminus (SEQ ID NO: 13) linked to dexamethasone via a hydrazine linker. In some embodiments, the carrier is a +15 GFP that comprises a cysteine and a $(GGS)_9$ (SEQ ID NO: 29) linker at its N-terminus (SEQ ID NO: 13) linked to dexamethasone via a pyrophosphate diester linker. Exemplary +15 S-GFP-dexamethasone conjugates are depicted in FIGS. 22-25.

An exemplary amino acid sequence of (+9GFP)-(IGF-1) is set forth in SEQ ID NO: 6.

```
                                                (SEQ ID NO: 6)
HHHHHHGGASKGEELFTGVVPILVELDGDVNGHKFSVRGEGEGDATNGKL

TLKFICTTGKLPVPWPTLVTTLTYGVQCFSRYPDHMKRHDFFKSAMPKGY

VQERTISFKKDGKYKTRAEVKFEGRTLVNRIKLKGRDFKEKGNILGHKLR

YNFNSHKVYITADKQKNGIKANFKIRHNVEDGSVQLADHYQQNTPIGDGP

VLLPDNHYLSTQSALSKDPNEKRDHMVLLEFVTAAGITHGMDELYKGPET

LCGAELVDALQFVCGDRGFYFNKPTGYGSSSRRAPQTGIVDECCFRSCDL

RRLEMYCAPLKPAKSA
```

An exemplary amino acid sequence of (+9GFP)-$(GGGGS)_4$-(IGF-1) is set forth in SEQ ID NO: 7.

```
                                                (SEQ ID NO: 7)
HHHHHHGGASKGEELFTGVVPILVELDGDVNGHKFSVRGEGEGDATNGKL

TLKFICTTGKLPVPWPTLVTTLTYGVQCFSRYPDHMKRHDFFKSAMPKGY

VQERTISFKKDGKYKTRAEVKFEGRTLVNRIKLKGRDFKEKGNILGHKLR

YNFNSHKVYITADKQKNGIKANFKIRHNVEDGSVQLADHYQQNTPIGDGP

VLLPDNHYLSTQSALSKDPNEKRDHMVLLEFVTAAGITHGMDELYKGGGG

SGGGGSGGGGSGGGGSGPETLCGAELVDALQFVCGDRGFYFNKPTGYGSS

SRRAPQTGIVDECCFRSCDLRRLEMYCAPLKPAKSA
```

An exemplary amino acid sequence of (+9GFP)-$(EAAAK)_3$-(IGF-1) is set forth in SEQ ID NO: 8.

```
                                                (SEQ ID NO: 8)
HHHHHHGGASKGEELFTGVVPILVELDGDVNGHKFSVRGEGEGDATNGKL

TLKFICTTGKLPVPWPTLVTTLTYGVQCFSRYPDHMKRHDFFKSAMPKGY

VQERTISFKKDGKYKTRAEVKFEGRTLVNRIKLKGRDFKEKGNILGHKLR

YNFNSHKVYITADKQKNGIKANFKIRHNVEDGSVQLADHYQQNTPIGDGP

VLLPDNHYLSTQSALSKDPNEKRDHMVLLEFVTAAGITHGMDELYKEAAA
```

-continued

KEAAAKEAAAKGPETLCGAELVDALQFVCGDRGFYFNKPTGYGSSSRRAP
QTGIVDECCFRSCDLRRLEMYCAPLKPAKSA

An exemplary amino acid sequence of (+9GFP)-$(GGGGS)_3$-(IGF-1) is set forth in SEQ ID NO: 9.

(SEQ ID NO: 9)
HHHHHHGGASKGEELFTGVVPILVELDGDVNGHKFSVRGEGEGDATNGKL
TLKFICTTGKLPVPWPTLVTTLTYGVQCFSRYPDHMKRHDFFKSAMPKGY
VQERTISFKKDGKYKTRAEVKFEGRTLVNRIKLKGRDFKEKGNILGHKLR
YNFNSHKVYITADKQKNGIKANFKIRHNVEDGSVQLADHYQQNTPIGDGP
VLLPDNHYLSTQSALSKDPNEKRDHMVLLEFVTAAGITHGMDELYKGGGG
SGGGGSGGGGSGPETLCGAELVDALQFVCGDRGFYFNKPTGYGSSSRRAP
QTGIVDECCFRSCDLRRLEMYCAPLKPAKSA

An exemplary amino acid sequence of (+9GFP)-$(GGS)_9$-(IGF-1) is set forth in SEQ ID NO: 10.

(SEQ ID NO: 10)
HHHHHHGGASKGEELFTGVVPILVELDGDVNGHKFSVRGEGEGDATNGKL
TLKFICTTGKLPVPWPTLVTTLTYGVQCFSRYPDHMKRHDFFKSAMPKGY
VQERTISFKKDGKYKTRAEVKFEGRTLVNRIKLKGRDFKEKGNILGHKLR
YNFNSHKVYITADKQKNGIKANFKIRHNVEDGSVQLADHYQQNTPIGDGP
VLLPDNHYLSTQSALSKDPNEKRDHMVLLEFVTAAGITHGMDELYKGGSG
GSGGSGGSGGSGGSGGSGGSGGSGPETLCGAELVDALQFVCGDRGFYFNK
PTGYGSSSRRAPQTGIVDECCFRSCDLRRLEMYCAPLKPAKSA

An exemplary amino acid sequence of (+9GFP)-(A$(EAAAK)_4$ALEA$(EAAAK)_4$A)-(IGF-1) is set forth in SEQ ID NO: 11.

(SEQ ID NO: 11)
HHHHHHGGASKGEELFTGVVPILVELDGDVNGHKFSVRGEGEGDATNGKL
TLKFICTTGKLPVPWPTLVTTLTYGVQCFSRYPDHMKRHDFFKSAMPKGY
VQERTISFKKDGKYKTRAEVKFEGRTLVNRIKLKGRDFKEKGNILGHKLR
YNFNSHKVYITADKQKNGIKANFKIRHNVEDGSVQLADHYQQNTPIGDGP
VLLPDNHYLSTQSALSKDPNEKRDHMVLLEFVTAAGITHGMDELYKAEAA
AKEAAAKEAAAKEAAAKALEAEAAAKEAAAKEAAAKEAAAKAGPETLCGA
ELVDALQFVCGDRGFYFNKPTGYGSSSRRAPQTGIVDECCFRSCDLRRLE
MYCAPLKPAKSA

An exemplary amino acid sequence of +15 GFP with a cysteine at its N terminus is set forth in SEQ ID NO: 12.

(SEQ ID NO: 12)
CHHHHHHGGASKGERLFTGVVPILVELDGDVNGHKFSVRGEGEGDATRGKL
TLKFICTTGKLPVPWPTLVTTLTYGVQCFSRYPKHMKRHDFFKSAMPEGYV
QERTISFKKDGTYKTRAEVKFEGRTLVNRIELKGRDFKEKGNILGHKLEYN

-continued

FNSHNVYITADKRKNGIKANFKIRHNVKDGSVQLADHYQQNTPIGRGPVLL
PRNHYLSTRSALSKDPKEKRDHMVLLEFVTAAGITHGMDELYK

An exemplary amino acid sequence of Cysteine-$(GGS)_9$-(+15 GFP) with a cysteine at its N terminus is set forth in SEQ ID NO: 13.

(SEQ ID NO: 13)
CHHHHHHGGSGGSGGSGGSGGSGGSGGSGGSGGSGGASKGERLFTGVVPIL
VELDGDVNGHKFSVRGEGEGDATRGKLTLKFICTTGKLPVPWPTLVTTLTY
GVQCFSRYPKHMKRHDFFKSAMPEGYVQERTISFKKDGTYKTRAEVKFEGR
TLVNRIELKGRDFKEKGNILGHKLEYNFNSHNVYITADKRKNGIKANFKIR
HNVKDGSVQLADHYQQNTPIGRGPVLLPRNHYLSTRSALSKDPKEKRDHMV
LLEFVTAAGITHGMDELYK

An exemplary nucleotide sequence encoding (+9GFP)-(IGF-1) is set forth in SEQ ID NO: 19.

(SEQ ID NO: 19)
CATATGCATCATCATCATCATCATGGCGGTGCGAGCAAGGGCGAAGAACTG
TTTACCGGCGTTGTGCCGATTCTGGTTGAACTGGACGGCGATGTGAACGGC
CACAAGTTCAGCGTTCGTGGTGAGGGCGAAGGTGATGCGACCAACGGCAAG
CTGACCCTGAAATTTATCTGCACCACCGGTAAACTGCCGGTGCCGTGGCCG
ACCCTGGTTACCACCCTGACCTACGGTGTGCAGTGCTTCAGCCGTTATCCG
GACCACATGAAGCGTCACGATTTCTTTAAGAGCGCGATGCCGAAAGGCTAC
GTTCAAGAACGTACCATTAGCTTCAAGAAAGACGGCAAGTATAAAACCCGT
GCGGAAGTGAAATTTGAAGGCCGTACCCTGGTTAACCGTATCAAGCTGAAA
GGTCGTGATTTCAAGGAGAAAGGCAACATTCTGGGTCACAAGCTGCGTTAC
AACTTTAACAGCCACAAAGTGTATATCACCGCGGACAAGCAGAAAAACGGC
ATCAAGGCGAACTTTAAAATTCGTCACAACGTGGAAGACGGTAGCGTTCAA
CTGGCGGATCACTACCAGCAAAACACCCCGATTGGCGACGGTCCGGTTCTG
CTGCCGGATAACCACTATCTGAGCACCCAGAGCGCGCTGAGCAAGGACCCG
AACGAAAAACGTGATCACATGGTGCTGCTGGAGTTCGTTACCGCGGCGGGC
ATCACCCACGGTATGGATGAGCTCTACAAAGGTCCGGAAACCCTGTGCGGT
GCGGAGCTGGTCGACGCGCTGCAGTTTGTTTGCGGCGATCGTGGTTTCTAC
TTTAACAAACCGACCGGCTATGGTAGCAGCAGCCGTCGTGCGCCGCAGACC
GGTATTGTGGACGAGTGCTGCTTCCGTAGCTGCGACCTGCGTCGTCTGGAA
ATGTACTGCGCGCCGCTGAAACCGGCGAAAAGCGCGTAACTCGAG

An exemplary nucleotide sequence encoding +15 GFP with a cysteine at its N terminus is set forth in SEQ ID NO: 20.

(SEQ ID NO: 20)
CATATGTGCCATCATCATCATCATCACGGCGGCGCTAGCAAGGGCGAGCGT
CTGTTTACCGGTGTGGTTCCGATTCTGGTTGAGCTGGACGGCGACGTGAAC
GGCCACAAGTTCAGCGTTCGTGGTGAGGGCGAAGGTGATGCGACCCGTGGC
AAGCTGACCCTGAAATTTATCTGCACCACCGGTAAACTGCCGGTGCCGTGG
CCGACCCTGGTTACCACCCTGACCTACGGTGTGCAGTGCTTCAGCCGTTAT

-continued

CCGAAGCACATGAAACGTCACGACTTCTTTAAGAGCGCGATGCCGGAGGGC

TACGTTCAAGAACGTACCATTAGCTTCAAGAAAGATGGTACCTATAAGACC

CGTGCGGAAGTGAAATTTGAAGGCCGTACCCTGGTTAACCGTATCGAGCTG

AAGGGTCGTGACTTCAAGGAAAAAGGCAACATTCTGGGTCACAAACTGGAG

TACAACTTTAACAGCCACAACGTGTATATCACCGCGGATAAGCGTAAAAAC

GGCATCAAGGCGAACTTTAAAATTCGTCACAACGTGAAGGACGGTAGCGTT

CAGCTGGCGGATCACTACCAGCAAAACACCCCGATTGGTCGTGGTCCGGTG

CTGCTGCCGCGTAACCACTATCTGAGCACCCGTAGCGCGCTGAGCAAAGAC

CCGAAGGAAAAACGTGATCACATGGTTCTGCTGGAGTTTGTGACCGCGGCG

GGCATTACCCACGGCATGGACGAACTGTATAAATAACTCGAG

An exemplary nucleotide sequence encoding (+9GFP)-(IGF-1) is set forth in SEQ ID NO: 21.

(SEQ ID NO: 21)

CATCATCATCATCATCATGGCGGTGCGAGCAAGGGCGAAGAACTGTTTACC

GGCGTTGTGCCGATTCTGGTTGAACTGGACGGCGATGTGAACGGCCACAAG

TTCAGCGTTCGTGGTGAGGGCGAAGGTGATGCGACCAACGGCAAGCTGACC

CTGAAATTTATCTGCACCACCGGTAAACTGCCGGTGCCGTGGCCGACCCTG

GTTACCACCCTGACCTACGGTGTGCAGTGCTTCAGCCGTTATCCGGACCAC

ATGAAGCGTCACGATTTCTTTAAGAGCGCGATGCCGAAAGGCTACGTTCAA

GAACGTACCATTAGCTTCAAGAAAGACGGCAAGTATAAAACCCGTGCGGAA

GTGAAATTTGAAGGCCGTACCCTGGTTAACCGTATCAAGCTGAAAGGTCGT

GATTTCAAGGAGAAAGGCAACATTCTGGGTCACAAGCTGCGTTACAACTTT

AACAGCCACAAAGTGTATATCACCGCGGACAAGCAGAAAAACGGCATCAAG

GCGAACTTTAAAATTCGTCACAACGTGGAAGACGGTAGCGTTCAACTGGCG

GATCACTACCAGCAAAACACCCCGATTGGCGACGGTCCGGTTCTGCTGCCG

GATAACCACTATCTGAGCACCCAGAGCGCGCTGAGCAAGGACCCGAACGAA

AAACGTGATCACATGGTGCTGCTGGAGTTCGTTACCGCGGCGGGCATCACC

CACGGTATGGATGAGCTCTACAAAGGTCCGGAAACCCTGTGCGGTGCGGAG

CTGGTCGACGCGCTGCAGTTTGTTTGCGGCGATCGTGGTTTCTACTTTAAC

AAACCGACCGGCTATGGTAGCAGCAGCCGTCGTGCGCCGCAGACCGGTATT

GTGGACGAGTGCTGCTTCCGTAGCTGCGACCTGCGTCGTCTGGAAATGTAC

TGCGCGCCGCTGAAACCGGCGAAAAGCGCGTAA

An exemplary nucleotide sequence encoding (+9GFP)-$(GGGGS)_4$-(IGF-1) is set forth in SEQ ID NO: 22.

(SEQ ID NO: 22)

CATCATCATCATCATCATGGCGGTGCGAGCAAGGGCGAAGAACTGTTTACC

GGCGTTGTGCCGATTCTGGTTGAACTGGACGGCGATGTGAACGGCCACAAG

TTCAGCGTTCGTGGTGAGGGCGAAGGTGATGCGACCAACGGCAAGCTGACC

CTGAAATTTATCTGCACCACCGGTAAACTGCCGGTGCCGTGGCCGACCCTG

GTTACCACCCTGACCTACGGTGTGCAGTGCTTCAGCCGTTATCCGGACCAC

-continued

ATGAAGCGTCACGATTTCTTTAAGAGCGCGATGCCGAAAGGCTACGTTCAA

GAACGTACCATTAGCTTCAAGAAAGACGGCAAGTATAAAACCCGTGCGGAA

GTGAAATTTGAAGGCCGTACCCTGGTTAACCGTATCAAGCTGAAAGGTCGT

GATTTCAAGGAGAAAGGCAACATTCTGGGTCACAAGCTGCGTTACAACTTT

AACAGCCACAAAGTGTATATCACCGCGGACAAGCAGAAAAACGGCATCAAG

GCGAACTTTAAAATTCGTCACAACGTGGAAGACGGTAGCGTTCAACTGGCG

GATCACTACCAGCAAAACACCCCGATTGGCGACGGTCCGGTTCTGCTGCCG

GATAACCACTATCTGAGCACCCAGAGCGCGCTGAGCAAGGACCCGAACGAA

AAACGTGATCACATGGTGCTGCTGGAGTTCGTTACCGCGGCGGGCATCACC

CACGGTATGGATGAGCTCTACAAGGGTGGCGGTGGCAGCGGTGGCGGTGGC

AGCGGTGGCGGTGGCAGCGGTGGCGGTGGCAGCGGGCCGGAGACCCTGTGC

GGCGCGGAACTGGTCGACGCGCTGCAGTTTGTTTGCGGCGATCGTGGTTTC

TACTTTAACAAACCGACCGGCTATGGTAGCAGCAGCCGTCGTGCGCCGCAG

ACCGGTATTGTGGACGAGTGCTGCTTCCGTAGCTGCGACCTGCGTCGTCTG

GAAATGTACTGCGCGCCGCTGAAACCGGCGAAAAGCGCGTAA

An exemplary nucleotide sequence encoding (+9GFP)-$(GGGGS)_3$-(IGF-1) is set forth in SEQ ID NO: 23.

(SEQ ID NO: 23)

CATCATCATCATCATCATGGCGGTGCGAGCAAGGGCGAAGAACTGTTTACC

GGCGTTGTGCCGATTCTGGTTGAACTGGACGGCGATGTGAACGGCCACAAG

TTCAGCGTTCGTGGTGAGGGCGAAGGTGATGCGACCAACGGCAAGCTGACC

CTGAAATTTATCTGCACCACCGGTAAACTGCCGGTGCCGTGGCCGACCCTG

GTTACCACCCTGACCTACGGTGTGCAGTGCTTCAGCCGTTATCCGGACCAC

ATGAAGCGTCACGATTTCTTTAAGAGCGCGATGCCGAAAGGCTACGTTCAA

GAACGTACCATTAGCTTCAAGAAAGACGGCAAGTATAAAACCCGTGCGGAA

GTGAAATTTGAAGGCCGTACCCTGGTTAACCGTATCAAGCTGAAAGGTCGT

GATTTCAAGGAGAAAGGCAACATTCTGGGTCACAAGCTGCGTTACAACTTT

AACAGCCACAAAGTGTATATCACCGCGGACAAGCAGAAAAACGGCATCAAG

GCGAACTTTAAAATTCGTCACAACGTGGAAGACGGTAGCGTTCAACTGGCG

GATCACTACCAGCAAAACACCCCGATTGGCGACGGTCCGGTTCTGCTGCCG

GATAACCACTATCTGAGCACCCAGAGCGCGCTGAGCAAGGACCCGAACGAA

AAACGTGATCACATGGTGCTGCTGGAGTTCGTTACCGCGGCGGGCATCACC

CACGGTATGGATGAGCTCTACAAGGGTGGCGGTGGCAGCGGTGGCGGTGGC

AGCGGTGGCGGTGGCAGCGGGCCGGAGACCCTGTGCGGCGCGGAACTGGTC

GACGCGCTGCAGTTTGTTTGCGGCGATCGTGGTTTCTACTTTAACAAACCG

ACCGGCTATGGTAGCAGCAGCCGTCGTGCGCCGCAGACCGGTATTGTGGAC

GAGTGCTGCTTCCGTAGCTGCGACCTGCGTCGTCTGGAAATGTACTGCGCG

CCGCTGAAACCGGCGAAAAGCGCGTA

An exemplary nucleotide sequence encoding (+9GFP)-$(GGS)_9$-(IGF-1) is set forth in SEQ ID NO: 24.

(SEQ ID NO: 24)
CATCATCATCATCATCATGGCGGTGCGAGCAAGGGCGAAGAACTGTTTACC
GGCGTTGTGCCGATTCTGGTTGAACTGGACGGCGATGTGAACGGCCACAAG
TTCAGCGTTCGTGGTGAGGGCGAAGGTGATGCGACCAACGGCAAGCTGACC
CTGAAATTTATCTGCACCACCGGTAAACTGCCGGTGCCGTGGCCGACCCTG
GTTACCACCCTGACCTACGGTGTGCAGTGCTTCAGCCGTTATCCGGACCAC
ATGAAGCGTCACGATTTCTTTAAGAGCGCGATGCCGAAAGGCTACGTTCAA
GAACGTACCATTAGCTTCAAGAAAGACGGCAAGTATAAAACCCGTGCGGAA
GTGAAATTTGAAGGCCGTACCCTGGTTAACCGTATCAAGCTGAAAGGTCGT
GATTTCAAGGAGAAAGGCAACATTCTGGGTCACAAGCTGCGTTACAACTTT
AACAGCCACAAAGTGTATATCACCGCGGACAAGCAGAAAAACGGCATCAAG
GCGAACTTTAAAATTCGTCACAACGTGGAAGACGGTAGCGTTCAACTGGCG
GATCACTACCAGCAAAACACCCCGATTGGCGACGGTCCGGTTCTGCTGCCG
GATAACCACTATCTGAGCACCCAGAGCGCGCTGAGCAAGGACCCGAACGAA
AAACGTGATCACATGGTGCTGCTGGAGTTCGTTACCGCGGCGGGCATCACC
CACGGTATGGATGAGCTCTACAAGGGTGGCAGCGGTGGCAGCGGTGGCAGC
GGTGGCAGCGGTGGCAGCGGTGGCAGCGGTGGCAGCGGTGGCAGCGGTGGC
AGCGGGCCGGAGACCCTGTGCGGCGCGGAACTGGTCGACGCGCTGCAGTTT
GTTTGCGGCGATCGTGGTTTCTACTTTAACAAACCGACCGGCTATGGTAGC
AGCAGCCGTCGTGCGCCGCAGACCGGTATTGTGGACGAGTGCTGCTTCCGT
AGCTGCGACCTGCGTCGTCTGGAAATGTACTGCGCGCCGCTGAAACCGGCG
AAAAGCGCGTAA

An exemplary nucleotide sequence encoding (+9GFP)-(EAAAK)$_3$-(IGF-1) is set forth in SEQ ID NO: 25.

(SEQ ID NO: 25)
CATCATCATCATCATCATGGCGGTGCGAGCAAGGGCGAAGAACTGTTTACC
GGCGTTGTGCCGATTCTGGTTGAACTGGACGGCGATGTGAACGGCCACAAG
TTCAGCGTTCGTGGTGAGGGCGAAGGTGATGCGACCAACGGCAAGCTGACC
CTGAAATTTATCTGCACCACCGGTAAACTGCCGGTGCCGTGGCCGACCCTG
GTTACCACCCTGACCTACGGTGTGCAGTGCTTCAGCCGTTATCCGGACCAC
ATGAAGCGTCACGATTTCTTTAAGAGCGCGATGCCGAAAGGCTACGTTCAA
GAACGTACCATTAGCTTCAAGAAAGACGGCAAGTATAAAACCCGTGCGGAA
GTGAAATTTGAAGGCCGTACCCTGGTTAACCGTATCAAGCTGAAAGGTCGT
GATTTCAAGGAGAAAGGCAACATTCTGGGTCACAAGCTGCGTTACAACTTT
AACAGCCACAAAGTGTATATCACCGCGGACAAGCAGAAAAACGGCATCAAG
GCGAACTTTAAAATTCGTCACAACGTGGAAGACGGTAGCGTTCAACTGGCG
GATCACTACCAGCAAAACACCCCGATTGGCGACGGTCCGGTTCTGCTGCCG
GATAACCACTATCTGAGCACCCAGAGCGCGCTGAGCAAGGACCCGAACGAA
AAACGTGATCACATGGTGCTGCTGGAGTTCGTTACCGCGGCGGGCATCACC
CACGGTATGGATGAGCTCTACAAAGAGGCGGCGGCGAAAGAAGCGGCGGCG
AAAGAGGCGGCGGCGAAGGGTCCGGAAACCCTGTGCGGCGCGGAGCTGGTC

-continued
GACGCGCTGCAGTTTGTTTGCGGCGATCGTGGTTTCTACTTTAACAAACCG
ACCGGCTATGGTAGCAGCAGCCGTCGTGCGCCGCAGACCGGTATTGTGGAC
GAGTGCTGCTTCCGTAGCTGCGACCTGCGTCGTCTGGAAATGTACTGCGCG
CCGCTGAAACCGGCGAAAAGCGCGTAA An exemplary nucleotide sequence encoding (+9GFP)-(A(EAAAK)$_4$ALEA(EAAAK)$_4$A)-IGF-1 is set forth in SEQ ID NO: 26.

(SEQ ID NO: 26)
CATCATCATCATCATCATGGCGGTGCGAGCAAGGGCGAAGAACTGTTTACC
GGCGTTGTGCCGATTCTGGTTGAACTGGACGGCGATGTGAACGGCCACAAG
TTCAGCGTTCGTGGTGAGGGCGAAGGTGATGCGACCAACGGCAAGCTGACC
CTGAAATTTATCTGCACCACCGGTAAACTGCCGGTGCCGTGGCCGACCCTG
GTTACCACCCTGACCTACGGTGTGCAGTGCTTCAGCCGTTATCCGGACCAC
ATGAAGCGTCACGATTTCTTTAAGAGCGCGATGCCGAAAGGCTACGTTCAA
GAACGTACCATTAGCTTCAAGAAAGACGGCAAGTATAAAACCCGTGCGGAA
GTGAAATTTGAAGGCCGTACCCTGGTTAACCGTATCAAGCTGAAAGGTCGT
GATTTCAAGGAGAAAGGCAACATTCTGGGTCACAAGCTGCGTTACAACTTT
AACAGCCACAAAGTGTATATCACCGCGGACAAGCAGAAAAACGGCATCAAG
GCGAACTTTAAAATTCGTCACAACGTGGAAGACGGTAGCGTTCAACTGGCG
GATCACTACCAGCAAAACACCCCGATTGGCGACGGTCCGGTTCTGCTGCCG
GATAACCACTATCTGAGCACCCAGAGCGCGCTGAGCAAGGACCCGAACGAA
AAACGTGATCACATGGTGCTGCTGGAGTTCGTTACCGCGGCGGGCATCACC
CACGGTATGGATGAGCTCTACAAAGCGGAGGCGGCTGCGAAGGAAGCGGCG
GCGAAAGAGGCGGCTGCTAAGGAAGCGGCGGCGAAGGCGCTGGAGGCGGAG
GCTGCTGCGAAAGAGGCGGCGGCGAAAGAAGCGGCTGCTAAAGAGGCGGCG
GCGAAGGCGGGTCCGGAAACCCTGTGCGGCGCGGAGCTGGTCGACGCGCTG
CAGTTTGTTTGCGGCGATCGTGGTTTCTACTTTAACAAACCGACCGGCTAT
GGTAGCAGCAGCCGTCGTGCGCCGCAGACCGGTATTGTGGACGAGTGCTGC
TTCCGTAGCTGCGACCTGCGTCGTCTGGAAATGTACTGCGCGCCGCTGAAA
CCGGCGAAAAGCGCGTAA

The linker described herein can be cleaved once the carrier reaches the target tissue. The cleavage of the linker results in the release of the payload molecule in a sustained matter over a long period of time.

The choice of the carrier, linker, and the payload molecule can be designed based on the target tissue, intended function, size of the carrier and the payload molecule. The carrier of the present disclosure enables delivering payload molecule to multiple target tissues (e.g., avascular tissue and/or partially vascularized tissue), fine tuning the level and tissue penetration depth, and sustained release of the payload molecule.

Also provided herein by the present disclosure are nucleic acid sequences and vectors encoding the carriers and the payload molecule linked carrier. Exemplary nucleic acid sequence encoding the carriers and/or payload are set forth in SEQ ID NOs: 14 to 26. The coding sequences for the carriers and/or payloads described herein are at least 70%, at least 75%, at least 80%, at least 85%, at least 90%, at least 91%, at least 92%, at least 93%, at least 94%, at least 95%, at least 96%, at least 97%, at least 98%, at least 99% or 100% identical to the nucleic acid sequences of SEQ ID NOs: 14-26.

II. Pharmaceutical Compositions

In some aspects, the present disclosure, at least in part, relates to a composition, comprising the carrier described herein, linked to a payload molecule described herein. The pharmaceutical composition described herein may further comprise a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used for in vivo administration must be sterile. This is readily accomplished by, for example, filtration through sterile filtration membranes. The payload molecule linked carrier containing compositions may be placed into a container having a sterile access port, for example, an intravenous solution bag or vial having a stopper pierceable by a hypodermic injection needle.

In some embodiments, the pharmaceutical composition to be used herein, can be formulated for local injection of a payload molecule linked carrier (e.g. S-GFP-IGF1). A high concentration of composition can be achieved in situ, while using small amounts of drugs. Local delivery of immunotherapies allows multiple combination therapies, while preventing significant systemic exposure and off-target toxicities.

In other embodiments, the pharmaceutical composition can be formulated for intra-muscular injection, intravenous injection, or subcutaneous injection.

The pharmaceutical compositions to be used in the present methods can comprise pharmaceutically acceptable carriers, buffer agents, excipients, salts, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some examples, the pharmaceutical composition described herein comprises lipid nanoparticles which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

In other examples, the pharmaceutical composition described herein can be formulated in a sustained-release format. Suitable examples of sustained-release preparations include semipermeable matrices of solid hydrophobic polymers containing a payload molecule linked carrier (e.g. S-GFP-IGF1), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

Suitable surface-active agents include, in particular, non-ionic agents, such as polyoxyethylenesorbitans (e.g., TWEEN™ 20, 40, 60, 80 or 85) and other sorbitans (e.g., SPAN™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets having a suitable size and can have a pH in the range of 5.5 to 8.0.

Pharmaceutical compositions for inhalation or insufflation for local delivery to nasal cartilage and/or trachea cartilage include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

III. Applications

The compositions disclosed herein, comprising a carrier described herein, linked to a payload molecule described herein, can be used to treat a target disease or disorder.

The subject to be treated by the methods described herein can be a mammal, such as a human, farm animals, sport animals, pets, primates, horses, dogs, cats, mice and rats. In one embodiment, the subject is a human. The payload molecule linked carrier (e.g. S-GFP-IGF1) containing composition as described herein may be used for delivery of the payload molecule to an avascular tissue, for example, joint cartilage, in a subject in need of the treatment.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

The compositions of the invention are useful for treating a target disease or disorder. Non-limiting examples of target diseases or disorders are a joint disease, pseudogout, orphan disease, a genetic disorder, an autoimmune disorder, or a cancer. In some embodiments, the joint disease is osteoarthritis, intervertebral disc degeneration or a musculoskeletal disease. In some embodiments, the target disease is a genetic disorder (e.g., chondrodysplasia, or mucopolysaccharidosis). In other embodiments, the target disease is an autoimmune disorder (e.g., relapsing polychondritis).

In some embodiments the musculoskeletal disease is osteoarthritis (OA) or osteoporosis. Osteoporosis is a common disorder resulting in a reduction in bone mass. OA is one of the most common chronic illnesses affecting over 150 million people worldwide, making it one of the most prevalent diseases in the world (WHO, 2009). OA attacks body joints, affecting productivity and quality of life, and is extremely disabling to the patient. While great advances have been made in developing drugs for rheumatoid arthritis (RA), there is no disease modifying drug available for OA.

In some embodiments, the method of treating a disease includes combining two or more different carrier linked with payload molecules. In some embodiments, the target disease is a joint disease (e.g., osteoarthritis), and the combination of carriers to be used is a first carrier linked with a pro-anabolic protein and/or a second carrier linked with an anti-catabolic and/or anti-inflammatory small molecule. A pro-anabolic protein, as used herein, refers to a protein that stimulates cells to produce other proteins, proteoglycans, glyocproteins and other extracellular matrix components, such as growth factors (e.g., IGF-1). A anti-catabolic and/or anti-inflammatory small molecule, as used herein, refers to small molecules with optional anti-inflammatory properties that prevent the breakdown of the extracellular matrix in tissues and decrease the levels of inflammatory factors (e.g., dexamethasone). In some embodiments, the combination is a +9 super charged green fluorescent protein (+9 S-GFP) linked with an IGF-1 and a +15 super charged green fluorescent protein (+15 S-GFP) linked with a dexamethasone. There is no limit of how many carriers can be combined to treat a certain target disease.

To practice the method disclosed herein, an effective amount of any of the pharmaceutical compositions described herein can be administered to a subject (e.g., a human) in need of the treatment via a suitable route, such as local administration, intratumoral administration, by intravenous administration, e.g., as a bolus or by continuous infusion over a period of time, by local, intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, a payload molecule linked carrier (e.g. S-GFP-IGF1) containing pharmaceutical composition can be aerosolized using a fluorocarbon formulation and a metered dose inhaler, or inhaled as a lyophilized and milled powder. In some examples, the pharmaceutical composition described herein is formulated for intratumoral injection. In particular examples, the pharmaceutical composition may be administered to a subject (e.g., a human patient) via a local route, for example, injected to a local site such as a joint.

As used herein, "an effective amount" refers to the amount of each active agent required to confer therapeutic effect on the subject, either alone or in combination with one or more other active agents. In some embodiments, the therapeutic effect is reduced tumor burden, reduction of cancer cells, or increased immune activity. Determination of whether an amount of payload molecule linked carrier (e.g. S-GFP-IGF1) achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a payload molecule linked carrier (e.g. S-GFP-IGF1) may be appropriate. Various formulations and devices for achieving sustained release are known in the art.

In some embodiments, the treatment is a single injection of the payload molecule linked carrier (e.g. S-GFP-IGF1) containing pharmaceutical composition. In some embodiments, the single injection is administered locally to the subject in need thereof.

In some example, dosages for a payload molecule linked carrier (e.g. S-GFP-IGF1) as described herein may be determined empirically in individuals who have been given one or more administration(s) of synthetic oncolytic. Individuals are given incremental dosages of the synthetic oncolytic containing composition. To assess efficacy of the payload molecule linked carrier (e.g. S-GFP-IGF1), an indicator of the disease/disorder can be followed. For repeated administrations over several days or longer, depending on the condition, the treatment is sustained until a desired suppression of symptoms occurs or until sufficient therapeutic levels are achieved to alleviate a target disease or disorder, or a symptom thereof.

In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen of the payload molecule linked carrier (e.g. S-GFP-IGF1) used can vary over time.

In some embodiments, the method described herein comprises administering to a subject in need of the treatment (e.g., a human patient) one or multiple doses of a payload molecule linked carrier (e.g. S-GFP-IGF1) containing pharmaceutical composition.

For the purpose of the present disclosure, the appropriate dosage payload molecule linked carrier (e.g. S-GFP-IGF1) as described herein will depend on the specific s payload molecule linked carrier, the type and severity of the disease/disorder, the payload molecule linked carrier (e.g. S-GFP-IGF1) is administered for preventive or therapeutic purposes, previous therapy, the patient's clinical history and response to the payload molecule linked carrier (e.g. S-GFP-IGF1), and the discretion of the attending physician. A clinician may administer a payload molecule linked carrier (e.g. S-GFP-IGF1), until a dosage is reached that achieves the desired result. In some embodiments, the desired result is a decrease in tumor burden, a decrease in cancer cells, or increased immune activity. Methods of determining whether a dosage resulted in the desired result would be evident to one of skill in the art. Administration of one or more payload molecule linked carrier (e.g. S-GFP-IGF1) can be continuous or intermittent, depending, for example, upon the recipient's physiological condition, whether the purpose of the administration is therapeutic or prophylactic, and other factors known to skilled practitioners. The administration of the payload molecule linked carrier (e.g. S-GFP-IGF1) may be essentially continuous over a preselected period of time or may be in a series of spaced doses, e.g., either before, during, or after developing a target disease or disorder.

IV. General Techniques

The practice of the present invention will employ, unless otherwise indicated, conventional techniques of molecular biology (including recombinant techniques), microbiology, cell biology, biochemistry and immunology, which are within the skill of the art. Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Green Fluorescent Proteins Engineered for Cartilage-Targeted Drug Delivery: Insights for Transport into Highly Charged Avascular Tissues

Materials and Methods

Structure and Preparation of Cationic and Neutral GFP Variants

Cationic S-GFPs: BL21 Star (DE3)-competent *E. coli* cells were transformed with plasmids encoding the supercharged GFPs with a His6 N-terminal purification tag. A single colony was grown overnight in Luria-Bertani (LB) broth containing 50 mg/mL chloramphenicol at 37° C. The cells were diluted 1:100 into 1 L of the same media and grown at 37° C. until OD600 0.6-0.7. The cultures were incubated on ice for 60 min before induction of protein expression with 0.5 mM isopropyl-β-D-1-thiogalactopyranoside (IPTG) (GoldBio). Expression was sustained for 15 h with shaking at 16° C. Cells were collected by centrifugation at 6,000 g for 20 min (4° C.) and re-suspended in cell collection buffer (100 mM tris(hydroxymethyl)-aminomethane (Tris)-HCl, pH 8.0, 1 M NaCl, 20% glycerol, 5 mM tris(2-carboxyethyl)phosphine (TCEP; GoldBio), 0.4 mM phenylmethane sulfonyl fluoride (SigmaAldrich) and 1 complete, EDTA-free protease inhibitor pellet (Roche) per 50 mL buffer used). Cells were lysed by sonication (5 min total, 3s on, 5 s off) and the lysate cleared by centrifugation at 22,500 g (25 min). The cleared lysate was incubated with His-Pur nickel nitriloacetic acid (nickel-NTA) resin (1.5 mL resin per litre of culture, Thermo Fisher) with rotation at 4° C. for 60 min. The resin was washed with 20 column volumes of cell collection buffer before bound protein was eluted with elution buffer ((100 mM tris(hydroxymethyl)-aminomethane (Tris)HCl, pH 8.0, 0.5 M NaCl, 20% glycerol, 5 mM TCEP (GoldBio), 200 mM imidazole). The resulting protein fraction was further purified on a 5 mL Hi-Trap HP SP (GE Healthcare) cation exchange column using an Akta Pure FPLC. An NaCl gradient (from 0 to 1 M) was used to elute the supercharged GFP from the HP SP column; the NaCl concentration required to elute the S-GFP increased with an increase in protein charge.

Protein-containing fractions were concentrated using a column with a 10 kDa cutoff (Millipore) centrifuged at 3,000 g, and the concentrated solution was sterile-filtered through a 22-mm polyvinylidene difluoride (PVDF) membrane (Millipore). After concentration, proteins were resuspended in storage buffer (100 mM tris(hydroxymethyl)-amino-methane (Tris)-HCl, pH 8.0, 0.5 M NaCl, 20% glycerol, 5 mM TCEP (GoldBio)). After sterile filtration, proteins were quantified with Reducing Agent Compatible Bicinchoninic acid assay (Pierce Biotechnology), snap-frozen in liquid nitrogen and stored in aliquots at 80° C.

Neutral GFPs: BL21(DE3) cells were transformed with plasmids encoding the neutral GFP variants. For each variant, a well-isolated colony was grown overnight in LB broth containing kanamycin at 37° C. 5 mL of the overnight culture was diluted in 1 L of LB broth and incubated at 37° C. until OD600 0.8-1. Cultures were then induced with 1 mM IPTG, grown for 20 h at 37° C., and harvested. Cells were collected by centrifugation at 4700 rpm for 15 min and stored at −80° C. The frozen cells were homogeneously resuspended in lysis buffer including 10 mM imidazole and then sonicated in an ice bath for 10 min. The resulting cell debris and the supernatant were separated by centrifugation at 13000 rpm (4° C.) for 30 min. The presence of the expressed protein in the supernatant was confirmed by SDS-PAGE. The collected protein was purified using Ni-NTA metal affinity chromatography and was fully eluted using 250 mM imidazole. Elution fractions containing purified protein were dialyzed into 20 mM Tris-C1, 300 mM NaCl, pH 8.0. The purified proteins were analyzed in SDS-PAGE gel, quantified using a NanoDrop instrument, sterile-filtered through a 22-mm PVDF membrane and stored at −80° C.

Bovine Cartilage Explant and Chondrocyte Harvest

Cartilage tissue was harvested from the femoropatellar grooves of 11 knee joints from 11 different freshly slaughtered 1-2 week old bovine calves (Research 87, Boylston MA) as previously described. Cylindrical cartilage disks (3 mm in diameter) that included the intact superficial zone were cut out and washed with Dulbecco's phosphate buffered saline without calcium and magnesium (PBS). They were then trimmed down to 1 mm thick explants and equilibrated for 48 h at 37° C. and 5% CO2 in serum-free medium (Low glucose (1 g/L) Dulbecco's Modified Eagle's medium (DMEM), 100 U/mL penicillin, 100 mg/mL streptomycin, 0.25 mg/mL amphotericin, 10 mM HEPES buffer, 0.1 mM nonessential amino acids (NEAA), 0.4 mM proline and 20 mg/mL ascorbic acid).

To extract live chondrocytes, cartilage tissue slices were first harvested from the femoral condyles of bovine joints. Solutions of collagenase (1.25 mg/mL) and pronase (2 mg/mL) were prepared in low glucose DMEM with 5% fetal bovine serum (FBS), 100 U/mL penicillin, 100 mg/mL streptomycin, 0.25 mg/mL amphotericin, 10 mM HEPES buffer, 0.1 mM nonessential amino acids (NEAA) and 0.4 mM proline. After washing with PBS, cartilage slices were first incubated in the pronase solution for 1 h followed by overnight incubation in the collagenase solution at 37° C. and 5% CO2. The final solution was then passed through a 70 μm filter and a 40 μm filter to remove any undigested cartilage fragments. The filtrate was centrifuged at 400 g for 8 min and the pellet was resuspended in 50 mL PBS. Viable cell counts were obtained from aliquots of this suspension using a hemocytometer and Trypan blue. The cells were then centrifuged out of the suspension (400 g, 8 min), resuspended in freezing medium (FBS with 5% DMSO) and stored in liquid nitrogen until use.

Human Cartilage Explant Harvest

Two human knee joint distal femurs were obtained through the Gift of Hope Organ and Tissue Donor Network (Itaska, IL). A Collins grade 0 normal knee was from a 36 year male donor and a near-normal grade 1 from a 35 year female. (The Collins visual grading scale grades spans grades 0-4 [20], with grade 0=normal and grade 4=end stage osteoarthritis.) All procedures were approved by the Rush University Medical Center Institutional Review Board (ORA Number: 08082803IRB01-AM01) and the Committee on the Use of Humans as Experimental Subjects at MIT.

Femoral cartilage plugs (3 mm diameter) were harvested using a biopsy punch, trimmed down to 1 mm thickness and equilibrated for 48 h (37° C., 5% CO2) in high glucose (4.5 g/L) DMEM which was supplemented with 100 U/mL penicillin, 100 mg/mL streptomycin, 0.25 mg/mL amphotericin, 10 mM HEPES buffer, 0.1 mM nonessential amino acids (NEAA), 0.4 mM proline and 20 mg/mL ascorbic acid.

Bovine Synovial Fluid

Bovine synovial fluid (BSF) was procured from Lampire Biological Laboratories (Pipersville, PA). BSF was collected using sterile syringes from the carpal joints of adult cows within 1 h of slaughter, pooled and delivered at 10° C. within two days of collection. Some aliquots of BSF were kept frozen at −20° C. (for short-term storage) and the rest were stored at −80° C.

Quantitative Uptake of GFPs into Cartilage

Experiments to quantify the uptake of GFPs into cartilage were started after the explants had been pre-equilibrated in culture medium for 48 h post-harvest. Sterile PBS solutions containing 1% bovine serum albumin (BSA) along with 1 μM concentration of each of the four S-GFP variants (+36, +25, +15 and +9) and the three neutral GFP variants (Janus, NP and HP) were prepared. The BSA was included in the PBS to minimize loss of GFPs in the solution caused by non-specific binding to the plasticware. Since the main function of the albumin in these experiments was to prevent such non-specific binding in the external solution, independent of tissue species, BSA was used for the bovine cartilage as well as the human cartilage experiments (as opposed to BSA with bovine cartilage and human serum albumin (HSA) with human cartilage) to maintain consistency in experimental techniques. Groups of 5 cartilage explants (matched for position along the joint surface) were washed with PBS, and each explant was separately incubated in 250 μL of the GFP solutions in sterile polypropylene vials for 24 h or for 8 days (37° C., 5% CO2). (Standard 96-well cell culture plates were not used because S-GFPs could stick to polystyrene even in the presence of BSA, leading to a loss of protein. In contrast, use of polypropylene with 1% BSA enabled complete recovery of fluorescence). In addition, uptake of the cationic S-GFPs into cartilage explants was also performed in solutions of bovine synovial fluid. On the day of the experiment, BSF was thawed and warmed in a 37° C. water bath with periodic, gentle agitation. At the end of the incubation period in either PBS or BSF, cartilage explants were washed with PBS and transferred to a solution of 10×PBS+1% BSA for desorption. At the same time, the fluorescence of the absorption bath was measured using a plate reader (Synergy H1, Biotek Instruments Inc.) (excitation: 485 nm, emission: 528 nm). This was used along with a standard curve to obtain the concentration of GFP left behind in the absorption bath. At the end of the desorption in 10×PBS+1% BSA, cartilage explants were weighed and the fluorescence of the desorption bath was measured. This fluorescence measurement was used with a standard curve and the explant wet weights to calculate the concentration of GFP inside cartilage explants (mol/mg wet weight). The uptake ratio was calculated as the ratio of GFP concentration inside cartilage (mol/mg wet weight) to the final absorption bath concentration (mol/mL).

GFP Penetration into Cartilage and Chondrocytes

Bovine cartilage explants were incubated for either 24 h or 8 days (37° C., 5% CO2) in 1 μM solutions of the cationic S-GFPs dissolved in PBS+1% BSA. Similarly, explants were placed in 1 μM solutions of the neutral GFPs for either 18 h or 26 h. In a separate series of experiments, bovine cartilage explants were cultured in ultra-low attachment cell culture plates (Corning) for a period of 8 days in 1 μM solutions of cationic S-GFPs dissolved in low glucose (1 g/L) DMEM (with no phenol red) with 10% fetal bovine serum (FBS) supplemented with 2 mM Lglutamine, 100 U/mL penicillin, 100 mg/mL streptomycin, 0.25 mg/mL amphotericin, 10 mM HEPES buffer, 0.1 mM nonessential amino acids (NEAA) and 0.4 mM proline (37° C., 5% CO2). Media changes were performed every 48 h, and fresh cationic S-GFP were added with each media change. At the end of all such experiments, explants were sectioned longitudinally into 100 m slices and washed with PBS. Primary bovine chondrocytes were incubated for 24 h (37° C., 5% CO2) in 100 nM solutions of GFPs dissolved in serum-free medium having the same composition as that described in the bovine cartilage harvest section. At the end of 24 h, chondrocytes were washed three times with heparin dissolved in PBS (20 U/mL) to remove non-internalized GFPs, fixed with 4% paraformaldehyde, stained with DAPI and washed with PBS.

Explant slices and fixed chondrocytes were imaged at 10× magnification using a confocal microscope (Olympus FluoView FV1000), and Z-stacks were obtained with a voxel depth of 4.22 μm for cartilage and 1.16 μm for chondrocytes. 3D cartilage Z-stacks were flattened to 2D using the Z project function available in the Fiji software package. During imaging, some cartilage explants were too large to fit into the field of view of the confocal microscope. In these cases, two overlapping Z-stacks were captured and combined using the Stitching plugin available in Fiji before performing 2D Z projections. For chondrocyte Z-stacks, the slice in which the cell images were the sharpest (best focus) were used.

Effect of Charge on the Uptake and Transport of Cationic Carriers into Cartilage 10 nM, 100 nM and 1 μM solutions of each of the cationic S-GFP variants were prepared in low glucose (1 g/L) DMEM supplemented with 10% FBS, 100 U/mL penicillin, 100 mg/mL streptomycin, 0.25 mg/mL amphotericin, 10 mM HEPES buffer, 0.1 mM NEAA, 0.4 mM proline and 20 mg/mL ascorbic acid. Groups of 5 bovine cartilage explants were incubated in these solutions in ultra low attachment cell culture plates (Corning) at 37° C., 5% CO2. Untreated controls consisted of groups of 5 explants incubated in medium without any GFPs. Medium changes were carried out every 48 h for the 8-day duration of the experiment. Treatment groups received fresh GFP doses with each medium change. Explant viability by day 8 was measured using the Alamar Blue assay (ThermoFisher). Cartilage explants were incubated for 2.5 h in a 1× solution of Alamar Blue dissolved in culture medium. Absorbance measurements at 570 nm and 600 nm were performed using a microplate reader (Synergy H1 Hybrid Multi-Mode Microplate Reader, BioTek) and used to calculate the percentage reduction of Alamar Blue, which is directly proportional to the explant viability. These values were normalized by explant weights. These weight-normalized readings for the treatment groups were then normalized by the weight-normalized mean value for the untreated controls. To measure chondrocyte biosynthesis rates, explants were cultured in the presence of 5 μCi/mL 35S-sulfate radiolabel between days 6 and 8 of culture, and the rate of incorporation of radioactive sulfate into sulfated glycosaminoglycans (sGAGs) was measured. At the end of the experiment, all explants were washed with PBS with non-radioactive sulfate to wash out excess radiolabel, weighed and digested with proteinase K. A liquid scintillation counter (PerkinElmer) was used to measure the amount of radiolabel incorporated within the explant extracellular matrix. Radiolabel incorporation was normalized by the duration of exposure to radiolabel (48 h) and by the DNA content of the explants (measured using the Hoechst 33258 dye binding assay).

To calculate the cumulative loss of GAGs from the explant that may have been caused by the 8-day culture with various cationic S-GFPs, the amount of sGAG lost to the medium and that left behind in the explants at the end of the experiment was measured using the dimethylene blue (DMMB) dye binding assay.

Dynamic Uptake: Transport Experiments and Theory

To measure the kinetics of the uptake of cationic S-GFPs into cartilage, dynamic uptake experiments were performed. Cartilage disks (6 mm diameter) were clamped to one end of a transport chamber in such a way that one face was in contact with an impermeable wall and the other face had a circular area with a 4 mm diameter exposed to a well-mixed bath (see Results). The initial bath was a 1×PBS+1% BSA solution (total volume 2 mL). At time zero, +9 S-GFP was added to the bath, and the bath concentration was monitored continuously through fluorescence measurements. A mathematical diffusion-reaction model was formulated and used to predict the changes in bath concentration of +9 S-GFP upon transport into the cartilage explant disks. Diffusion-reaction parameters obtained from the fit were then used in the model to predict the numerical values of the final uptake ratios obtained experimentally at 24 h and 8 days.

Statistical Analysis

Statistical analysis was carried out using MATLAB R2015a software. All quantitative data are plotted as Mean±95% Confidence Interval. Mean values and standard deviations are also reported in tables in the supplementary material. Depending on the experiment, one-way or two way ANOVAs were also performed followed by the post-hoc Tukey's HSD test; p-values less than 0.05 were considered statistically significant.

Results

All cationic supercharged GFPs used in this study were very similar in size and also had high purity. These GFPs were therefore used to investigate the effect of cationic charge on transport into cartilage tissue independent of any other factors that may affect transport properties. Neutral GFPs with varying surface charge distributions were used as controls for net charge and to further test whether the surface charge distribution and charge patch size of net-neutral GFPs might affect cartilage penetration.

Effect of Charge on the Uptake and Transport of Cationic Carriers into Cartilage Cationic S-GFPs were dissolved in either PBS+1% BSA or bovine synovial fluid (BSF) and their uptake ratios were quantified in bovine cartilage tissue after 24 h and 8 day incubations. All the cationic S-GFP variants showed enhanced uptake into cartilage and in every condition tested, the lower charged variants had a significantly higher uptake ratio compared to the higher charged variants. Additionally, it was observed that the uptake of the cationic SGFPs from PBS+1% BSA was higher than their uptake from BSF. Finally, the uptake ratios of S-GFPs at the 8 day time point were higher than their uptake ratios at 24 h.

The higher uptake ratios of cationic S-GFPs at 8 days compared to 24 h indicated that transport into the cartilage explants had not reached equilibrium in the first 24 h, i.e., that the GFPs had not penetrated through the full thickness of the cartilage explants within 24 h. To visualize the extent of penetration, bovine cartilage explants that were incubated for 24 h in culture medium with 1 μM concentrations of the cationic S-GFPs were sliced longitudinally and imaged using confocal microscopy. +9 S-GFP penetrated the full 1 mm thickness of cartilage in 24 h while the extent of penetration decreased as the cationic charge of the GFP variant increased. Similar experiments were performed with continuous doses of cationic S-GFPs that were replenished every 48 h over an 8 day period and the extent of tissue penetration was visualized every 24 h from Day 1 to Day 8.

Effect of Surface Charge Distribution on Uptake of Net Neutral GFPs into Cartilage Uptake ratios of the three neutral GFPs into bovine cartilage after a 24 h incubation in solutions of the GFPs in 1×PBS+1% BSA (37° C. and 5% CO2) was measured. Two of the three neutral variants had an uptake ratio of 1, i.e., the concentration inside the cartilage is the same as that in the bath, and there is no enhanced uptake. However, at the same 24-h time point, Janus GFP showed an enhanced uptake ratio of 10.1±1.3. The 24 h uptake ratios of each of the cationic S-GFPs from PBS+1% BSA were at approximately the same level or higher than that of the Janus GFPs, with the highest uptake ratio at approximately 25 for the +9 S-GFP at the same conditions.

Following the 24 h incubation in GFP solutions, cartilage explants were transferred to either [1×PBS+1% BSA] or [10×PBS+1% BSA] solutions for an additional 48 h, and the percentage of GFP inside the explants that was desorbed was measured.

Uptake of Cationic S-GFPs into Human Cartilage

Tissue from the 35 year old female donor knee was used to obtain the 24 h and 8 day uptake ratios of cationic S-GFPs dissolved in PBS+1% BSA. The results were consistent with those obtained using bovine tissue in that the uptake ratios increased as the cationic S-GFP charge decreased and the 8 day uptake ratios were much higher than the 24 h uptake ratios. Tissue from the 36 year old male donor was used to obtain the 24 h uptake ratios of cationic S-GFPs dissolved either in PBS+1% BSA or in BSF. Similar to bovine cartilage, the uptake from PBS+1% BSA was higher than the uptake from BSF, and the uptake ratios of +36 and +25 GFPs were significantly lower compared to the other two GFP variants. However, unlike bovine cartilage, +15 GFP (and not +9) had the highest uptake ratio. The difference in the uptake ratios of +15 and +9 GFPs was statistically significant in the case of uptake from BSF, but not in the case of PBS+1% BSA.

Chondrocyte Uptake of Cationic S-GFPs Increases with Net Charge

Primary bovine chondrocytes were harvested and incubated in solutions of 100 nM cationic S-GFPs dissolved in culture medium. Control cells were incubated in medium with no GFPs. Confocal microscopy, performed with fixed settings for fluorescence imaging, revealed that the cellular uptake of cationic S-GFPs into chondrocytes increased significantly with increasing net charge. These results are consistent with trends observed in other cell types such as HeLa cells (Thompson et al. Chem. Biol. 19(7):831-843 (2012).

In a separate experiment, the cellular uptake of the three neutral GFP variants was tested using the same method (24 h incubation in 100 nM solutions followed by fixation and confocal microscopy with fixed settings). In this experiment, a negative control with no GFPs and a positive control with +9 GFP was included. The results demonstrate that the cellular uptake of the neutral GFPs is much lower compared to that of +9 GFP.

The possible outcome that higher cationic charged GFPs could be taken up by chondrocytes within native cartilage tissue was also tested. To visualize the extent of intracellular uptake of S-GFPs, bovine cartilage explants that were incubated for 24 h or 8 days in solutions of either +36 or +9 GFP in PBS+1% BSA were sliced longitudinally and imaged using confocal microscopy. The +9 GFP penetrated the full 1 mm thickness of cartilage in 24 h while +36 GFP did not. However, by day 8, +36 GFPs were found to be localized primarily inside chondrocytes throughout the tissue thickness while the +9 GFPs were found in the extracellular matrix (ECM) of the explant, but not within the cells. Thus, the trend of cell uptake versus net cationic charge found within intact cartilage explants was similar to that found with isolated cells.

Effect of Cationic S-GFPs on Cartilage Matrix sGAG Loss, Chondrocyte Biosynthesis Rates and Cell Viability in Native Cartilage Tissue Bovine cartilage explants were treated with 1 μM, 100 nM and 10 nM doses of each of the four cationic S-GFP variants used in this study. An untreated control group was also included. 10 nM and 100 nM doses of cationic S-GFPs did not lead to any changes in the DNA content, cell viability, aggrecan biosynthesis as a measure of cell metabolic activity, or sGAG release from explant. At 1 μM doses, there was a statistically significant but modest increase in the sGAG loss from explants and a statistically significant decrease in their biosynthesis rate. But these doses did not lead to significant changes in DNA content or cell viability.

Theoretical Model of Dynamic Uptake of +9 S-GFP into Human and Bovine Cartilage

Dynamic uptake of +9 GFP into both human and bovine cartilage (the former from the 35 year old female donor knee) was measured. As the GFP entered the cartilage explants, the bath concentration was measured continuously using real-time fluorescence detection, and observed to decrease with time over a 48 h period. A mathematical model that included the effects of diffusion and charge-based partitioning and binding was developed for the transport of GFPs from the bath into cartilage tissue (equations 17 to 22). The diffusivity of +9 GFP (Table 1) was estimated based on the empirical power law model formulated for cartilage transport (DiDomenico et al. Annual Meeting of the Orthopaedic Research Society, New Orleans, L A, 2018 Abstract No. 2121), accounting for solute hydrodynamic radius and steric interactions within cartilage extracellular matrix, but not charge. The positive charge of the GFP will lead to a high Donnan partitioning coefficient at the bath/cartilage interface, as seen previously for penetration of Avidin into cartilage (Bajpayee et al. Biomaterials 35(1):538-549 (2014)) as well as previously reported Donnan equilibrium measurements of ions in cartilage [26] and low molecular weight peptide drugs (Byun et al. Arch. Biochem. Biophys. 499(1-2): 32-39 (2010)). GFP charge can also lead to binding interactions with cartilage matrix which were incorporated through a reaction rate term in the model. Since the bath volume and cartilage dimensions were known along with estimates for diffusivity, the only remaining unknown parameters in the model were the partition coefficient and the rate constant for binding of +9 S-GFP to matrix sites. These parameters were calculated by fitting the model to the experimental data (see Table 1). The partition coefficient was found to be 10.9 for human cartilage and 11.2 for bovine cartilage, while the reaction rate constants were 1.2*10−5 s−1 and 6.4*10−5 s−1 respectively. The resulting model fit, as well as the sensitivity of model predictions to values of partition coefficient and reaction rate are shown for human cartilage and bovine cartilage.

The mathematical equations for transport (both bath and tissue) are identically applicable to the dynamic uptake experiments and the transient uptake experiments with measurements at 24 h and 8 days were measured. (The only differences between the two experiments were the bath volume and the size of the cartilage disks used.) The model was thereby used to predict the bath concentration and uptake ratio when the bath volume and cartilage dimensions were changed to those of the uptake experiments. Using values of the diffusivity, partition coefficient and reaction rate constant identical to those for the dynamic uptake experiment, the predicted values of 24 h and 8-day uptake of +9 GFP compare favorably with the experimental data.

Finally, the model was used to predict the transport of +9 GFPs into human knee cartilage for the case of intra-articular injection into the knee joint. The diffusivity, partition coefficient and reaction rate constant were assumed to be the same as the values for the dynamic uptake experiment while literature values were used for human knee synovial fluid volume and cartilage thickness (Kraus et al., Osteoarthritis Cartilage 15(10): 1217-1220 (2007); Hewitt et al., Surg. Radio. Anat. 30(8): 645-651 (2008); Shepherd et al., Ann. Rheum. Dis. 58(1):27-34 (1999); Malda et al., PLoS One 8(2): e57683 (2013)). A full numerical solution for +9 GFP concentration in synovial fluid and cartilage was computed as a function of time using MATLAB. In a separate simulation, the differential equation for the synovial fluid bath was modified to account for continuous clearance of synovial fluid components by the joint capsule synovium tissue. The results for the synovial fluid concentration and the average concentration inside cartilage as a function of time for the case study of a human knee were measured. The sensitivity of these predictions to changes in the partition coefficient and the reaction rate constant were measured.

Mass balance of +9 GFP in the bath is governed by:

$$\frac{dV_b c_b}{dt} + \int\int_S \vec{N} \cdot d\vec{A} = 0 \quad (1)$$

where $V_b$ is the volume of the bath, $c_b$ is the bath concentration of +9 GFP, N is the flux of +9 GFP into cartilage and A is the surface area vector of cartilage.

Initial condition in bath:

$$c_b|_{t=0} = c_{b0} \quad (2)$$

where $c_{b0}$ is the initial concentration of +9 GFP in the bath.

Assuming a simple 1-D case where there is only diffusive flux at the interface, $$\frac{dV_b c_b}{dt} - A_{cart} D_{cart} \frac{\partial c_{cart}}{\partial x}\bigg|_{x=0,t} = 0 \quad (3)$$

Here, $c_{cart}$ is the concentration of +9 GFP inside cartilage and x is the spatial coordinate in cartilage ranging from x=0 at the interface with the bath to x=L (where L is the thickness of cartilage) at the location of the impermeable wall.

Since the bath volume is a constant:

$$V_b \frac{dc_b}{dt} = A_{cart} D_{cart} \frac{\partial c_{cart}}{\partial x}\bigg|_{x=0,t} \quad (4)$$

From Equation 2, the initial condition becomes:

$$c_b(t=0) = c_{b0} \quad (5)$$

and the diffusion-reaction equation for the concentration of free +9 GFP inside cartilage is $$\frac{\partial c_{cart}}{\partial t} = D\frac{\partial^2 c_{cart}}{\partial x^2} + R \tag{6}$$

where D is the diffusion coefficient of +9 GFP in cartilage, and R is the net rate of generation or formation of free +9 GFP inside cartilage associated with its binding in cartilage.

For the case of a reversible binding reaction, $$F + S \underset{k_b}{\overset{k_f}{\rightleftharpoons}} B \tag{7}$$

$$R = -k_f c_{cart} c_S + k_b c_B \tag{8}$$

$$c_S + c_B = N_T \tag{9}$$

where F represents the free +9 GFP molecules inside cartilage, S represents the free binding sites and B represents the bound GFP-binding site complex. In Equation 8, first order reaction rates are assumed for both the forward and backward reaction rates of the reaction shown in Equation 7. The forward reaction (rate constant $k_f$) here is the binding of free GFP to free binding sites (concentration $c_S$), while the backward reaction (rate constant $k_b$) is the unbinding of GFP from bound sites ($c_B$). The total initial binding site concentration (NT) in the tissue is then defined in equation (9).

The concentration of negatively charged groups in cartilage is on the order of 100 mM ([1]) while GFP concentrations in the tissue are on the order of 1 to 100 μM. Therefore, it is reasonable to assume that $c_B \ll N_T$, which means:

$$c_S \sim N_T \tag{10}$$

Early in the process, the forward reaction will dominate the reverse reaction, and the second term in Equation 8 will be negligible compared to the first term. Alternately, in addition to $c_B \ll N_T$, if $k_b c_B \ll k_f c_F c_S$ (which will be true if the dissociation constant (equal to $k_b/k_f$) is very small), then the second term in equation (8) can be ignored. Therefore the equations (6), (8) and (9) become:

$$\frac{\partial c_{cart}}{\partial t} = D\frac{\partial^2 c_{cart}}{\partial x^2} - kc_{cart} \tag{11}$$

$$R = -k_f N_T c_{cart} = -kc_{cart} \tag{12}$$

$$k = k_F N_T \tag{13}$$

Note: An alternative way of obtaining Equation 12 is to assume that the binding reaction of +9 GFP to cartilage is irreversible.

The boundary conditions at x=0 involves partitioning at interface with bath:

$$c_{cart}(x=0,t) = K_p c_b(t) \tag{14}$$

Here, $K_p$ is the partition coefficient of +9 GFP in cartilage. At x=L, the no flux boundary condition $$\left.\frac{\partial c_{cart}}{\partial x}\right|_{x=L,t} = 0 \tag{15}$$

There is no GFP inside cartilage at the start of the experiment. Therefore, the initial condition is:

$$c_{cart}(x,t=0) = 0 \tag{16}$$

The model equations were non-dimensionalized to obtain:

$$\frac{d\tilde{c}_b}{d\tilde{t}} = \frac{A_{cart}L}{V_b}\left.\frac{\partial \tilde{c}_{cart}}{\partial \tilde{x}}\right|_{\tilde{x}=0,\tilde{t}} \tag{17}$$

$$\tilde{c}_b(\tilde{t}=0) = 1 \tag{18}$$

$$\frac{\partial \tilde{c}_{cart}}{\partial \tilde{t}} = \frac{\partial^2 \tilde{c}_{cart}}{\partial \tilde{x}^2} - \frac{kL^2}{D}\tilde{c}_{cart} \tag{19}$$

$$\tilde{c}_{cart}(\tilde{x}=0,\tilde{t}) = K_p \tilde{c}_b(\tilde{t}) \tag{20}$$

$$\left.\frac{\partial \tilde{c}_{cart}}{\partial \tilde{x}}\right|_{\tilde{x}=1,\tilde{t}} = 0 \tag{21}$$

$$\tilde{c}_{cart}(\tilde{x},\tilde{t}=0) = 0 \tag{22}$$

where $x\sim=x/L$, $t\sim=Dt/L^2$, $c_b\sim=c_b/c_{b0}$ and $c_{cart}\sim=c_{cart}/c_{b0}$.

Two dynamic uptake experiments were performed for a duration of 36 and 48 hours respectively with +9 GFP and cartilage harvested from the knee joints of a young bovine calf and a 35 year old Collins grade 1 human donor. The bath concentration of +9 GFP was quantified as a function of time through fluorescence measurements. In both experiments, the value of GFP diffusivity in cartilage, $D_{cart}$, was estimated to be 2.7*10-11 $m^2/s$ based on the empirical model developed in (DiDomenico et al. Annual Meeting of the Orthopaedic Research Society, New Orleans, L A, 2018 Abstract No. 2121). Since the bath volume, cartilage thickness and cartilage surface area were known, the only unknown variables were the partition coefficient ($K_p$) and the reaction rate constant (k). These were obtained by fitting the non-dimensional equations (17) to (22) to experimental data. This was done by spatial discretization of partial differential equations to obtain a set of ordinary differential equations (ODEs) in time followed by the use of ODE solvers and the optimization toolbox in MATLAB R2015a. Unique values were obtained for both unknown variables by fitting a single curve since the earliest part of the transient response is most sensitive to $K_p$ alone while the later part of the curve is more sensitive to k. The parameters for the fitted curve are given in Table 1.

TABLE 1

Model parameters for dynamic uptake experiments in bovine and human cartilage.

| Parameter | Human dynamic uptake | Bovine dynamic uptake |
|---|---|---|
| Diffusivity (D) ($m^2/s$) | $2.7 * 10^{-11}$ | $2.7 * 10^{-11}$ |
| Partition coefficient ($K_p$) | 10.9 | 11.2 |
| Bath Volume ($V_b$) (mL) | 2 | 7 |
| Cartilage Surface Area ($A_{cart}$) ($mm^2$) | 12.6 | 12.6 |
| Cartilage Thickness (L) (min) | 0.68 | 0.54 |
| Reaction rate constant (k) ($s^{-1}$) | $1.2 * 10^{-5}$ | $6.4 * 10^{-5}$ |

TABLE 2

Predicted and experimental normalized uptake bath concentrations of +9 GFP for human and bovine cartilage.

| Normalized bath concentration | Human cartilage 24 hr | Human cartilage 8 day | Bovine cartilage 24 hr | Bovine cartilage 8 day |
|---|---|---|---|---|
| Predicted | 0.63 | 0.14 | 0.36 | 0.0006 |
| Experimental | 0.46 ± 0.04 | 0.08 ± 0.02 | 0.43 ± 0.044 | 0.12 ± 0.006 |

TABLE 3

Predicted and experimental normalized uptake ratios of +9 GFP for human and bovine cartilage.

| Uptake ratio | Human cartilage 24 hr | Human cartilage 8 day | Bovine cartilage 24 hr | Bovine cartilage 8 day |
|---|---|---|---|---|
| Predicted | 14.4 | 145.1 | 41.9 | $3.6 * 10^4$ |
| Experimental | 37.7 ± 6.0 | 311.8 ± 79.7 | 24.9 ± 3.6 | 166.9 ± 37.5 |

Model Predictions for Uptake Experiments

The equations for transport in the transient uptake experiments would be identical to those in the dynamic uptake experiments detailed above. Therefore the change in bath concentration in the transient uptake experiments is also given by equations (17)-(22). The main difference between the two systems is that the bath volume ($V_b$) and the dimensions of the cartilage ($A_{cart}$ and L) are different. The diffusivity of +9 GFP in cartilage ($D_{cart}$), the partition coefficient ($K_p$) and the reaction rate constant (k) would be the same in both systems. Therefore, the partition coefficient and the reaction rate constant that were estimated by fitting dynamic uptake data can be used along with known parameters to predict the bath concentration in uptake experiments.

Predictions for Transport Inside the Human Joint

The 1-D transport model described in equations 17 to 22 can be used to obtain an estimate for the time scale for the uptake into cartilage of +9 GFPs injected into the human knee joint. The values for diffusivity (D), partition coefficient ($K_p$) and reaction rate constant (k) were assumed to be the same as those reported in Table 1. From values reported in literature, the values for the synovial fluid (SF), cartilage surface area and cartilage thickness were assumed to be 3 mL (Kraus et al., Osteoarthritis Cartilage 15(10): 1217-1220 (2007)), 6000 $mm^2$ (Hewitt et al., Surg. Radio. Anat. 30(8): 645-651 (2008)) and 2 mm (Shepherd et al., Ann. Rheum. Dis. 58(1):27-34 (1999); Malda et al., PLoS One 8(2): e57683 (2013)) respectively. The coupled differential equations were converted into a system of ordinary differential equations (ODEs) by discretizing the spatial derivatives. This system of ODEs was solved using an ODE solver in MATLAB 2015a, and the concentration profile was obtained as a function of time in the bath (SF) and as a function of time and space inside cartilage.

The transport equations used to obtain these concentration profiles do not account for the clearance of molecules from the joint space due to the constant turnover of SF. The SF volume in the human knee joint is turned over in approximately 1 hour (Levick et al., Annals of the Rheumatic Diseases 54(5):417-423 (1995)) and the resulting protein clearance rate is approximately 0.05 mL/min (Wallis et al., Arthritis & Rheumatism 28(4):441-449 (1985); Simkin, Osteoarthritis and Cartilage 21(1):7-9 (2013)). Multiplying this volumetric clearance rate with the SF concentration of +9 GFP will give the molar clearance rate of the GFPs from the joint, and the modified differential equation for the SF concentration will be:

$$V_b \frac{dc_b}{dt} = A_{cart} D_{cart} \frac{\partial c_{cart}}{\partial x}\bigg|_{x=0,t} - R_v c_b \tag{23}$$

where $R_v$ is the volumetric clearance rate from literature.

This new system of equations was solved numerically using MATLAB, and the concentration profiles for the SF and the cartilage can be measured.

Overall, the model predicts that most of the GFP is able to penetrate cartilage within a few hours. Due to this, the rapid clearance by the joint capsule clearance leads to only a modest reduction in the GFP concentration inside cartilage compared to the case where there is no clearance. Additionally, the steady state average concentration of +9 GFP inside cartilage is ~14% of the initial concentration of GFPs in synovial fluid. This can be used to estimate the minimum amount of GFP-drug conjugates that need to be injected into the joint to achieve and maintain a certain drug concentration inside cartilage.

Example 2: Fusion Proteins with +9 GFP and IGF-1 Domains

Based on the results in a previously published paper (Krishnan, Y.+*Biomaterials* 2018), +9 GFP was chosen as the carrier for human IGF-1 (a pro-anabolic protein growth factor). 6 fusion proteins of +9 GFP and human IGF-1 were designed with different peptide linkers. One of the proteins did not have any linker, three had flexible linkers of different lengths and two had rigid linkers of different lengths. Plasmids encoding the proteins were then transformed into *E. coli*, which were then used for protein expression. This was followed by 2-step protein purification. In the first step, the fusion proteins (which had a 6× histidine tag) were isolated using Ni-NTA resin. They were then eluted from the resin and further purified through ion-exchange chromatography using an FPLC machine. The peptide linkers and complete amino acid and DNA sequences for each of the 6 fusion proteins are given in the Sequences section.

Results:

Experiment 1:

Cartilage was harvested from the knee joint of a 23 year old male donor. Cartilage explants were equilibrated in culture media for 2 days after harvest. Many of the cartilage explants had a thickness greater than 1 mm. These were cut down to 1 mm thickness and allowed to equilibrate for a further 2 days before the experiment was set up. Subsets of the experiment were terminated at 3 days and 7 days from the start of the experiment. Media changes were performed every 2 to 3 days.

Experimental groups for each of the two termination time points (N=4 to 6 cartilage explants in each group; most groups had 5 explants): Untreated control (Ctrl in FIG. 1A to FIG. 1C), Continuous Free IGF-1 control (40 nM dose added with every media change) (IGF1 in FIG. 1A to FIG. 1C), (+9GFP)-$(GGGGS)_4$-(IGF-1) (SEQ ID NO: 7) 500 nM dose (Single 500 nM dose added on Day, (Flex-1 in FIG. 1A to FIG. 1C), (+9GFP)-$(GGGGS)_4$-(IGF-1) (SEQ ID NO: 7) 2 μM dose (Single 2 μM dose added on Day 0) (Flex-1 in FIG. 1A to FIG. 1C), (+9GFP)-$(EAAAK)_3$-(IGF-1) (SEQ ID NO: 8) 500 nM dose (Single 500 nM dose added on Day, (Rig-1 in FIG. 1A to FIG. 1C), (+9GFP)-$(EAAAK)_3$-(IGF-1) (SEQ ID NO: 8) 2 μM dose (Single 2 μM dose added on Day 0) (Rig-1 in FIG. 1A to FIG. 1C), (+9GFP)-$(GGGGS)_3$-(IGF-1) (SEQ ID NO: 9) 500 nM dose (Single 500 nM dose added on Day (Flex-2 in FIG. 1A to FIG. 1C), and (+9GFP)-$(GGGGS)_3$-(IGF-1) (SEQ ID NO: 9) 2 μM dose (Single 2 μM dose added on Day 0) (Flex-2 in FIG. 1A to FIG. 1C).

For the 3-day termination experiment, chondrocyte biosynthesis rate (primarily aggrecan synthesis) was measured between days 0 and 3 of the experiment using a 35S-sulfate radiolabel. For the 7-day termination experiment, this measurement was done between days 5 and 7. Statistics: 1-way ANOVA with post-hoc Tukey's HSD test.

Figure 1B:
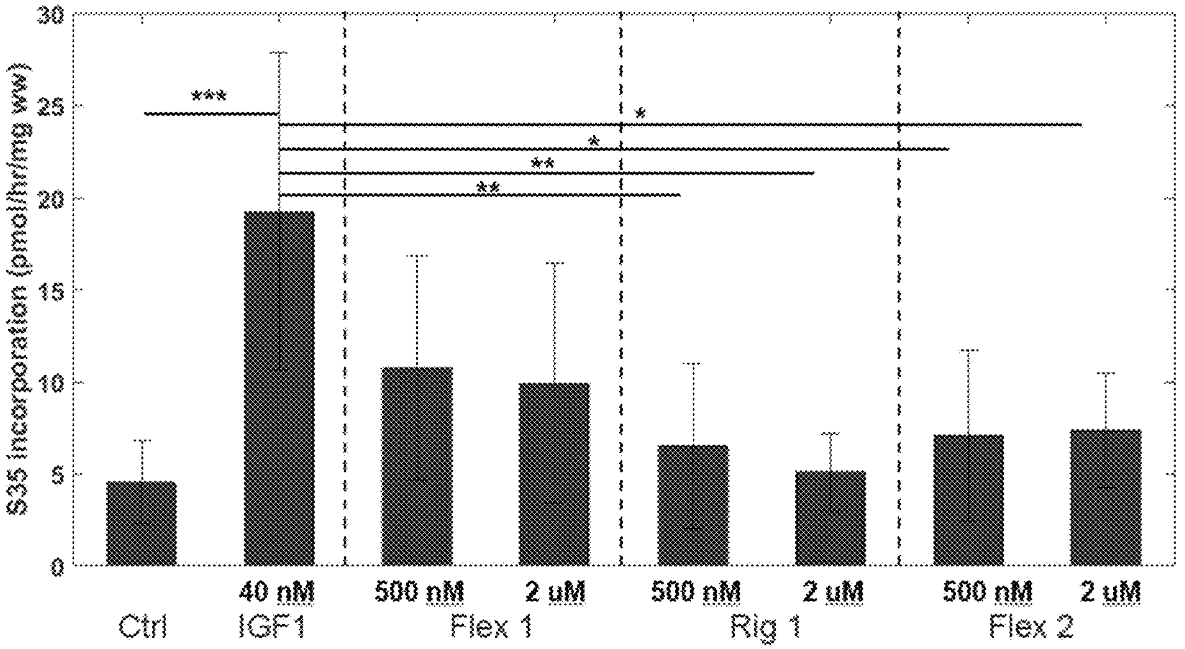
Figure 1C:
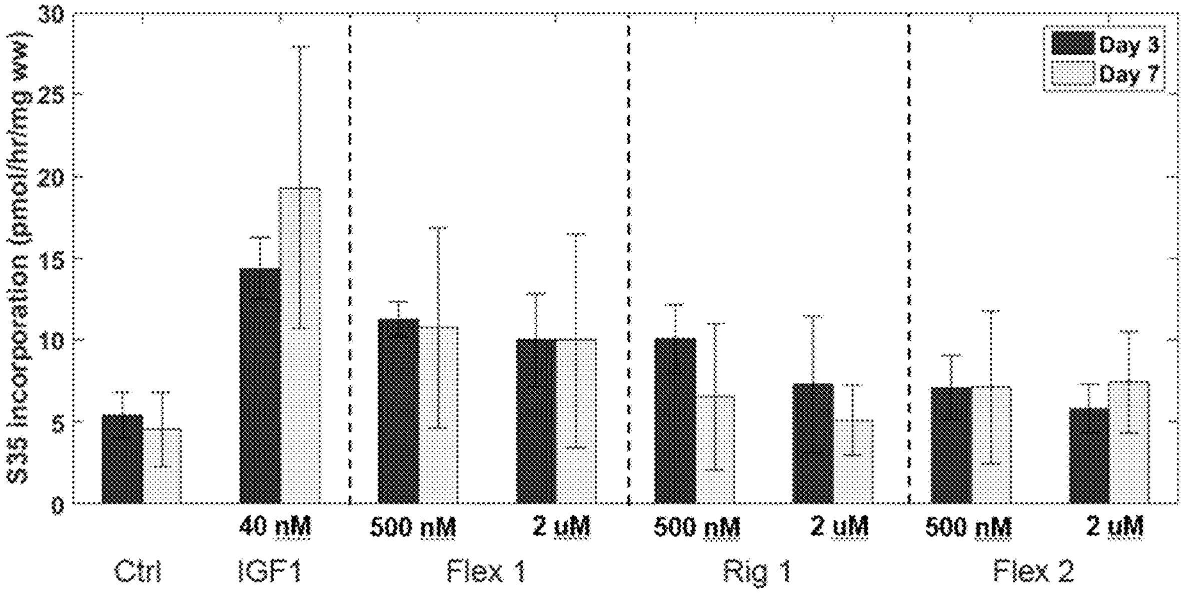

Results from FIG. 1A: At the 3-day time point, the aggrecan biosynthesis rate for the 500 nM (+9GFP)-$(GGGGS)_4$-(IGF-1) (SEQ ID NO: 7) group is significantly higher compared to the untreated control. The aggrecan biosynthesis rates for the 2 μM (+9GFP)-$(GGGGS)_4$-(IGF-1) (SEQ ID NO: 7) group and the 500 nM (+9GFP)-$(EAAAK)_3$-(IGF-1) (SEQ ID NO: 8) group are not statistically significantly different from the untreated control group, but the p-values are 0.0685 and 0.061 respectively (these are close to the 0.05 cutoff value for significance). The biosynthesis rate for the continuous free IGF-1 treatment is significantly higher than the rate for the untreated control, but it is not statistically significantly different from the rates for the 500 nM (+9GFP)-$(GGGGS)_4$-(IGF-1) (SEQ ID NO: 7) group, the 2 μM (+9GFP)-$(GGGGS)_4$-(IGF-1) (SEQ ID NO: 7) group and the 500 nM (+9GFP)-$(EAAAK)_3$-(IGF-1) (SEQ ID NO: 8) group. These results demonstrate that the (+9GFP)-$(GGGGS)_4$-(IGF-1) (SEQ ID NO: 7) fusion protein is bioactive and a 500 nM dose is sufficient to get a response. They also indicate that the (+9GFP)-$(EAAAK)_3$-(IGF-1) (SEQ ID NO: 8) is potentially bioactive as well. Results from FIG. 1B: At the 7-day time point, the biosynthesis rate for the continuous free IGF-1 treatment is significantly higher than the rate for the untreated control. At the same time point, the aggrecan biosynthesis rates for the 500 nM (+9GFP)-$(GGGGS)_4$-(IGF-1) (SEQ ID NO: 7) group and the 2 μM (+9GFP)-$(GGGGS)_4$-(IGF-1) (SEQ ID NO: 7) group are not statistically significantly different from the untreated control, but they are also not different compared to the continuous free IGF-1 treatment group. Results from FIG. 1C: This figure shows the comparison between the 3-day time point (dark gray bars) and the 7-day time point (light gray bars) for all the treatment groups. The mean aggrecan biosynthesis rate at Day 7 is the same as the rate on Day 3 for the 500 nM and 2 μM doses of (+9GFP)-$(GGGGS)_4$-(IGF-1) (SEQ ID NO: 7). This indicates that a single dose on Day 0 of this fusion protein is able to maintain a prolonged response in cartilage tissue.

Experiment 2:

Cartilage was harvested from the knee joint of a 38 year old male donor. Cartilage explants were equilibrated in culture media for 3 days after harvest. Many of the cartilage explants had a thickness greater than 1 mm. These were cut down to 1 mm thickness and allowed to equilibrate for a further 3 days before the experiment was set up. Subsets of the experiment were terminated at 3 days and 7 days from the start of the experiment. Media changes were performed every 2 to 3 days.

Experimental groups for each of the two termination time points (N=5 cartilage explants in each group): Untreated control (Ctrl in FIG. 2A to FIG. 2C), Continuous Free IGF-1 control (40 nM dose added with every media change) (IGF1 in FIG. 2A to FIG. 2C), (+9GFP)-$(GGGGS)_4$-(IGF-1) (SEQ ID NO: 7) 500 nM dose (Single 500 nM dose added on Day 1) (Flex-1 in FIG. 2A to FIG. 2C), (+9GFP)-$(GGGGS)_4$-(IGF-1) (SEQ ID NO:7) 1 μM dose (Single 1 μM dose added on Day 0) (Flex-1 in FIG. 2A to FIG. 2C), (+9GFP)-$(GGGGS)_4$-(IGF-1) (SEQ ID NO: 7) 2 μM dose (Single 2 μM dose added on Day 0) (Flex-1 in FIG. 2A to FIG. 2C), (+9GFP)-$(EAAAK)_3$-(IGF-1) (SEQ ID NO: 8) 500 nM dose (Single 500 nM dose added on Day 1) (Rig-1 in FIG. 2A to FIG. 2C), (+9GFP)-$(EAAAK)_3$-(IGF-1) (SEQ ID NO: 8) 1 μM dose (Single 1 μM dose added on Day 0) (Rig-1 in FIG. 2A to FIG. 2C), (+9GFP)-$(EAAAK)_3$-(IGF-1) (SEQ ID NO: 8) 2 μM dose (Single 2 μM dose added on Day 0) (Rig-1 in FIG. 6A to FIG. 6C), (+9GFP)-$(GGGGS)_3$-(IGF-1) (SEQ ID NO: 9) 500 nM dose (Single 500 nM dose added on Day 1) (Flex-2 in FIG. 2A to FIG. 2C), (+9GFP)-$(GGGGS)_3$-(IGF-1) (SEQ ID NO: 9) 1 μM dose (Single 1 μM dose added on Day 0) (Flex-2 in FIG. 2A to FIG. 2C), (+9GFP)-$(GGGGS)_3$-(IGF-1) (SEQ ID NO: 9) 2 μM dose (Single 2 μM dose added on Day 0) (Flex-2 in FIG. 2A to FIG. 2C).

For the 3-day termination experiment, chondrocyte biosynthesis rate (primarily aggrecan synthesis) was measured between days 0 and 3 of the experiment using a 35S-sulfate radiolabel. For the 7-day termination experiment, this measurement was done between days 5 and 7. Statistics: 1-way ANOVA with post-hoc Tukey's HSD test.

Figure 2A:
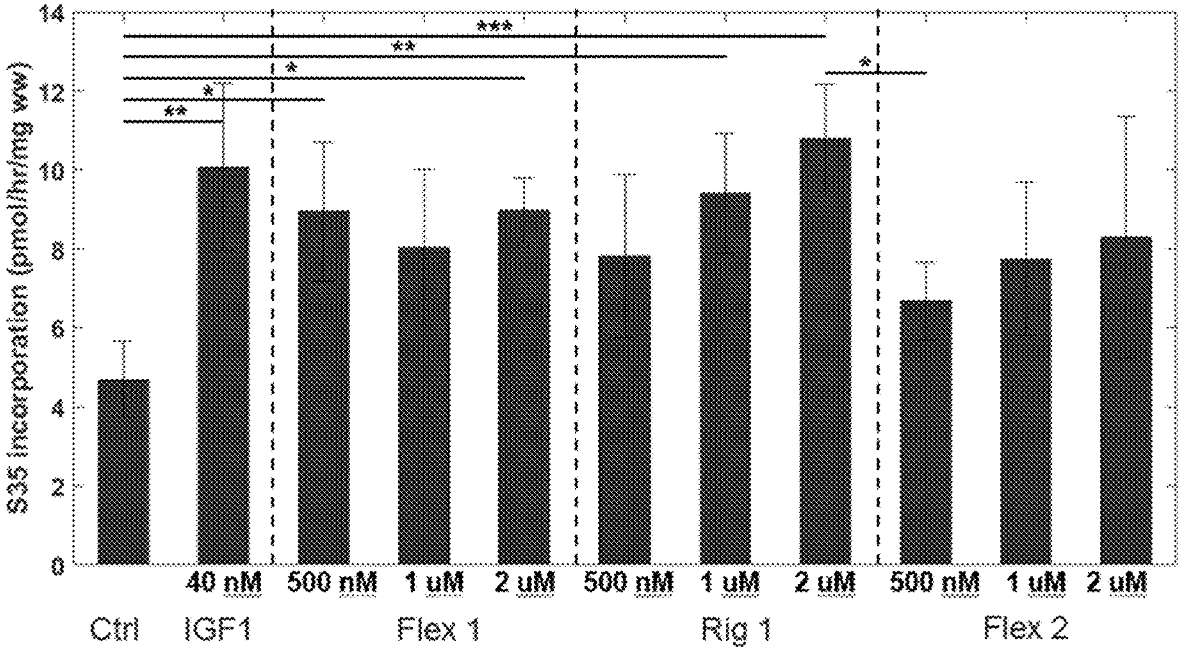
FIGS. 2A-2C show aggrecan biosynthesis rate measured between days 0 and 3; days 5 and 7, and at the 7-day time point and the 3-day time point in experiment 4.
Figure 2B:
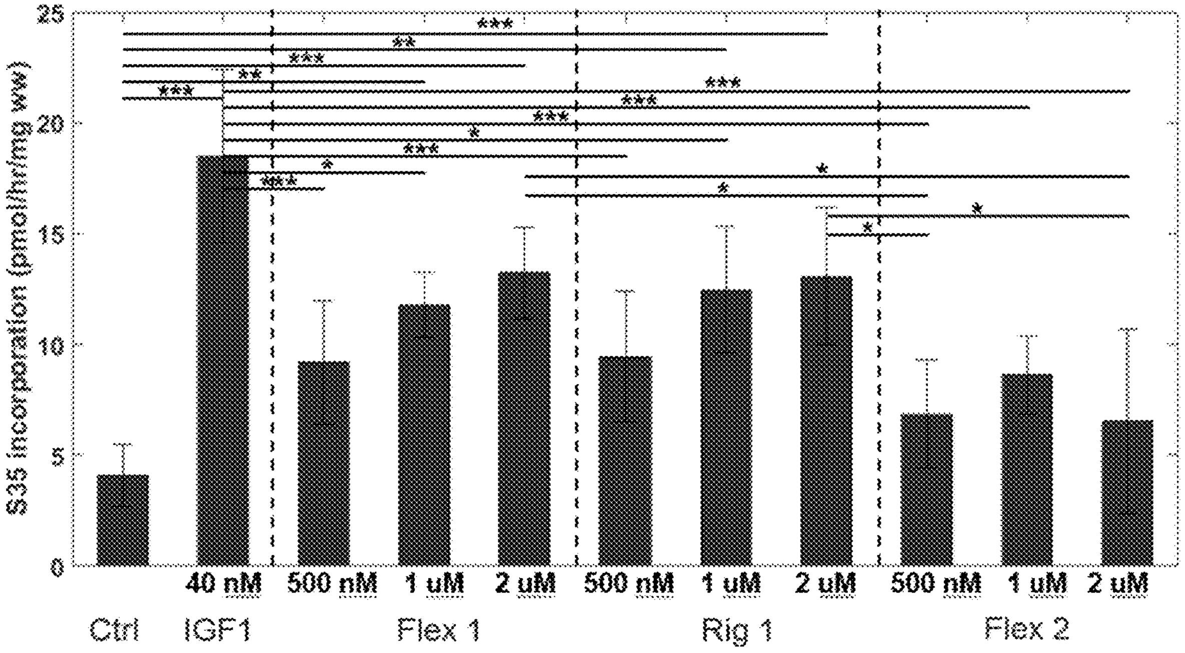
Figure 2C:
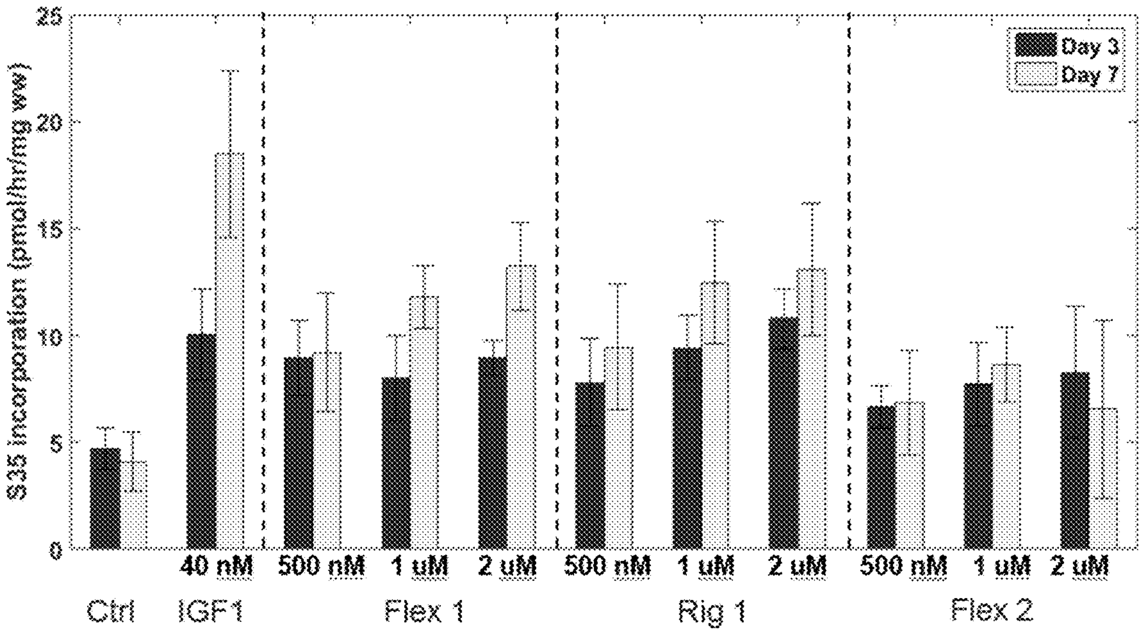

Results from FIG. 2A: At the 3-day time point, the aggrecan biosynthesis rate for the continuous free IGF-1 group, the 500 nM and 2 μM doses of (+9GFP)-$(GGGGS)_4$-(IGF-1) (SEQ ID NO: 7) as well as the 1 μM and 2 μM doses of (+9GFP)-$(EAAAK)_3$-(IGF-1) (SEQ ID NO: 8) are all statistically significantly higher compared to the untreated control. These results demonstrate that both (+9GFP)-$(GGGGS)_4$-(IGF-1) (SEQ ID NO: 7) and (+9GFP)-$(EAAAK)_3$-(IGF-1) (SEQ ID NO: 8) are bioactive in human cartilage at doses equal to or greater than 500 nM. There are no statistically significant differences between the continuous free IGF1 group and any of the fusion protein treatment groups. Results from FIG. 2B: At the 7-day time point, the aggrecan biosynthesis rate for the continuous free IGF-1 group, the 1 μM and 2 μM doses of (+9GFP)-$(GGGGS)_4$-(IGF-1) (SEQ ID NO: 7) as well as the 1 μM and 2 μM doses of (+9GFP)-$(EAAAK)_3$-(IGF-1) (SEQ ID NO: 8) are all statistically significantly higher compared to the untreated control. The aggrecan biosynthesis rate for the continuous free IGF-1 group is significantly higher than all groups except for the 2 μM dose of (+9GFP)-$(GGGGS)_4$-(IGF-1) (SEQ ID NO: 7) and the 2 μM dose of (+9GFP)-$(EAAAK)_3$-(IGF-1) (SEQ ID NO: 8). These results provide additional evidence that (+9GFP)-$(GGGGS)_4$-(IGF-1) (SEQ ID NO: 7) and (+9GFP)-$(EAAAK)_3$-(IGF-1) (SEQ ID NO: 8) are bioactive in human cartilage, and a single dose of both these fusion proteins has a prolonged effect that lasts for at least 1 week after administration. FIG. 2C shows the comparison between the 3-day time point (dark gray bars) and the 7-day time point (light gray bars) for all the treatment groups.

Experiment 3:

Cartilage was harvested from both ankles of a 66 year old male donor (Collins Grade 0). Cartilage explants were equilibrated in culture media for 3 days after harvest. Many of the explants had a thickness greater than 1 mm. These were cut down to 1 mm thickness and allowed to equilibrate for a further 2.5 days before experiments were set up. A dose response experiment and an uptake experiment were set up in parallel.

Experiment 3A (Dose Response):

Subsets of the experiment were terminated at 3 days and 7 days from the start of the experiment. Media changes were performed every 2 to 3 days. 3 doses of free +9 GFP were included as additional controls, which tests whether high doses of the drug delivery carrier has adverse effects on aggrecan biosynthesis rate.

Experimental groups for each of the two termination time points (N=7 to 9 cartilage explants in each group): Untreated control (Ctrl in FIG. 3A to FIG. 3D), Continuous Free IGF-1 control (40 nM dose added with every media change) (IGF1 in FIG. 3A to FIG. 3D), (+9GFP)-$(GGGGS)_4$-(IGF-1) (SEQ ID NO: 7) 500 nM dose (Single 500 nM dose added on Day 1 (Flex-1 in FIG. 3A to FIG. 3D), (+9GFP)-$(GGGGS)_4$-(IGF-1) (SEQ ID NO: 7) 1 μM dose (Single 1 μM dose added on Day 0) (Flex-1 in FIG. 3A to FIG. 3D), (+9GFP)-$(GGGGS)_4$-(IGF-1) (SEQ ID NO: 7) 2 μM dose (Single 2 μM dose added on Day 0) (Flex-1 in FIG. 3A to FIG. 3D), (+9GFP)-$(EAAAK)_3$-(IGF-1) (SEQ ID NO: 8) 500 nM dose (Single 500 nM dose added on Day 1 (Rig-1 in FIG. 3A to FIG. 3D), (+9GFP)-$(EAAAK)_3$-(IGF-1) (SEQ ID NO: 8) 1 μM dose (Single 1 μM dose added on Day 0) (Rig-1 in FIG. 3A to FIG. 3D), (+9GFP)-$(EAAAK)_3$-(IGF-1) (SEQ ID NO: 8) 2 μM dose (Single 2 μM dose added on Day 0) (Rig-1 in FIG. 3A to FIG. 3D), +9GFP 500 nM dose (Free carrier control) (Single 500 nM dose added on Day 0) (+9 GFP in FIG. 3A to FIG. 3D), +9GFP 1 μM dose (Free carrier control) (Single 1 μM dose added on Day 0) (+9 GFP in FIG. 3A to FIG. 3D), +9GFP 2 μM dose (Free carrier control) (Single 2 μM dose added on Day 0) (+9 GFP in FIG. 3A to FIG. 3D).

For the 3-day termination experiment, chondrocyte biosynthesis rate (primarily aggrecan synthesis) was measured between days 0 and 3 of the experiment using a 35S-sulfate radiolabel. For the 7-day experiment, this measurement was done between days 5 and 7. Statistics: 1-way ANOVA with post-hoc Tukey's HSD test.

Figure 3A:
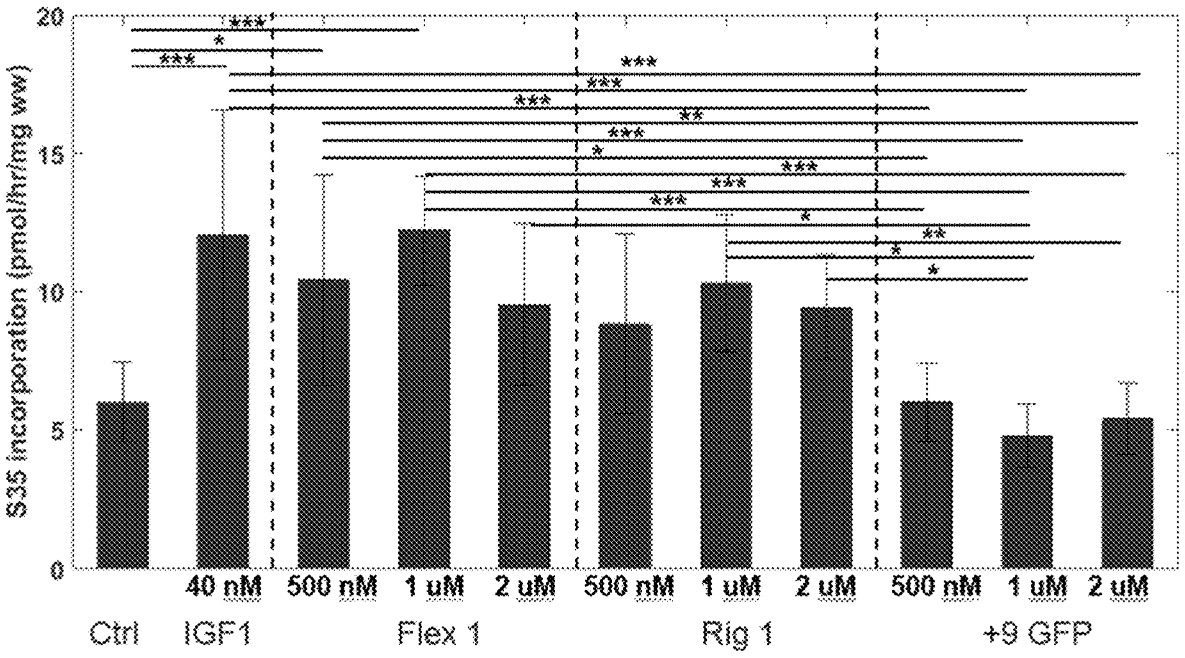
FIGS. 3A-3D show aggrecan biosynthesis rate measured between days 0 and 3; days 5 and 7, and at the 7-day time point and the 3-day time point in experiment 5A.
Figure 3B:
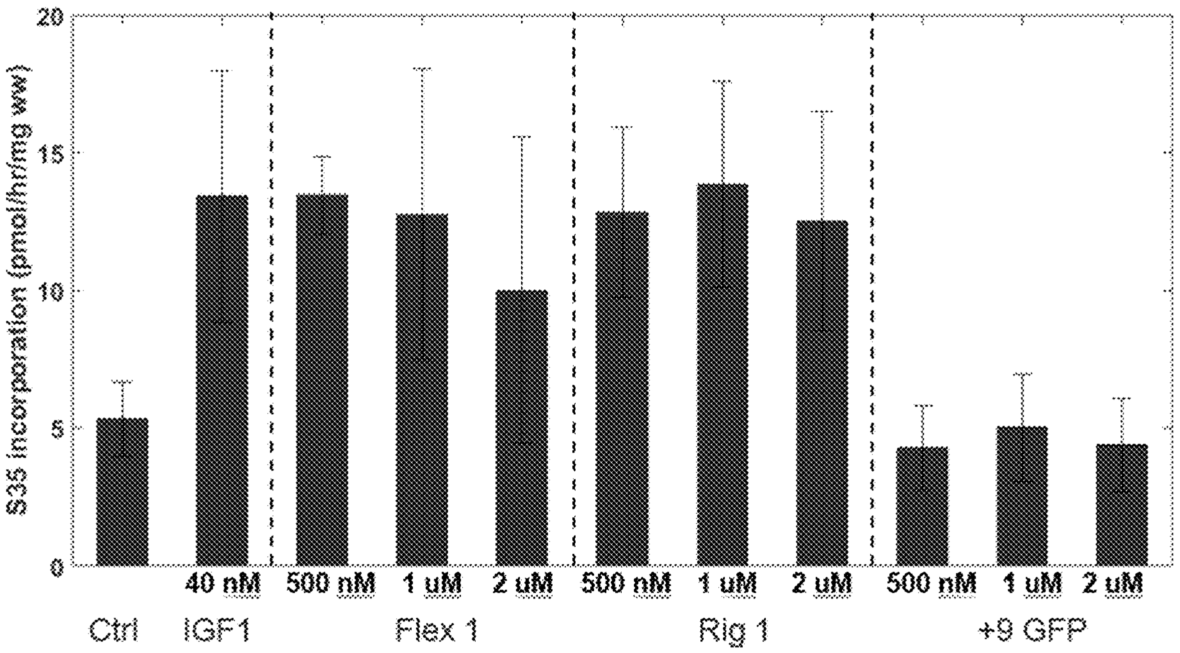
Figure 3C:
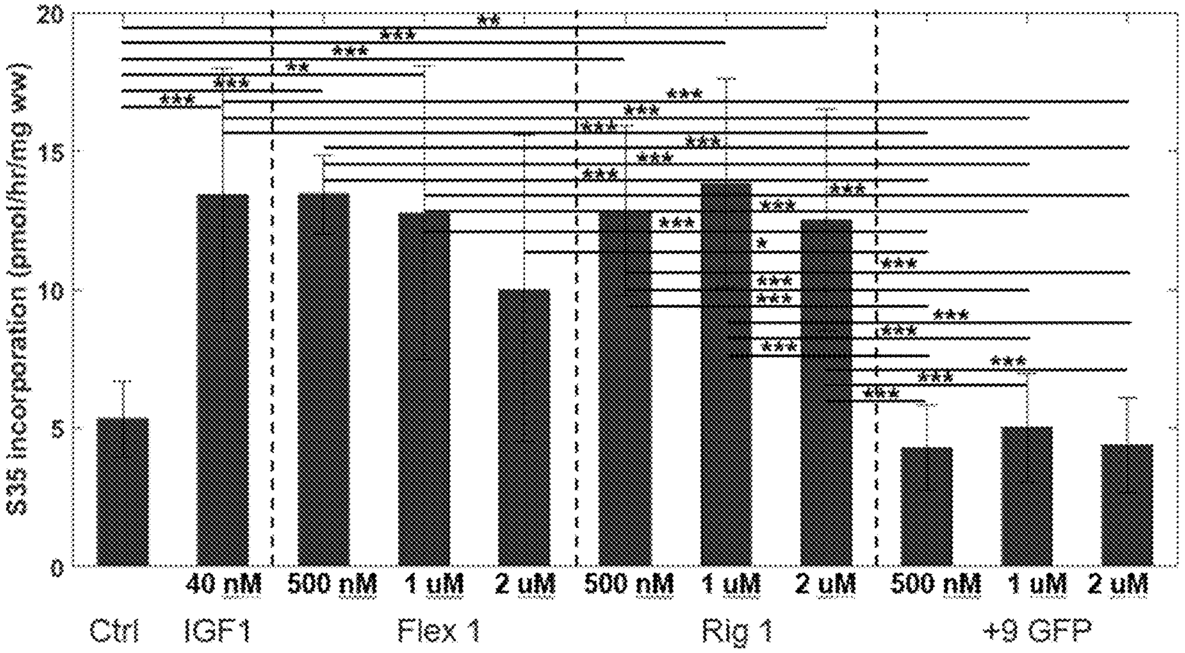
Figure 3D:
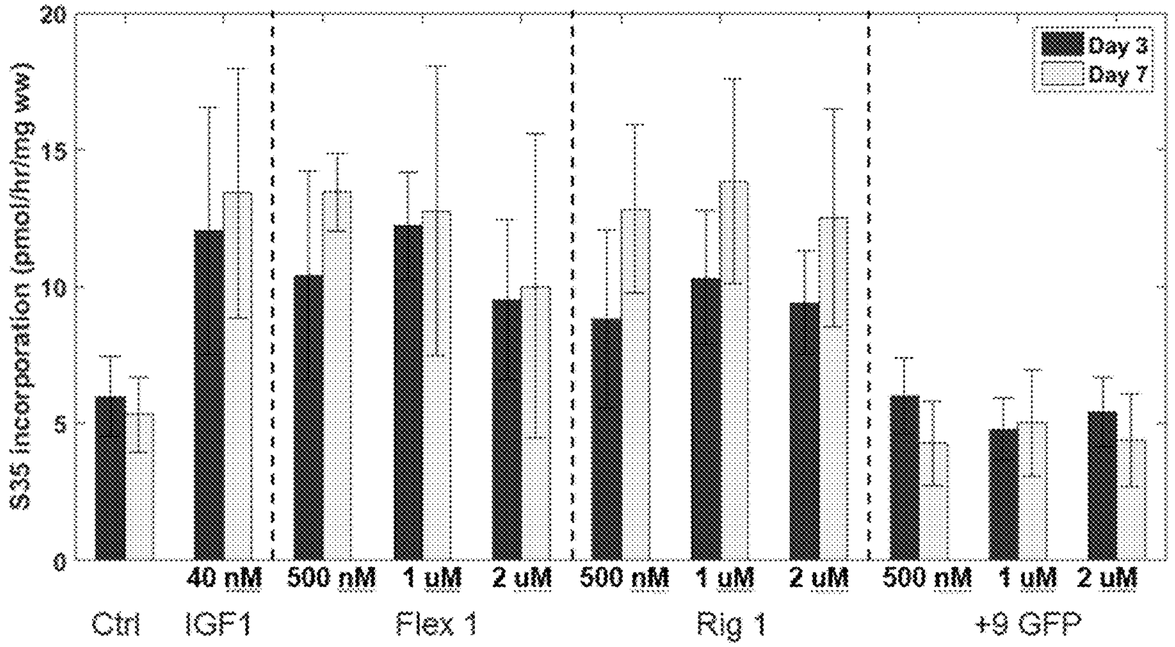

Results from FIG. 3A: At the 3-day time point, the aggrecan biosynthesis rate for the continuous free IGF-1 group as well as the 500 nM and 2 μM doses of (+9GFP)-$(GGGGS)_4$-(IGF-1) (SEQ ID NO: 7) are all statistically significantly higher compared to the untreated control. These results demonstrate that the (+9GFP)-$(GGGGS)_4$-(IGF-1) (SEQ ID NO: 7) fusion protein is bioactive in human ankle cartilage. There are no statistically significant differences between the continuous free IGF1 group and any of the fusion protein treatment groups. This indicates that (+9GFP)-$(EAAAK)_3$-(IGF-1) (SEQ ID NO: 8) is also potentially bioactive. The three +9 GFP control groups are not statistically significantly different from the untreated control group. This indicates that the carrier domain in the fusion protein does not have any effect on the biosynthesis rate at doses between 500 nM and 2 μM. Any changes in the biosynthesis rate are only due to the IGF-1 domain. Results from FIGS. 3B-3C: At the 7-day time point, the aggrecan biosynthesis rate for the continuous free IGF-1 group, the 500 nM and 1 μM doses of (+9GFP)-$(GGGGS)_4$-(IGF-1) (SEQ ID NO: 7) as well as all three doses of (+9GFP)-$(EAAAK)_3$-(IGF-1) (SEQ ID NO: 8) are statistically significantly higher compared to the untreated control. This demonstrates that both (+9GFP)-$(GGGGS)_4$-(IGF-1) (SEQ ID NO: 7) and (+9GFP)-$(EAAAK)_3$-(IGF-1) (SEQ ID NO: 8) are bioactive in human ankle cartilage at dose levels greater than or equal to 500 nM. The aggrecan biosynthesis rate for the continuous free IGF-1 group is not statistically significantly different from any of the 6 groups with the fusion proteins. This indicates that a single dose of these fusion proteins at the start of the experiment can provide a sustained effect that is comparable to continuous dosing of free IGF-1 for a duration of 1 week. Similar to the 3-day experiment, the three +9 GFP control groups are not statistically significantly different from the untreated control group.

Experiment 3B (Uptake):

Cartilage explants were incubated in 250 μL of 1 μM solutions of different fusion proteins dissolved in 1×PBS+1% BSA for either 36 hours (FIG. 4A) or for 108 hours (FIG. 4B) (4.5 days). A group with free +9 GFP dissolved in 1×PBS+1% BSA (1 μM concentration) was included as a control for each of these two time points. An additional untreated control was included in these experiments. Cartilage explants were incubated in plain 1×PBS+1% BSA to account for and to correct for any autofluorescence effects. At the end of the incubation in the 1×PBS+1% BSA: The explants were transferred to a 10×PBS+1% BSA bath for 48 hours. The purpose of this was to desorb the GFPs taken up by the explants. The amount of GFPs left behind in the 1×PBS+1% BSA bath was quantified through fluorescence measurements. The desorption step in 10×PBS+1% BSA was followed by a second desorption step using fresh 10×PBS+1% BSA just to ensure any GFPs left in the explant after the 1st desorption come out. At the end of each desorption step, the fluorescence of the 10×PBS+1% BSA bath was measured. After the 2nd desorption step, the explants were digested in Proteinase K and their fluorescence was measured. The uptake ratio for the 36 hour and 108 hour experiments was calculated as (FIG. 4C):

$$\text{Uptake ratio} = \frac{\text{Concentration of } GFP \text{ inside cartilage explant} \left(\frac{\text{mol}}{\text{g}} \text{wet weight}\right)}{\text{Final concentration of } GFP \text{ left behind in absorption bath} \left(\frac{\text{mol}}{\text{mL}}\right)}$$

Figure 4A:
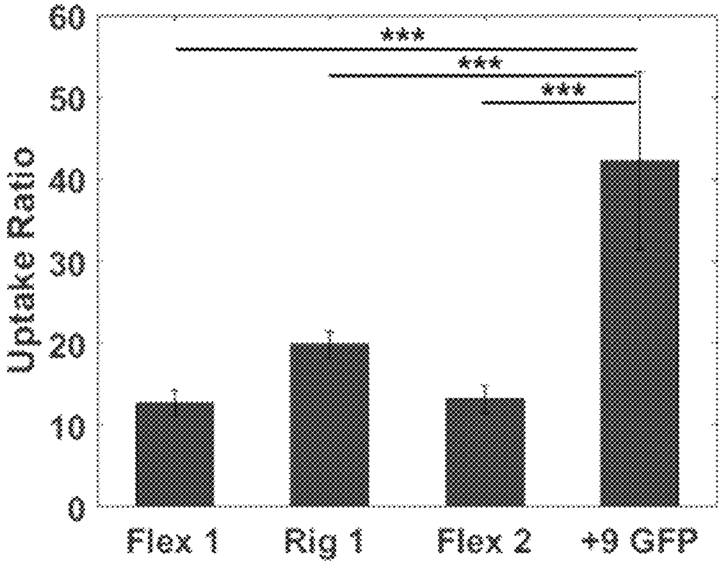
FIGS. 4A-4C show 36 hour uptake ratios, 108 hour uptake ratios, and a comparison of 36 hour and 108 hour uptake ratios.
Figure 4B:
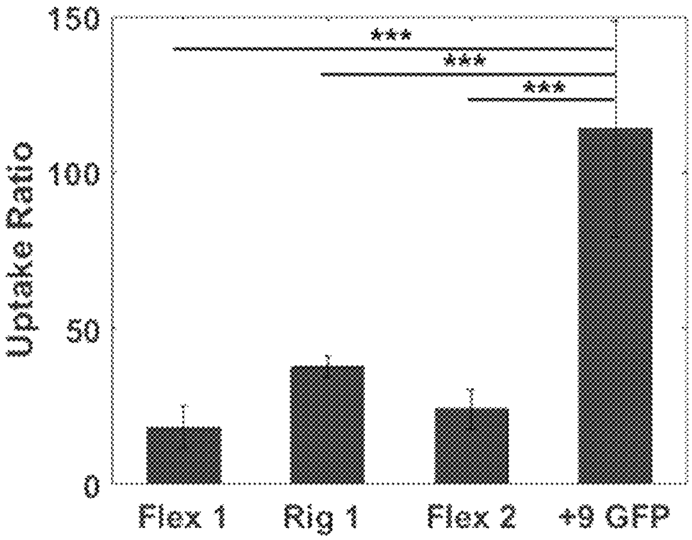
Figure 4C:
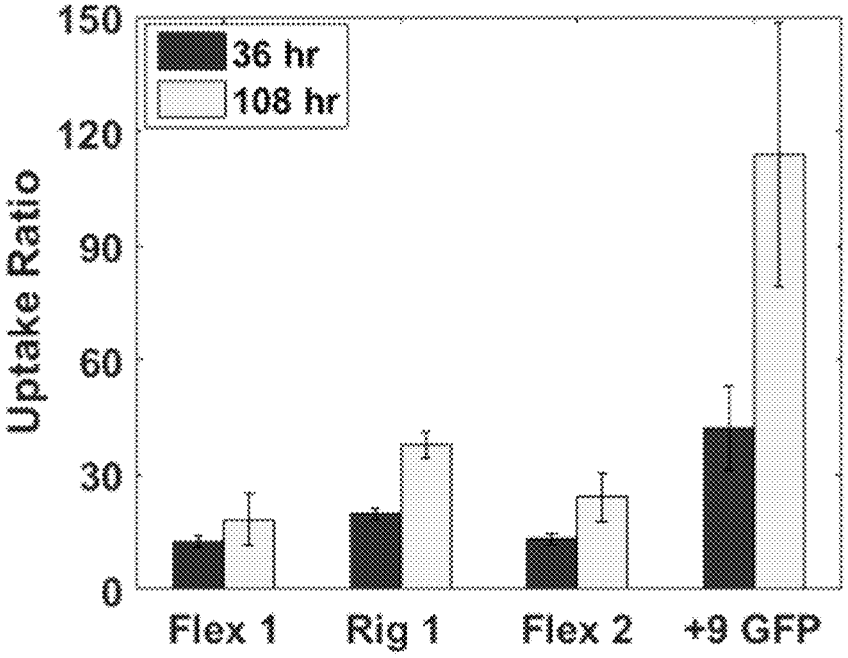

In this formula, GFP can refer to free +9 GFP or to a fusion protein. In FIGS. 4A-4C, "Flex 1" refers to (+9GFP)-$(GGGGS)_4$-(IGF-1) (SEQ ID NO: 7), "Rig 1" refers to (+9GFP)-$(EAAAK)_3$-(IGF-1) (SEQ ID NO: 8), "Flex 2" refers to (+9GFP)-$(GGGGS)_3$-(IGF-1) (SEQ ID NO: 9) and "+9 GFP" is the free carrier.

Experiment 4:

Cartilage was harvested from the ankle of a 58 year old male donor (Collins Grade 1). Cartilage explants were equilibrated in culture media for 2 days after harvest. Many of the explants had a thickness greater than 1 mm. These were cut down to 1 mm thickness and allowed to equilibrate for a further 2.5 days before experiments were set up. A 7-day dose response experiment was set up.

Experimental groups (N=9 to 10 cartilage explants in each group): Untreated control (Ctrl in FIGS. 5A-5B), Continuous Free IGF-1 control (40 nM dose added with every media change) (IGF1 FIGS. 5A-5B), (+9GFP)-$(GGGGS)_4$-(IGF-1) (SEQ ID NO: 7) 500 nM dose (Single 500 nM dose added on Day 1 (Flex-1 in FIGS. 5A-5B), (+9GFP)-$(GGGGS)_4$-(IGF-1) (SEQ ID NO: 7) 1 μM dose (Single 1 μM dose added on Day 0) (Flex-1 FIGS. 5A-5B), (+9GFP)-$(EAAAK)_3$-(IGF-1) (SEQ ID NO: 8) 500 nM dose (Single 500 nM dose added on Day 1 (Rig-1 in FIGS. 5A-5B), (+9GFP)-$(EAAAK)_3$-(IGF-1) (SEQ ID NO: 8) 1 μM dose (Single 1 μM dose added on Day 0) (Rig-1 in FIGS. 5A-5B).

Chondrocyte biosynthesis rate (primarily aggrecan synthesis) was measured between days 5 and 7 of the experiment using a 35S-sulfate radiolabel. Statistics: 1-way ANOVA with post-hoc Tukey's HSD test.

Figure 5A:
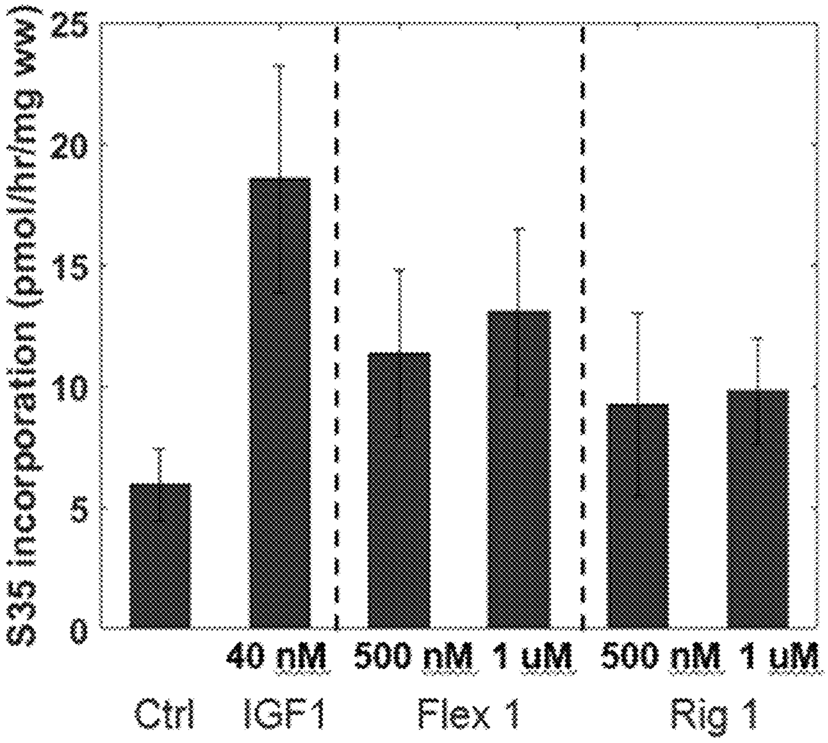
FIGS. 5A-5B show aggrecan biosynthesis rate for the continuous free IGF-1 group as well as the 500 nM and 1 μM doses of (+9GFP)-$(GGGGS)_4$-(IGF-1) (SEQ ID NO: 7) are all statistically significantly higher compared to the untreated control
Figure 5B:
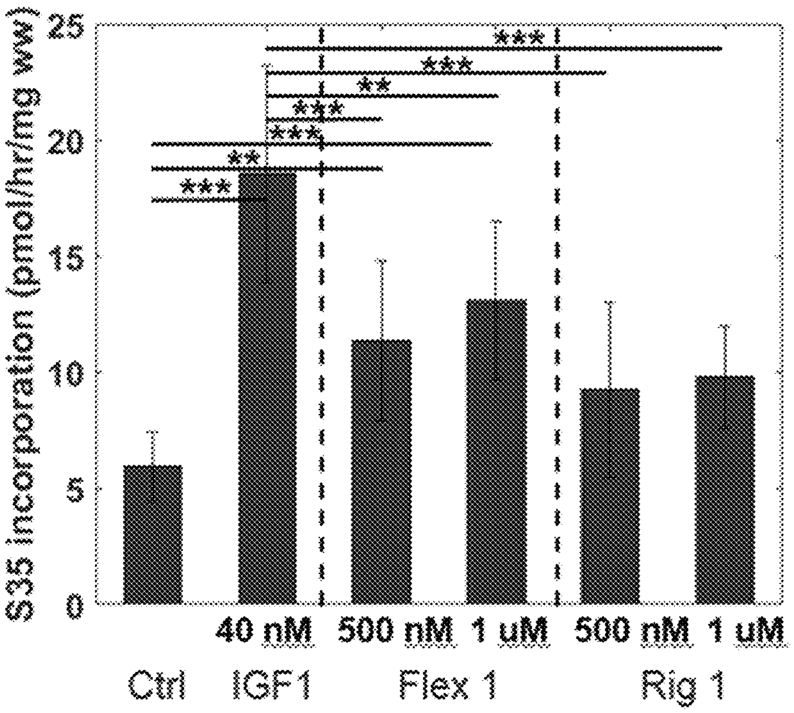

Results from FIGS. 5A-5B: The aggrecan biosynthesis rate for the continuous free IGF-1 group as well as the 500 nM and 1 μM doses of (+9GFP)-$(GGGGS)_4$-(IGF-1) (SEQ ID NO: 7) are all statistically significantly higher compared to the untreated control.

Experiment 5:

Cartilage was harvested from the ankles of a 58 year old male donor (Collins Grade 1) and a 68 year old male donor (Collins Grade 1). Cartilage explants were equilibrated in culture media for 2 days after harvest. Many of the explants had a thickness greater than 1 mm. These were cut down to 1 mm thickness and allowed to equilibrate for a further 2 days before experiments were set up. Human IL-1β was used to induce osteoarthritis-like changes in cartilage. Experiments were set up to identify IL-1β doses at which 40 nM of free IGF-1 can rescue the IL-1β induced biosynthesis loss in cartilage. A dose response experiment in which single doses of (+9GFP)-$(GGGGS)_4$-(IGF-1) (SEQ ID NO: 7) and (+9GFP)-$(EAAAK)_3$-(IGF-1) (SEQ ID NO: 8) were added along with 100 pg/ml human IL-1β was also set up.

Figure 6A:
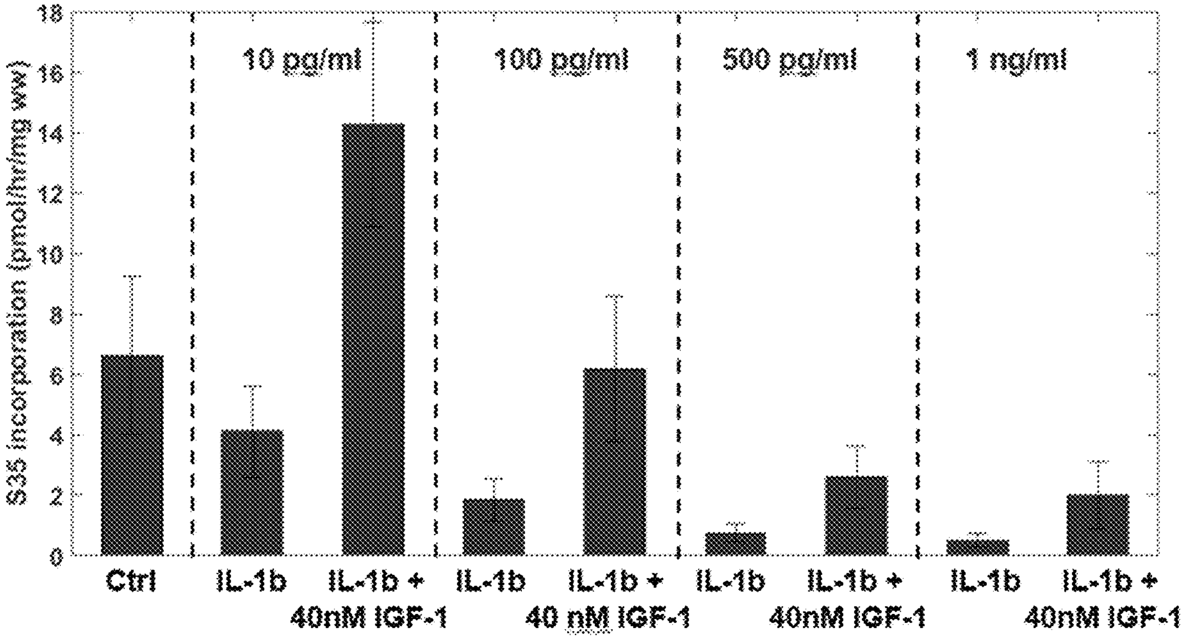
FIGS. 6A-6C show 100 pg/ml, 500 pg/ml and 1000 pg/ml doses of human IL-1β cause a significant reduction in aggrecan biosynthesis compared to the untreated control.
Figure 6B:
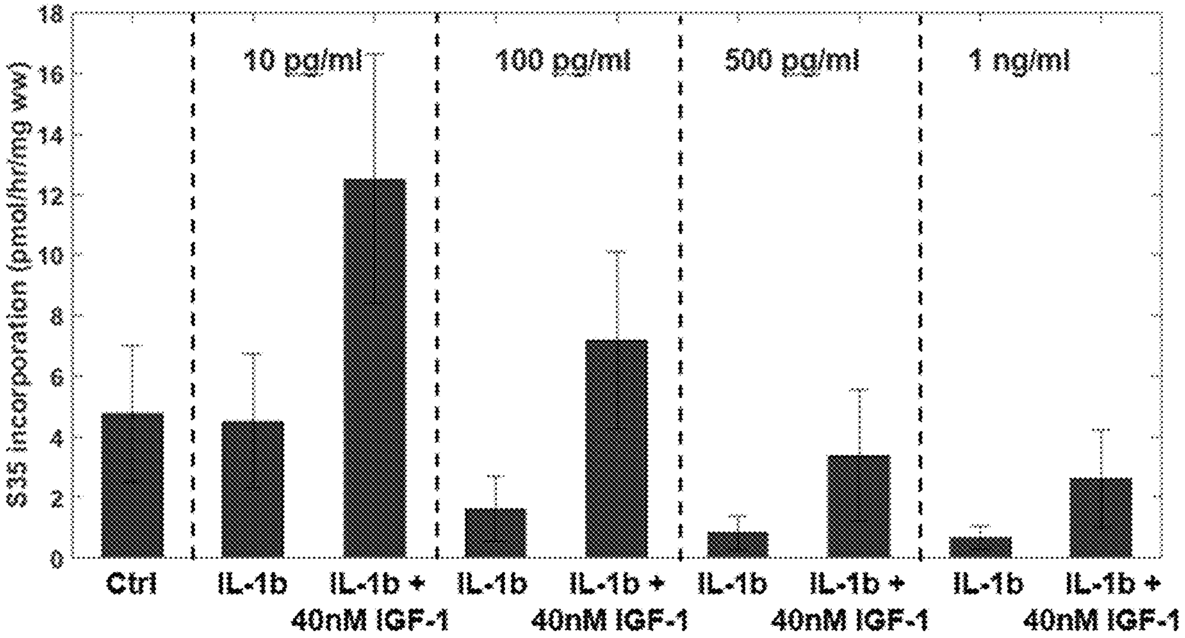

Experiment 5A (IL-1β Dose Response):

Results for cartilage from the 58 year old male donor are included in FIG. 6A, and FIG. 6B shows the results for cartilage from 68 year old male donor. Experimental groups (N=8 to 10 cartilage explants in each group): Untreated control (Ctrl in FIG. 6A and FIG. 6B), 10 pg/mL human IL-1β (10 pg/ml IL-1b in FIG. 6A and FIG. 6B), 10 pg/mL human IL-1β+40 nM IGF-1 (10 pg/ml IL-1b+40 nM IGF-1 in FIG. 6A and FIG. 6B), 100 pg/mL human IL-1β (100 pg/ml IL-1b in FIG. 6A and FIG. 6B), 100 pg/mL human IL-1β+40 nM IGF-1 (100 pg/ml IL-1b+40 nM IGF-1 in FIG. 6A and FIG. 6B), 500 pg/mL human IL-1β (500 pg/ml IL-1b in FIG. 6A and FIG. 10B), 500 pg/mL human IL-1β+40 nM IGF-1 (500 pg/ml IL-1b+40 nM IGF-1 in FIG. 6A and FIG. 6B), 1000 pg/mL human IL-1β (1 ng/ml IL-1b in FIG. 6A and FIG. 6B), 1000 pg/mL human IL-1β+40 nM IGF-1 (1 ng/ml IL-1b+40 nM IGF-1 in FIG. 6A and FIG. 6B). Media changes were performed every 2 days and the experiment was terminated after 8 days.

Chondrocyte biosynthesis rate (primarily aggrecan synthesis) was measured between days 6 and 8 of the experiment using a 35S-sulfate radiolabel. Statistics: 1-way ANOVA with post-hoc Tukey's HSD test.

Results from FIGS. 6A and 6B: 100 pg/ml, 500 pg/ml and 1000 pg/ml doses of human IL-1β cause a significant reduction in aggrecan biosynthesis compared to the untreated control. 40 nM free IGF-1 is able to completely rescue the biosynthesis loss caused by 100 pg/ml of human IL-1β. At 500 pg/ml and 1000 pg/ml doses of human IL-1β, adding 40 nM of free IGF-1 is less effective, and it only leads to a partial rescue of biosynthesis. Based on these experiments, 100 pg/ml of IL-1β was chosen as the optimal dose to simulate osteoarthritis in human cartilage explants and screen various drugs for disease modifying effects.

Experiment 5B (Fusion Protein Dose Response in the Presence of 100 pg/ml IL-1β):

This experiment was set up with cartilage explants from the 68 year old male donor ankle. Experimental groups (N=8 to 10 cartilage explants in each group): Untreated control (Ctrl in FIG. 6C), Continuous human IL-1β control (100 pg/ml dose added with every media change) (IL-1b in FIG. 6C), Continuous human IL-1β+continuous free IGF-1 control (100 pg/ml human IL-1β and 40 nM free IGF-1 dose added with every media change) (IL-1b+IGF1 FIG. 6C), Continuous human IL-1β+(+9GFP)-$(GGGGS)_4$-(IGF-1) (SEQ ID NO: 7) 500 nM single dose (100 pg/ml human IL-1β added with every media change; Single 500 nM fusion protein dose added on Day 0) (IL-1b+0.5 μM Flex-1 in FIG. 6C), Continuous human IL-1β+(+9GFP)-$(GGGGS)_4$-(IGF-1) (SEQ ID NO: 7) 1 μM single dose (100 pg/ml human IL-1β added with every media change; Single 1 μM fusion protein dose added on Day 0) (IL-1b+1 μM Flex-1 in FIG. 6C), Continuous human IL-1β+(+9GFP)-$(EAAAK)_3$-(IGF-1) (SEQ ID NO: 8) 500 nM single dose (100 pg/ml human IL-1β added with every media change; Single 500 nM fusion protein dose added on Day 0), Continuous human IL-1β+(+9GFP)-$(EAAAK)_3$-(IGF-1) (SEQ ID NO: 8) 1 μM single dose (100 pg/ml human IL-1β added with every media change; Single 1 μM fusion protein dose added on Day 0) (IL-1b+1 μM Rig-1 in FIG. 6C).

Chondrocyte biosynthesis rate (primarily aggrecan synthesis) was measured between days 6 and 8 of the experiment using a 35S-sulfate radiolabel. Statistics: 1-way ANOVA with post-hoc Tukey's HSD test.

Figure 6C:
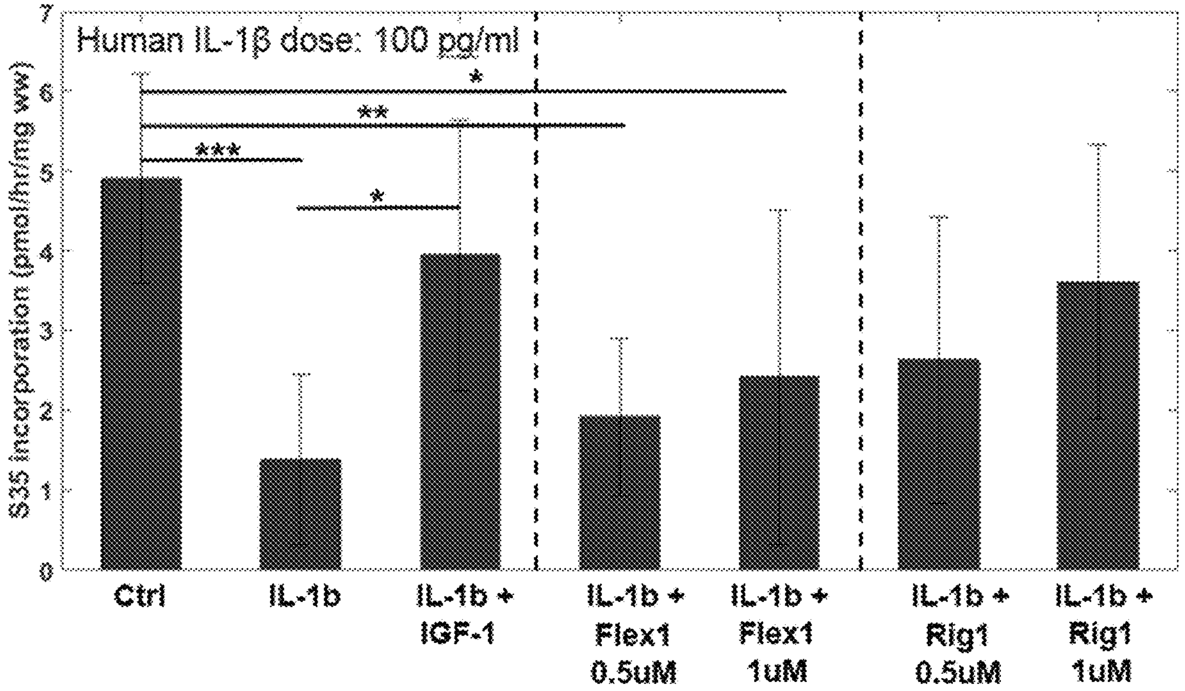
Figure 7:
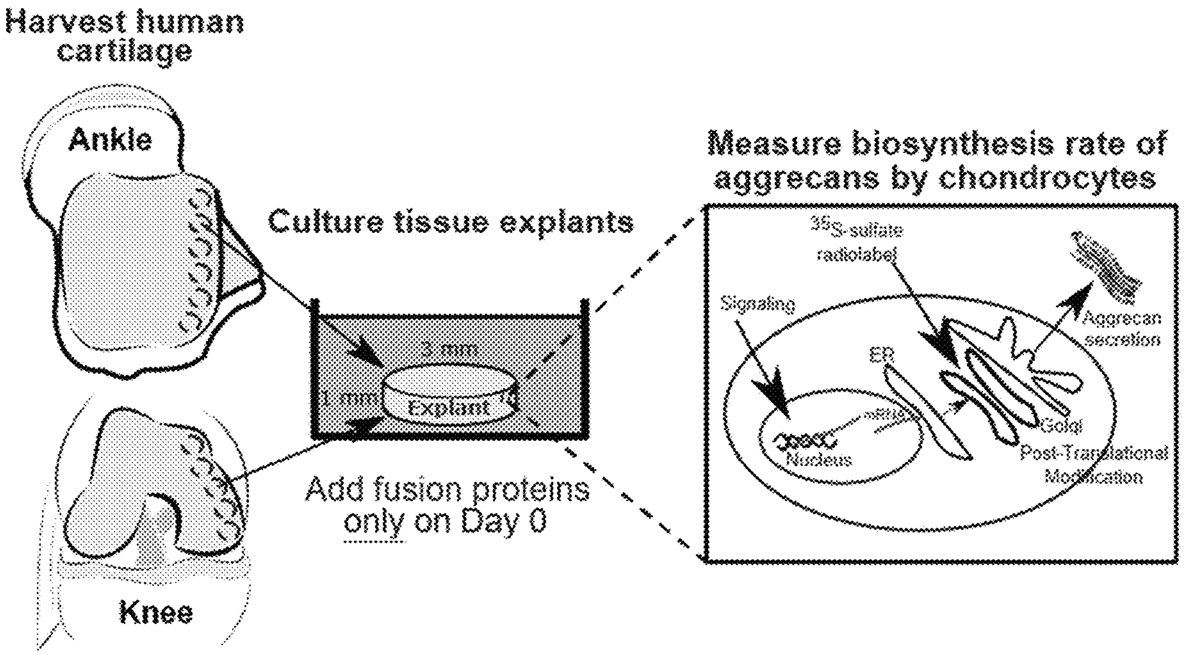
FIG. 7 shows a schematic for testing the bioactivity of +9GFP-IGF-1 fusion proteins in cartilage. Cartilage explants were harvested from human knee and ankle joints. Single doses of the +9GFP-IGF-1 fusion protein variants were added to the explants at the start of the experiments, and they were cultured for 3, 7 or 15 days. The aggrecan biosynthesis rate of the explants was measured using a 35S radiolabel, and the biosynthesis rate for the fusion protein treatment groups were compared with the rates for an untreated control group and a group with continuous free IGF-1 dosing.

Results from FIG. 6C: 100 pg/ml dose of human IL-1β cause a significant reduction in aggrecan biosynthesis compared to the untreated control. 40 nM free IGF-1 is able to completely rescue the biosynthesis loss caused by 100 pg/ml of human IL-1β. Both dose levels of (+9GFP)-$(EAAAK)_3$-(IGF-1) (SEQ ID NO: 8) are also able to rescue the biosynthesis loss caused by 100 pg/ml of human IL-1β.

Example 3: Further Characterization of Fusion Proteins with +9 GFP and IGF-1 Domains

Materials and Methods

Fusion Protein Design

Figure 8A:
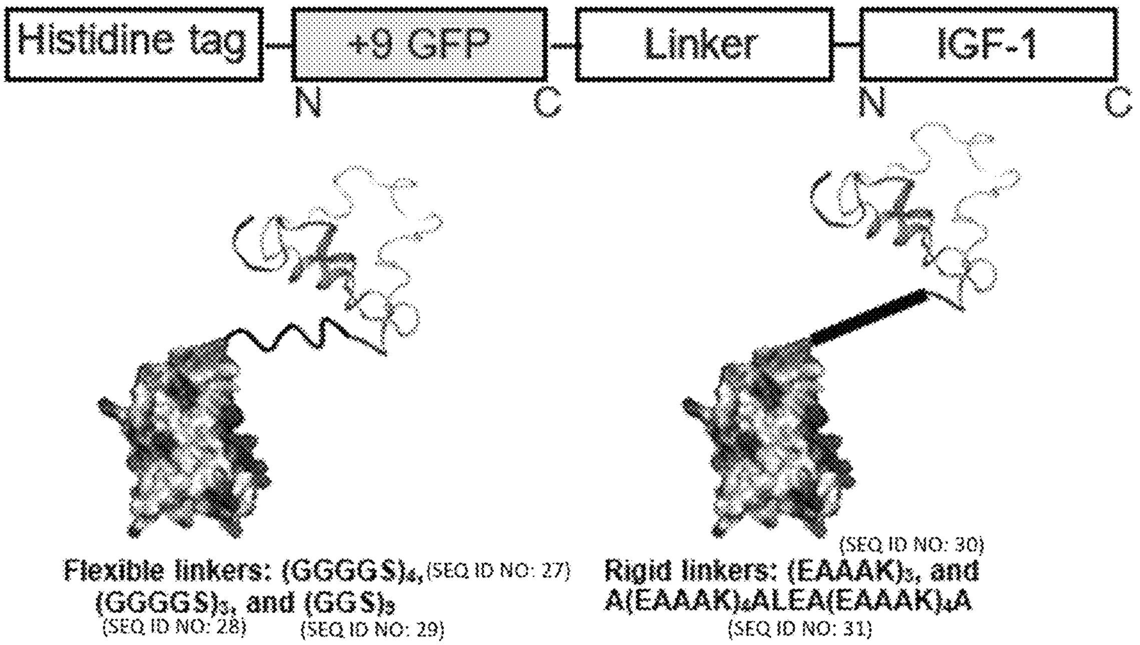
FIGS. 8A-8C show the design, synthesis and characterization of +9GFP-IGF-1 fusion proteins. Fusion proteins were designed with +9 GFP at the N-terminus and IGF-1 at the C-terminus (FIG. 8A). Five different variants were designed with different flexible and rigid linkers. A sixth variant with no linker was also included. All six fusion proteins have an N-terminus 6×His-tag.

Five peptide linkers (three flexible ($(GGGGS)_4$ (SEQ ID NO: 27), $(GGGGS)_3$ (SEQ ID NO: 28), $(GGS)_9$ (SEQ ID NO: 29)) and two rigid ($(EAAAK)_3$ (SEQ ID NO: 30), A$(EAAAK)_4$ALEA$(EAAAK)_4$A (SEQ ID NO: 31))) were chosen and fusion proteins were designed with an N-terminus His6 tag, followed by +9 GFP, the peptide linker and IGF-1 (FIG. 8A). A fusion protein without a peptide linker was also designed. The codon sequences for each fusion protein were optimized for *E. coli* and inserted into the pET-29b(+) vector.

Protein Expression and Purification

Figure 8B:
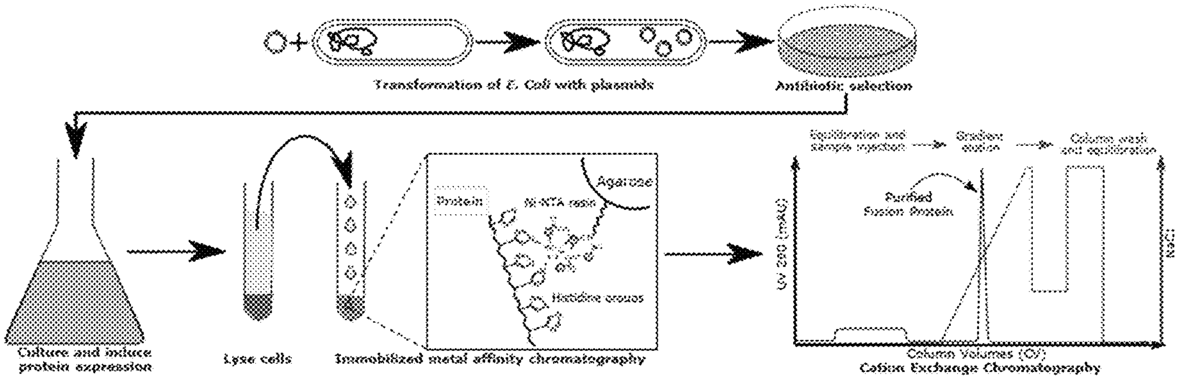

The schematic for protein expression and purification is shown in FIG. 8B. For each fusion protein, BL21 Star (DE3)-competent *E. coli* cells were transformed with the appropriate plasmid and a well-isolated colony was grown overnight in 10 mL Luria-Bertani (LB) broth containing kanamycin at 37° C. This starter culture was then diluted into 1 liter of LB broth with kanamycin and grown at 37° C. until $OD_{600}$ 0.8-1. Following this, fusion protein expression was induced with 1 mM isopropyl-β-D-1-thiogalactopyranoside (IPTG)(GoldBio) and cultures were sustained at 16° C. with shaking for 20 hours. Cells were collected by centrifugation at 4000 rpm for 15 minutes at 4° C., and the cell pellets were frozen at −80° C.

The cell pellets were defrosted and resuspended in 25 mL lysis buffer (100 mM tris(hydroxymethyl)-aminomethane (Tris)-HCl pH 8.0, 20% glycerol, 1M NaCl, half tablet of complete EDTA-free protease inhibitor pellet (Roche), 0.4 mM phenylmethane sulfonyl fluoride (PMSF; Sigma-Aldrich) and 5 mM tris(2-carboxyethyl)phosphine (TCEP; GoldBio)). The resuspended cells were lysed by sonication (5 min total time; 3 s on, 2 s off) and centrifuged at 12,500 rpm for 60 minutes. The expressed fluorescent proteins were present in the supernatant and this was collected for purification.

The fusion proteins were first purified using immobilized metal affinity chromatography. 3 mL of HisPur™ nickel nitriloacetic acid (nickel-NTA) resin slurry (ThermoFisher; 50% slurry in 20% ethanol) was centrifuged for 2 minutes at 700 g and the supernatant was discarded. The settled resin (1.5 mL) was washed twice by resuspending in 15 mL lysis buffer, centrifuging at 700 g and discarding the supernatant. The supernatant from the cell lysis step (containing the expressed fusion proteins) was added to the washed nickel-NTA resin and mixed on an end-over-end rotator in the cold room for 90 minutes. The resin was washed twice with 15 mL of lysis buffer before bound protein was eluted with elution buffer ((100 mM tris(hydroxymethyl)-aminomethane (Tris)-HCl pH 8.0, 20% glycerol, 0.5 M NaCl, 5 mM TCEP (GoldBio), 200 mM imidazole). The resulting protein fraction was further purified on a 5 ml Hi-Trap HP SP (GE Healthcare) cation exchange column using an Akta Pure FPLC. An NaCl gradient (from 0-1 M) was used to elute the fusion protein from the HP SP column. The protein containing fractions were analyzed in an SDS-PAGE gel, and fractions containing pure fusion protein were combined.

Depending on the volume, the combined fraction was concentrated using either a Centricon® Plus-70 centrifugal unit (10 kDa cutoff; Millipore) or an Amicon®Ultra-15 centrifugal unit (10 kDa cutoff; Millipore) centrifuged at 3,500 g. The concentrated proteins were sterile-filtered through a 0.2 μm pore size sterile syringe filter (VWR), quantified with the Reducing Agent Compatible Bicinchoninic acid (BCA) assay (Pierce Biotechnology), snap-frozen in liquid nitrogen and stored in aliquots at −80° C. The concentrated, sterile filtered proteins were analyzed in an SDS-PAGE gel followed by a western blot with polyclonal anti-IGF-1 antibody (Abcam, Cambridge, MA).

Human Cartilage Explant and Chondrocyte Harvest

Seven human knee joint distal femurs and twenty-seven ankle joints obtained from twenty different donors were obtained from donor banks (Gift of Hope Organ and Tissue Donor Network (Itasca IL), LifeNet Health (Virginia Beach VA), and National Disease Research Interchange (Philadelphia PA)). Eight ankles and one knee were used for harvesting chondrocytes, and explants were harvested from the remaining joints. The age of the donors and the Collins grade of the joints are tabulated in Table 4. All procedures were approved by the Rush University Medical Center Institutional Review Board (ORA Number: 08082803-IRB01-AM01) and the Committee on the Use of Humans as Experimental Subjects at MIT. Femoral cartilage plugs (3 mm diameter) were harvested using a biopsy punch. Explants that were thicker than 1 mm were trimmed down to 1 mm. All explants were equilibrated for 48 to 72 hours (37° C., 5% $CO_2$) in low glucose (1 g/L) DMEM which was supplemented with 100 U/mL penicillin, 100 mg/mL streptomycin, 0.25 mg/mL amphotericin, 10 mM HEPES buffer, 0.1 mM nonessential amino acids (NEAA), 0.4 mM proline and 20 mg/mL ascorbic acid.

TABLE 4

List of human joints used in this study.

Figure 9A:
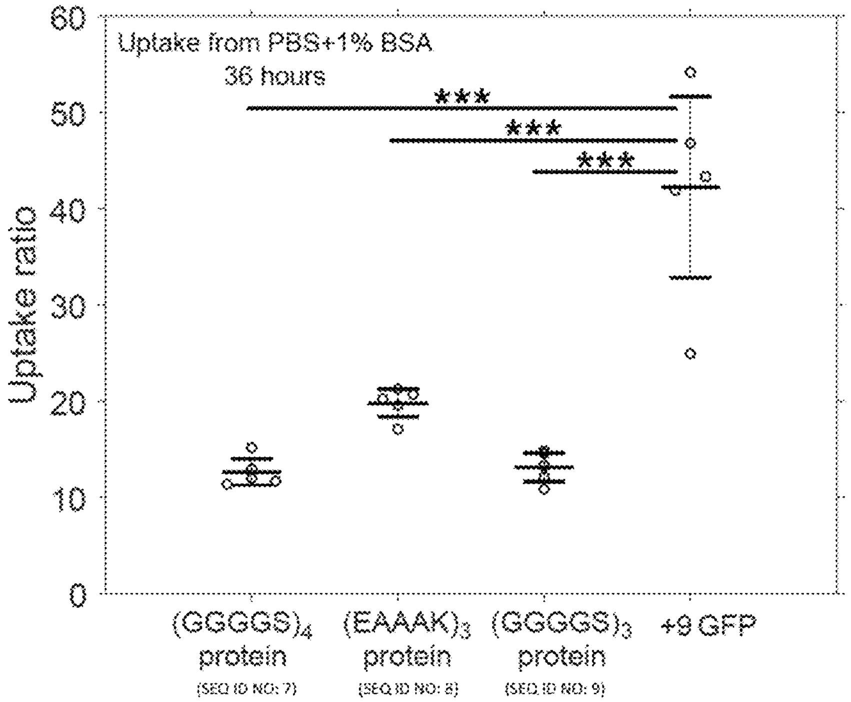
FIGS. 9A-9B show the uptake ratio of +9GFP-IGF-1 fusion proteins in human cartilage. Human ankle cartilage explants were incubated in 1 μM solutions of +9GFP and +9GFP-IGF-1 fusion proteins dissolved in PBS+1% BSA. 36 hour uptake ratios are shown in FIG. 9A and 108 hour uptake ratios are shown in FIG. 9B. N=5 cartilage explants (matched for joint region) from 1 human donor were used for each condition and the individual data points, mean and 95% confidence interval are reported; *: $p<0.05$; : $p<0.01$; *: $p<0.001$.
Figure 9B:
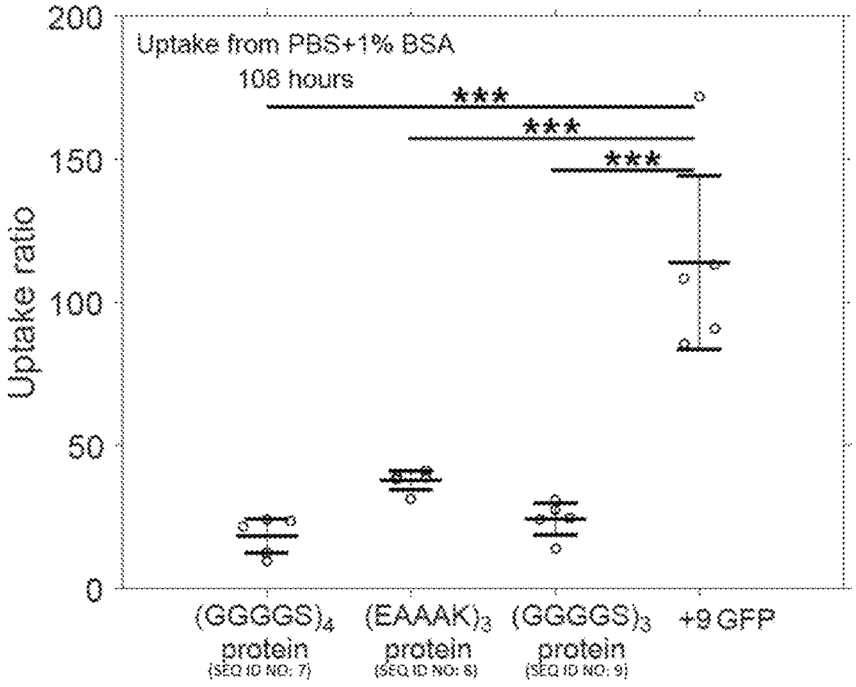
Figure 10A:
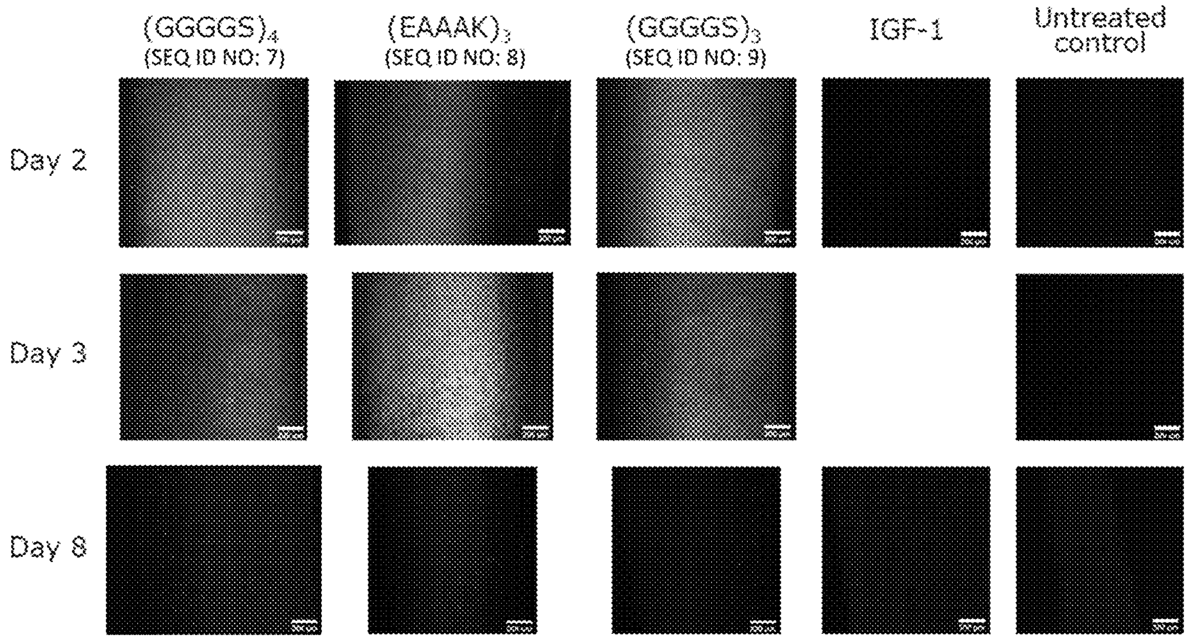
FIGS. 10A-10B show the fusion protein penetration in human knee cartilage explants (23-year-old male donor).
Figure 10B:
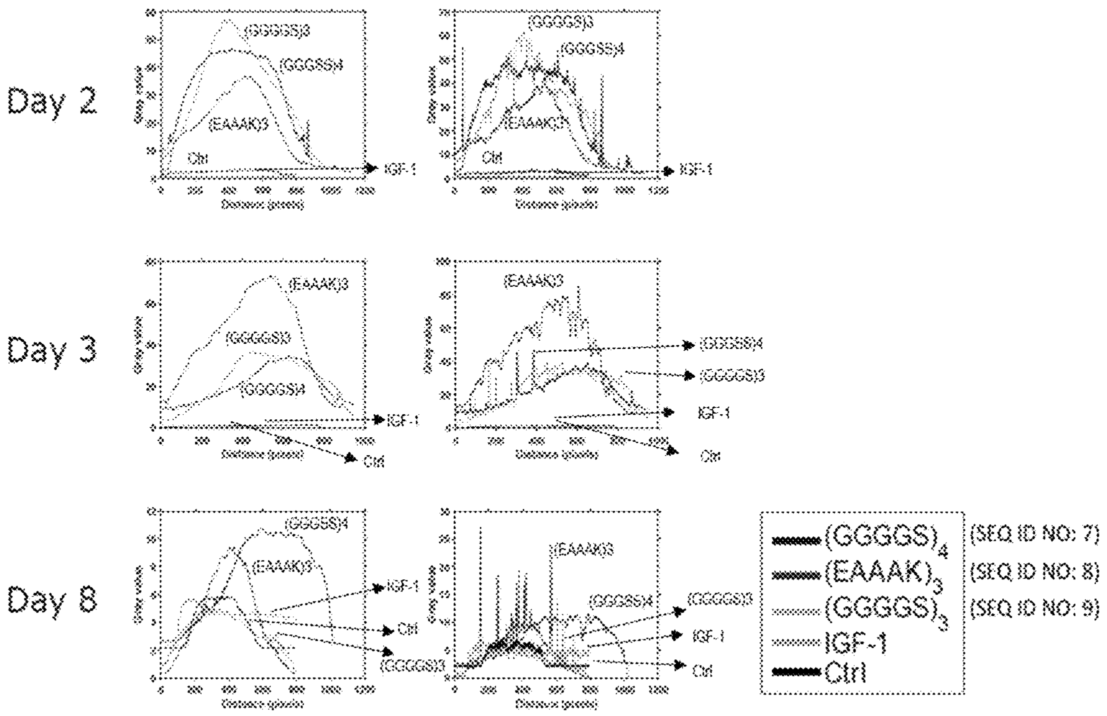
Figure 11A:
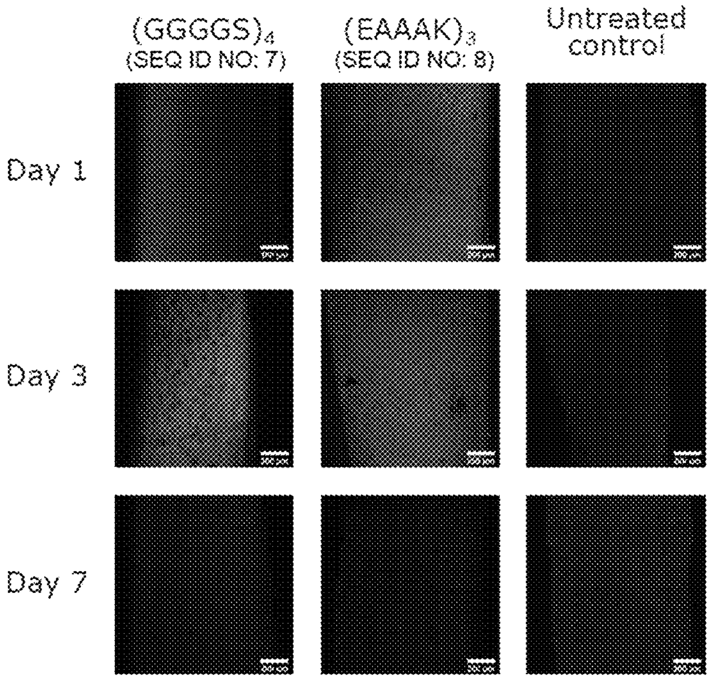
FIGS. 11A-11B show the fusion protein penetration in human ankle cartilage explants (36-year-old female donor).
Figure 11B:
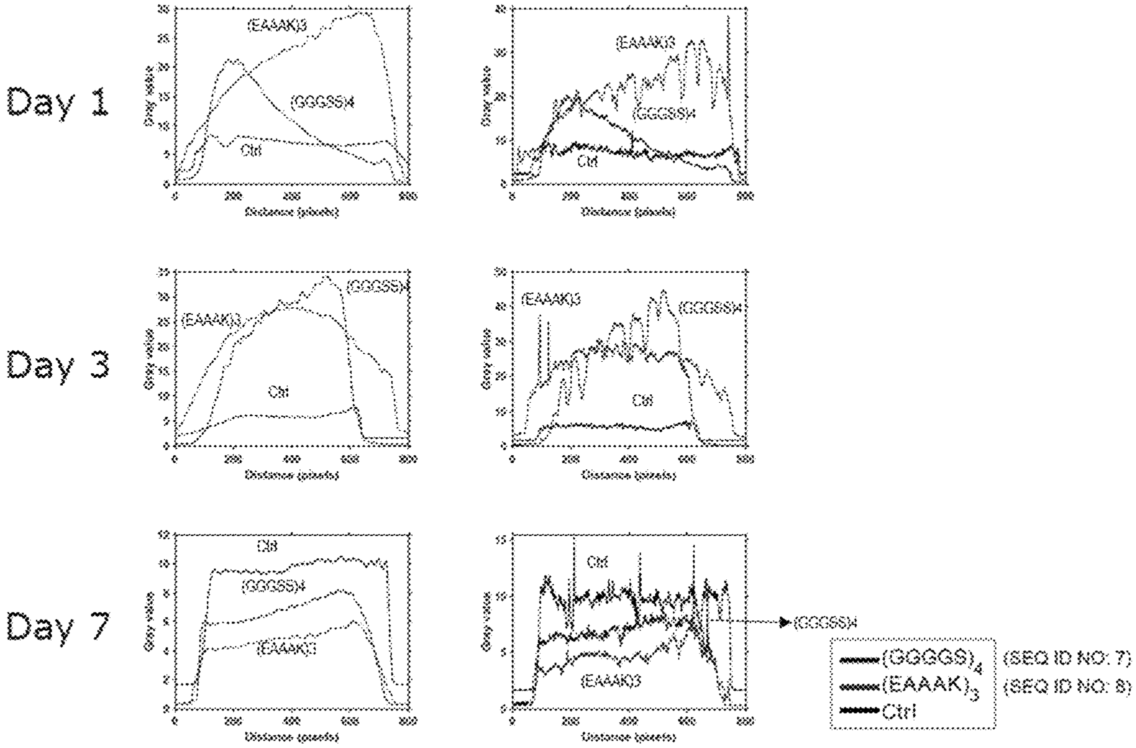
Figure 12A:
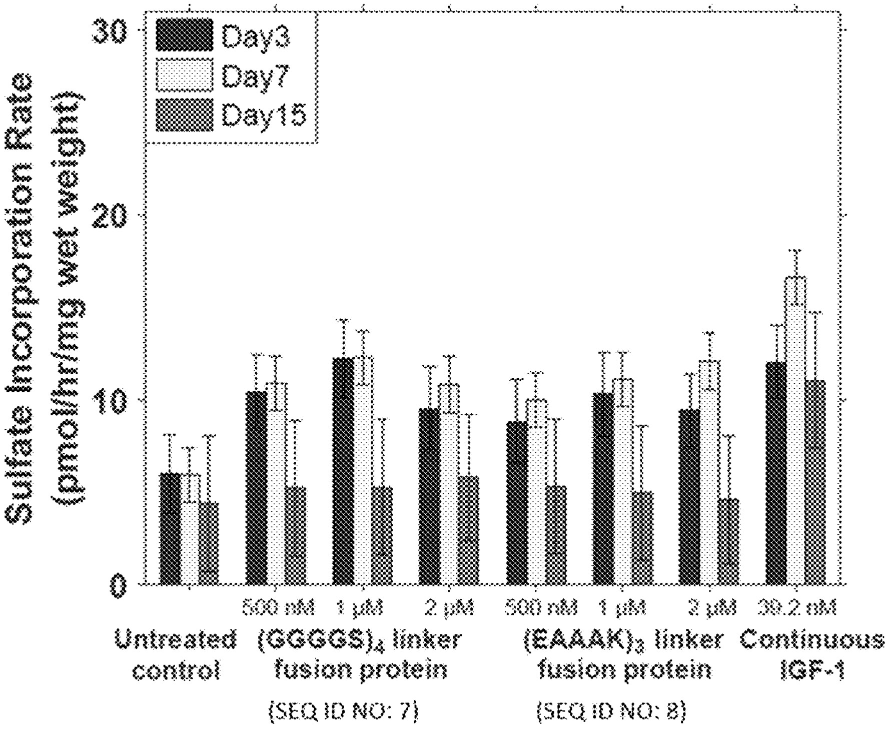
FIGS. 12A-12B show explant biosynthesis, as measured by the normalized sulfate incorporation rate, in dose response experiments with +9GFP-IGF-1 fusion protein variants. The biosynthesis rate during the last 48 to 72 hours of each experiment was normalized with the wet weights of the explants. The results for human ankle cartilage are shown in FIG. 12A. Explants from 1 donor (N=7 to 9 explants/condition) were used for the 3 day experiment, 6 donors (N=6 to 12 explants/condition/donor) for the 7 day experiment and 3 donors (N=6 to 8 ex-plants/condition/donor) for the 15 day experiment. The results for human knee cartilage are shown in FIG. 12B. Explants from 2 donors (N=5 explants/condition/donor) were used for the 3 day experiment, 3 donors (N=5 to 6 explants/condition/donor) for the 7 day experiment and 1 donor (N=6 explants/condition) for the 15 day experiment. All bars represent least squares means with 95% confidence intervals. Statistical comparisons are shown in Tables 6 and 7.
Figure 12B:
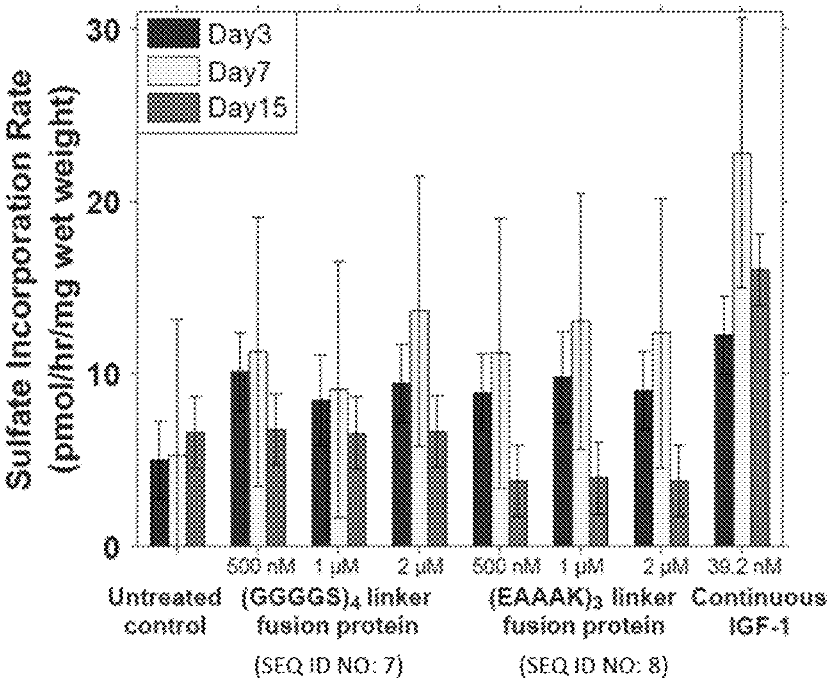
Figure 14A:
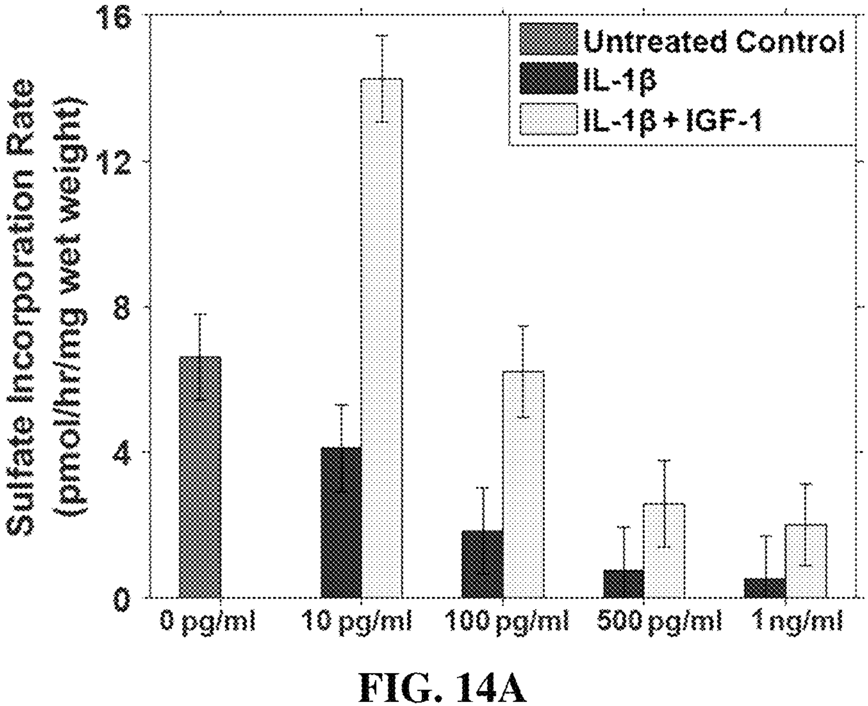
FIGS. 14A-14B show the normalized sulfate incorporation rate measured during day 6 to 8 of an 8-day dose response experiment. Human ankle cartilage explants from a 58-year-old male donor (FIG. 14A) and a 68-year-old male donor (FIG. 14B) were treated with 10 pg/ml to 1 ng/ml doses of human IL-10 either individually or in combination with 300 ng/ml IGF-1. Untreated control groups were included in both experiments. All bars represent least squares means with 95% confidence intervals. N=9 to 10 explants/condition in FIG. 14A and N=6 to 8 explants/condition in FIG. 14B.
Figure 14B:
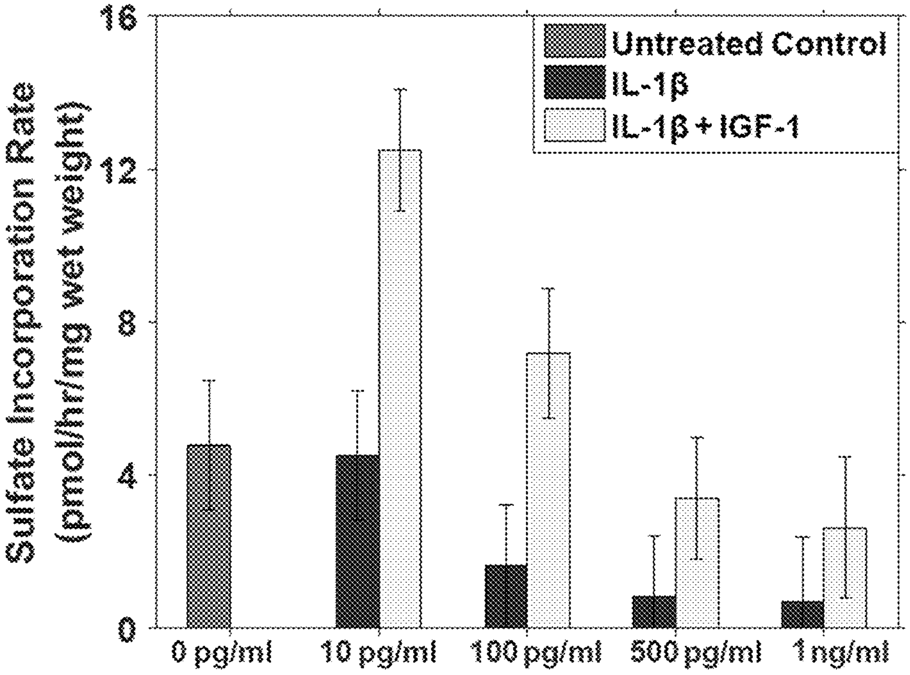
Figure 15A:
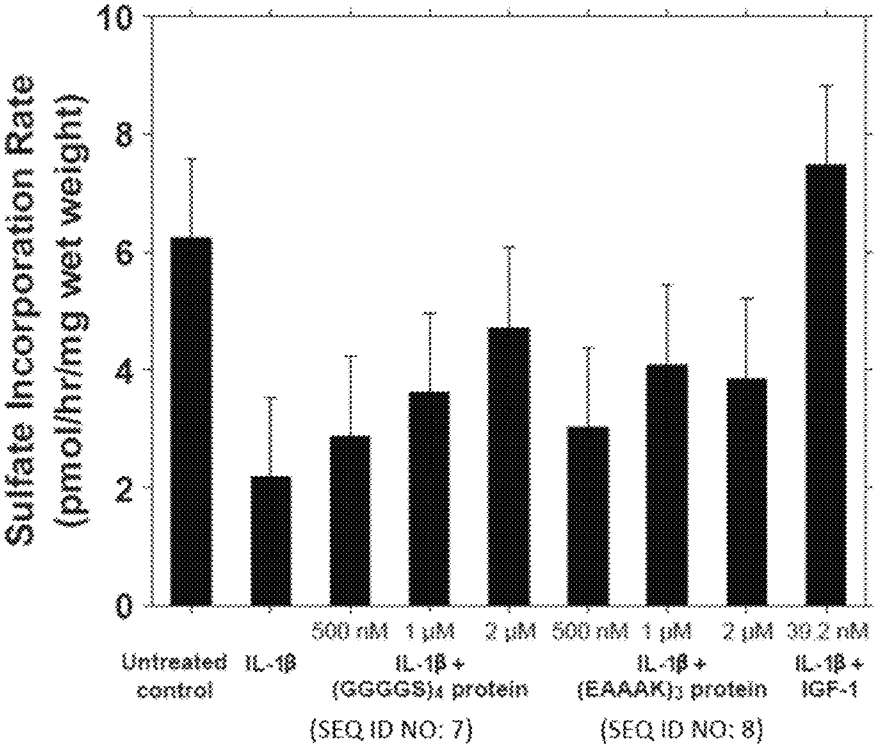
FIGS. 15A-15D show the dose response of +9GFP-IGF-1 fusion proteins in a cytokine challenge model of post-traumatic osteoarthritis (PTOA). Human ankle cartilage explants were treated with a continuous 100 pg/ml dose of IL-1β and single doses of fusion proteins. An untreated control and a group with continuous IGF-1+IL-1β were included.
Figure 15B:
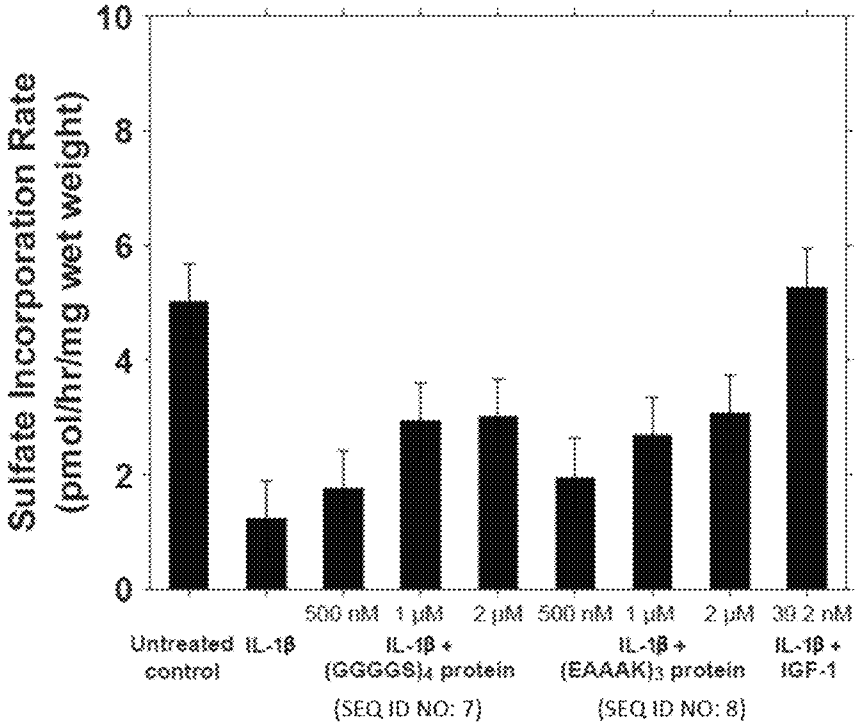
Figure 15C:
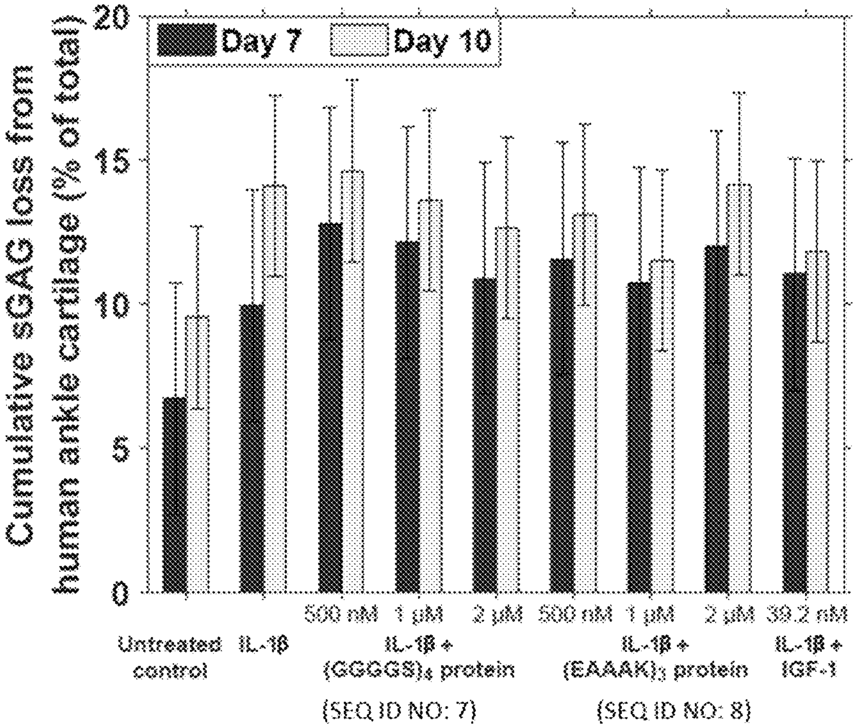
Figure 15D:
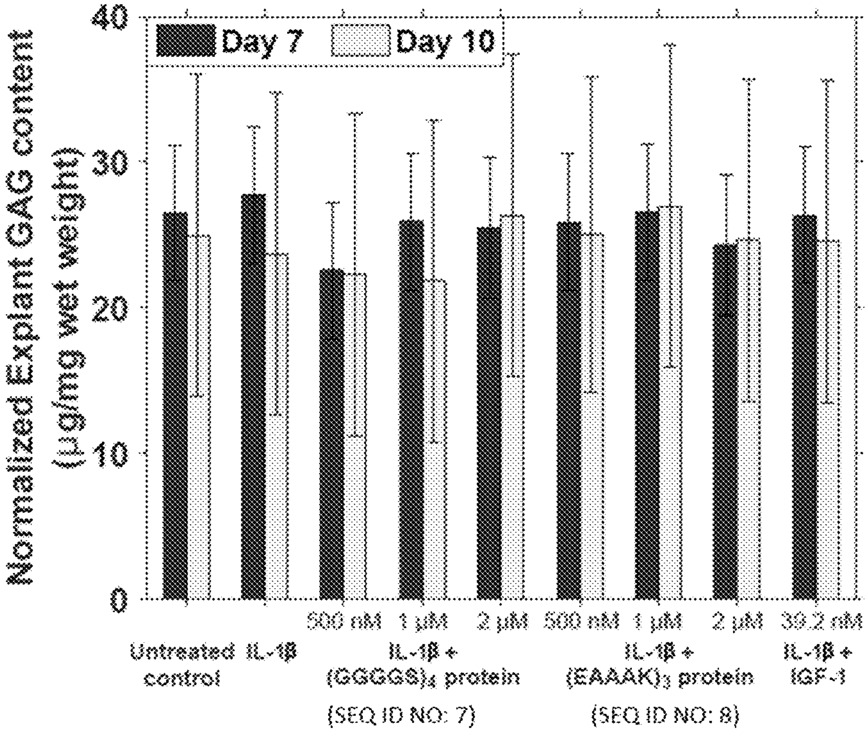
Figure 18A:
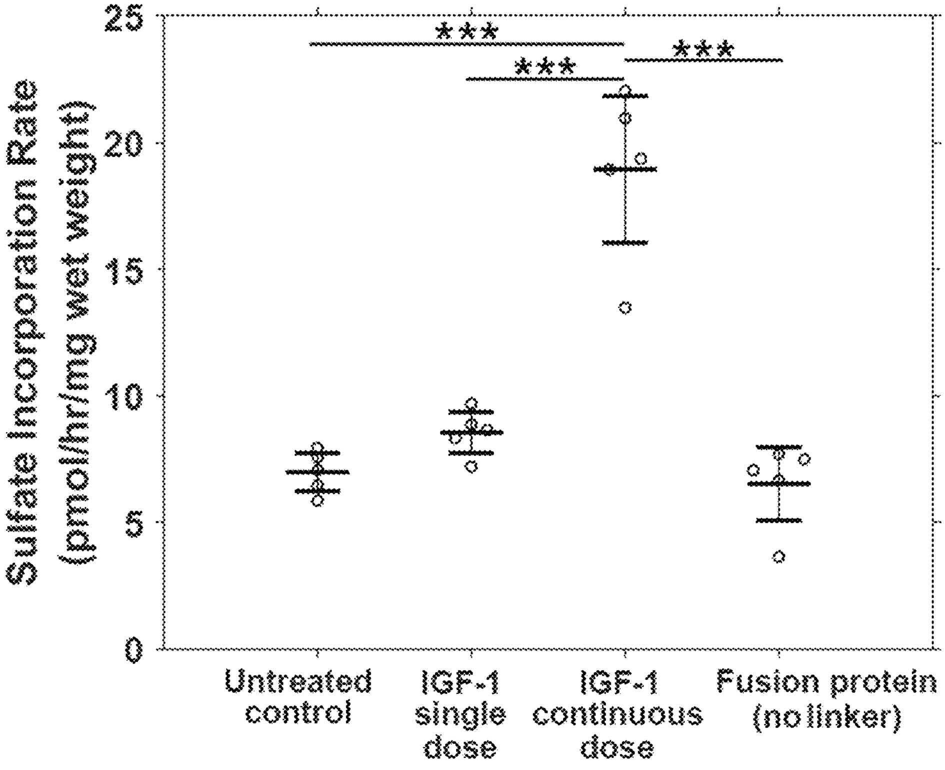
FIGS. 18A-18B show the normalized sulfate and proline incorporation rate measured during days 6 to 8 of an 8-day dose response experiment. Groups of 5 ankle cartilage explants were treated with a single 300 ng/ml (39.2 nM) dose of IGF-1, continuous doses (39.2 nM) of IGF-1 or a single dose (39.2 nM) of the +9GFP-IGF-1 fusion protein with no linker. An untreated control group with 5 explants was also included in the experiment. Normalized sulfate incorporation rates are shown in FIG. 28A and normalized proline incorporation rates are shown in FIG. 18. The individual data points, mean values and 95% confidence intervals are reported; *: $p<0.05$; : $p<0.01$; *: $p<0.001$.
Figure 18B:
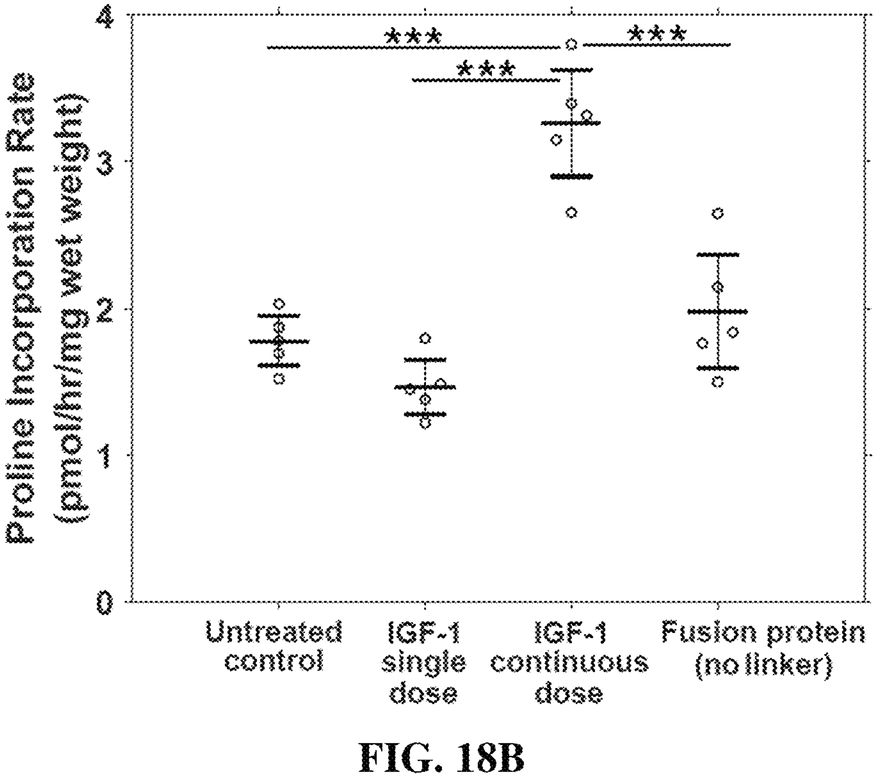
Figure 19A:
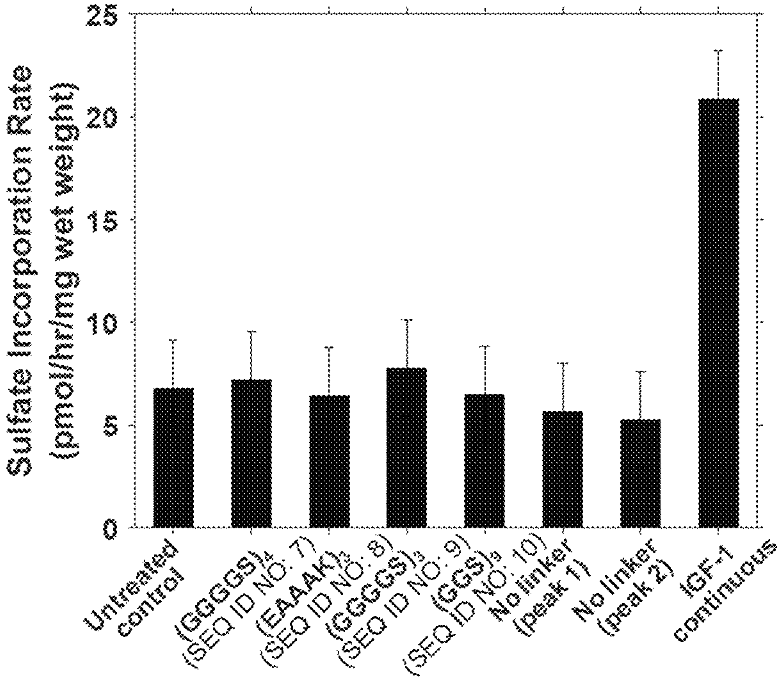
FIGS. 19A-19B show results from testing the effect of fusion proteins on the normalized sulfate and proline incorporation rates of human ankle cartilage. Groups of 7 explants from one human donor were treated with single doses (39.2 nM) of +9GFP-IGF-1 fusion proteins. An untreated control group and a group with continuous 39.2 nM doses of free IGF-1 were also included in the experiment.
Figure 19B:
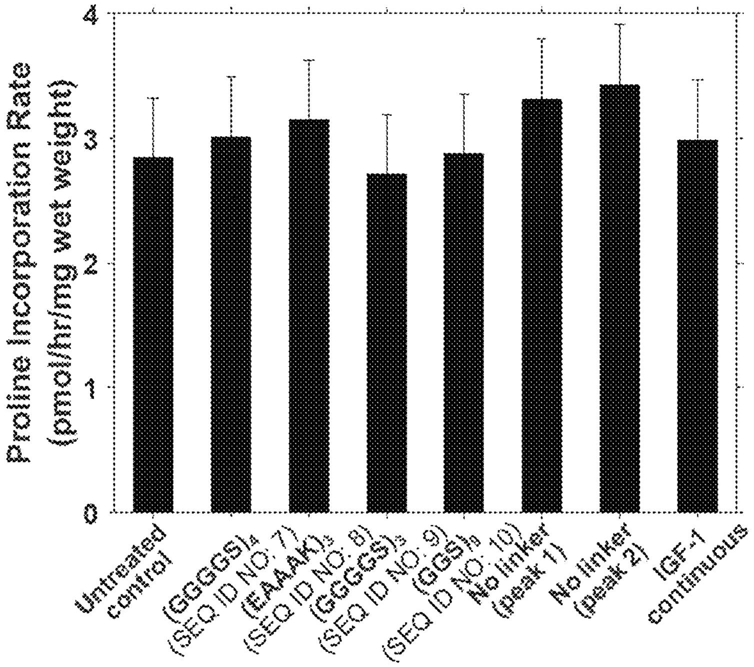
Figure 20:
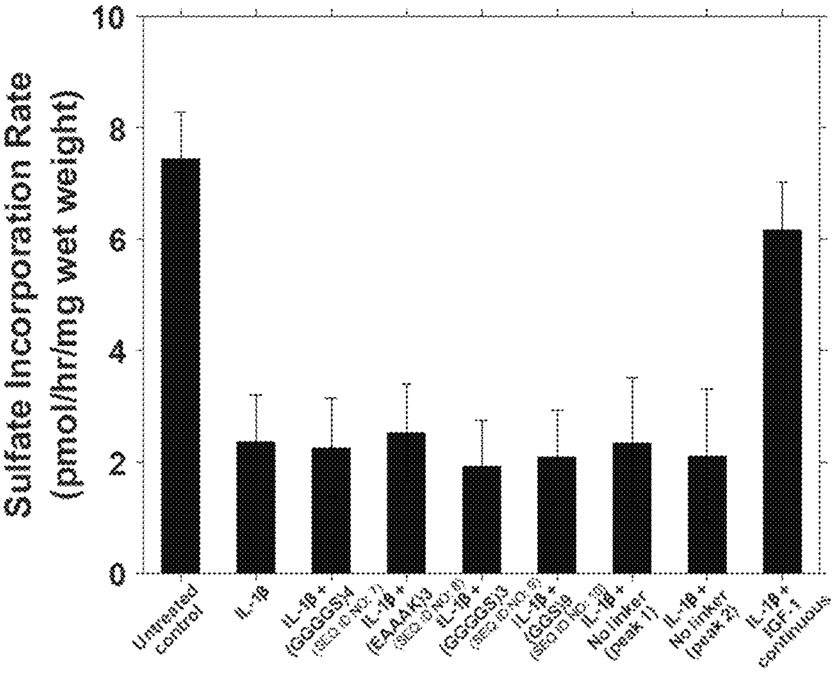
FIG. 20 shows results from testing the effect of fusion proteins in a cytokine challenge model of PTOA. Groups of explants from two human donors were treated continuously with 10 ng/ml mouse IL-1β. Treatment groups received single doses (39.2 nM) of +9GFP-IGF-1 fusion proteins or continuous doses (39.2 nM) of IGF-1. An untreated control group was also included in the experiment. The sGAG biosynthesis rate of the explants was measured between day 7 and day 9 of the experiment and normalized using the wet weights. Only the continuous free IGF-1 treatment could rescue the biosynthesis loss caused by IL-1β treatment. (N=2 donors; 3 to 8 explants/condition/donor; Bars represent least squares mean values with 95% confidence intervals.)

| Joint # | Sex | Age | Joint type | Modified Collins Grade | FIGS. |
|---|---|---|---|---|---|
| 1. | Female | 58 | Ankle | 1 | FIG. 18A-18B |
| 2. | Male | 57 | Knee | (NDRI) | |
| 3. | Female | 53 | Ankle | 1 | FIGS. 19A-19B, 20 |
| 4. | | | Ankle | 1 | FIGS. 19A-19B, 20 |
| 5. | Male | 66 | Ankle | 1 | FIG. 20 |
| 6. | Male | 77 | Ankle | 2 | |
| 7. | Male | 23 | Knee | (LNH) | FIGS. 10A-10B, 12B |
| 8. | Male | 66 | Ankle | 0 | FIGS. 9A-9B |
| 9. | | | Ankle | 0 | FIG. 12A |
| 10. | Male | 55 | Ankle | 1 | |
| 11. | | | Ankle | 1 | |
| 12. | Male | 38 | Knee | (LNH) | FIG. 12B |
| 13. | Male | 58 | Ankle | 1 | FIGS. 14A-14B |
| 14. | | | Ankle | 1 | FIG. 12A |
| 15. | Male | 68 | Ankle | 1 | FIGS. 14A-14B |
| 16. | | | Ankle | 1 | FIGS. 15A, 15C, 15D |
| 17. | Female | 60 | Ankle | 0 | FIG. 12A |
| 18. | | | Ankle | 0 | FIGS. 15B, 15C, 15D |
| 19. | Female | 69 | Ankle | 1 | FIGS. 15B, 15C, 15D |
| 20. | Male | 67 | Ankle | 1 | |
| 21. | | | Ankle | 1 | |
| 22. | Female | 69 | Knee | 1 | FIG. 12B |
| 23. | | | Knee | 1 | |
| 24. | Male | 59 | Ankle | 1 | |
| 25. | | | Ankle | 1 | |
| 26. | Female | 36 | Ankle | 0 | FIGS. 12A, 11A-11B |
| 27. | | | Ankle | 0 | FIGS. 15A, 15C, 15D |
| 28. | Male | 70 | Ankle | 1 | FIGS. 15A, 15C, 15D |
| 29. | | | Ankle | 2 | FIG. 12A |
| 30. | Male | 80 | Ankle | 1 | FIG. 12A |
| 31. | | | Ankle | 1 | FIGS. 15A, 150, 15D |
| 32. | | | Knee | 2 | |
| 33. | | | Knee | 2 | |
| 34. | Male | 63 | Ankle | 1 | FIGS. 15A, 15C, 15D |

To extract live chondrocytes, solutions of collagenase (1.25 mg/mL) and pronase (2 mg/mL) were prepared in low glucose DMEM with 5% fetal bovine serum (FBS), 100 U/mL penicillin, 100 mg/mL streptomycin, 0.25 mg/mL amphotericin, 10 mM HEPES buffer, 0.1 mM nonessential amino acids (NEAA) and 0.4 mM proline. Cartilage tissue slices were harvested from human ankles, washed with PBS and incubated in the pronase solution (37° C., 5% $CO_2$) for 1 hour. This was followed by an overnight incubation in the collagenase solution at 37° C. and 5% $CO_2$. The final solution was then passed through a 70 μm filter and a 40 μm filter to remove any undigested cartilage fragments. The filtrate was centrifuged at 400 g for 8 minutes and the pellet was resuspended in 50 mL PBS. Viable cell counts were obtained from aliquots of this suspension using a hemocytometer and Trypan blue. The cells were then centrifuged out of the suspension (400 g, 8 minutes), resuspended in freezing medium (FBS with 5% DMSO) and stored in liquid nitrogen until use.

Quantitative Uptake of Fusion Proteins in Human Cartilage

Cartilage explants that had been equilibrated in culture medium post-harvest were transferred to sterile PBS and allowed to equilibrate for 1 hour before the start of the experiments. Sterile PBS solutions containing 1% bovine serum albumin (BSA) were prepared. Following this, 1 μM solutions of (+9GFP), (+9GFP)-$(GGGGS)_4$-(IGF-1) (SEQ ID NO: 7), (+9GFP)-$(EAAAK)_3$-(IGF-1) (SEQ ID NO: 8) and (+9GFP)-$(GGGGS)_3$-(IGF-1) (SEQ ID NO: 9) were prepared. The BSA was included in the PBS to minimize loss of GFPs in the solution caused by non-specific binding to the plasticware. Since the main function of the albumin in these experiments was only to prevent such non-specific binding in the external solution, BSA instead of human serum albumin (HSA) was used to maintain consistency with previous experimental techniques. Groups of 5 cartilage explants (matched for position along the joint surface) were assigned to each treatment group and to the untreated control groups. Each explant was separately incubated in 250 μL solutions (GFP solutions in PBS+1% BSA for treatment groups and PBS+1% BSA for untreated controls) in sterile polypropylene vials for 36 hours or for 4.5 days (37° C., 5% $CO_2$). Standard 96-well cell culture plates were not used because the +9 GFP domain could stick to polystyrene even in the presence of BSA, leading to a loss of protein. In contrast, use of polypropylene with 1% BSA enabled complete recovery of fluorescence.

At the end of the incubation period, cartilage explants were washed with PBS and transferred to a solution of 10×PBS+1% BSA for desorption. At the same time, the fluorescence of the absorption bath was measured using a plate reader (Synergy H1, Biotek Instruments Inc.) (excitation: 485 nm, emission: 528 nm). This was used along with a standard curve to obtain the concentration of GFP left behind in the absorption bath. At the end of the desorption in 10×PBS+1% BSA, cartilage explants were weighed, and the fluorescence of the desorption bath was measured. This fluorescence measurement was used with a standard curve and the explant wet weights to calculate the concentration of GFP inside cartilage explants (mol/mg wet weight). The uptake ratio was calculated as the ratio of GFP concentration inside cartilage (mol/mg wet weight) to the final absorption bath concentration (mol/mL).

Fusion Protein Penetration into Cartilage

Human cartilage explants were cultured in ultra-low attachment cell culture plates (Corning) in 1 μM solutions of fusion proteins dissolved in low glucose (1 g/L) DMEM supplemented with 2 mM L-glutamine, 100 U/mL penicillin, 100 mg/mL streptomycin, 0.25 mg/mL amphotericin, 10 mM HEPES buffer, 0.1 mM nonessential amino acids (NEAA) and 0.4 mM proline (37° C., 5% $CO_2$). Fusion proteins were added only at the start of the experiment, and fresh media without fusion proteins was replenished every 2 to 3 days. An untreated control group and a treatment group with continuous dosage of free IGF-1 were also included in the experiments. Explants were taken out of culture at different time points and washed with PBS for approximately 60 minutes (to wash out any culture medium). These were then sectioned longitudinally into ~100 μm slices and washed once again with PBS.

Explant slices were imaged at 10× magnification using a confocal microscope (Olympus FluoView FV1000), and Z-stacks were obtained with a voxel depth of 4.22 μm. 3D cartilage Z-stacks were flattened to 2D using the Z project function available in the Fiji software package. During imaging, some cartilage explants were too large to fit into the field of view of the confocal microscope. In these cases, two overlapping Z-stacks were captured and combined using the Stitching plugin available in Fiji (Preibisch et al., Bioinformatics 25(11):1463-1465 (2009)) before performing 2D Z projections.

Dose Response of Fusion Proteins in Human Cartilage

Cartilage explants that were equilibrated in culture medium post-harvest were transferred to ultra-low attachment cell culture plates (Corning) for dose response experiments. All experiments were carried out in low glucose, serum free medium (same composition as equilibration medium). Previous studies studying the effects of IGF-1 on cartilage explants have used doses ranging from 10 ng/ml to 300 ng/ml. Based on these, 300 ng/ml (equivalent to 39.2 nM) of free recombinant human IGF-1 (PeproTech, Rocky Hill, NJ) was used as the positive control.

Since each fusion protein had one IGF-1 domain, equivalent doses (39.2 nM) of these were tested. In addition to this, 500 nM, 1 μM and 2 μM doses of fusion proteins were also tested. In all cases, only a single dose of the fusion proteins was added at the start of the experiment, and media changes were carried out without fusion proteins once every 2 to 3 days thereafter. In contrast, continuous doses of free IGF-1 were used for the positive control. An untreated control group was also included in the experiments. Experiments were terminated at 3-day, 7-day and 15-day time points. Outcome measures included the biosynthesis rate of sulfated glycosaminoglycans (sGAG), explant metabolic rate, sGAG loss to the culture medium and the explant sGAG content at the end of the experiment.

Dose Response of Fusion Proteins in Human Cartilage in the Presence of Human IL-1β

Preliminary dose response experiments were performed to test the effects of human IL-1β (PeproTech, Rocky Hill, NJ) on human ankle cartilage. Ankle cartilage explants from two different donors (equilibrated in culture medium post-harvest) were cultured in serum-free low glucose medium (same composition as equilibration medium) and treated with continuous IL-1β doses ranging from 10 pg/ml to 1 ng/ml for 8 days. The experiments also included groups of explants that were treated with 300 ng/ml free IGF-1 at each dose level of IL-1β. Based on the results of these experiments, 100 pg/ml IL-1β was chosen as the dose used for the fusion protein dose response experiments. In these experiments, ankle and knee cartilage explants (equilibrated in culture medium post-harvest) were treated continuously with IL-1β and received single doses of fusion proteins (ranging from 39.2 nM to 2 μM) at the start of the experiments. Media changes with IL-1β but without fusion proteins were performed once every 2 to 3 days. An untreated control group, a control with continuous IL-1β alone, and a control with IL-1β combined with continuous free IGF-1 (300 ng/ml or 39.2 nM) were included. Experiments were terminated at 7-day and 10-day timepoints, and the sGAG biosynthesis rate, metabolic rate, sGAG loss to culture medium and sGAG content of the explants were measured.

Cartilage Biosynthesis, Metabolic Rate and sGAG Loss

The metabolic rate of cartilage explants was measured using the Alamar Blue assay (ThermoFisher). Cartilage explants were incubated for 3 hours in a 1× solution of Alamar Blue dissolved in culture medium. At the end of the incubation period, the absorbance of the medium at 570 nm and 600 nm was measured using a microplate reader (Synergy H1 Hybrid Multi-Mode Microplate Reader, BioTek). These readings were used to calculate the percentage reduction of Alamar Blue, which is directly proportional to the explant metabolic rate. These values were first normalized by individual explant weights. Following this, the weight-normalized readings for the treatment groups were normalized by the weight-normalized mean value for the untreated controls. To measure the chondrocyte biosynthesis rate of sulfated glycosaminoglycans (sGAGs), cartilage explants were cultured in the presence of 10 μCi/mL 35S-sulfate radiolabel during the final two days of each experiment. Following this, the explants were washed with PBS with non-radioactive sulfate to wash out excess radiolabel, weighed and digested with proteinase K. A liquid scintillation counter (PerkinElmer) was used to measure the amount of radiolabel incorporated within the extracellular matrix of the tissues. Radiolabel incorporation data were normalized by the duration of exposure to radiolabel and by the wet weight of the explants (Li et al., Osteoarthritis and Cartilage 23(2):266-274 (2015)). To calculate the cumulative loss of GAGs from the explants, the amount of sGAG lost to the medium and that left behind in the explants at the end of the experiment were measured using the dimethylene blue (DMMB) dye binding assay (Farndale et al., Biochim Biophys Acta. 883(2):173-177 (1986)).

Statistical Analysis

Statistical analysis was carried out using MATLAB and JMP Pro 14 software packages. All quantitative data are plotted as Mean±95% Confidence Interval. For experiments with a single human donor, a one-way ANOVA followed by the post-hoc Tukey's HSD test was performed. Data from experiments with multiple human donors were analyzed using the linear mixed effects model with human donor as a random factor and this was followed by the post-hoc Tukey's HSD test. In both cases, p-values less than 0.05 were considered statistically significant.

Results

Characterization of Purified Fusion Proteins

Figure 8C:
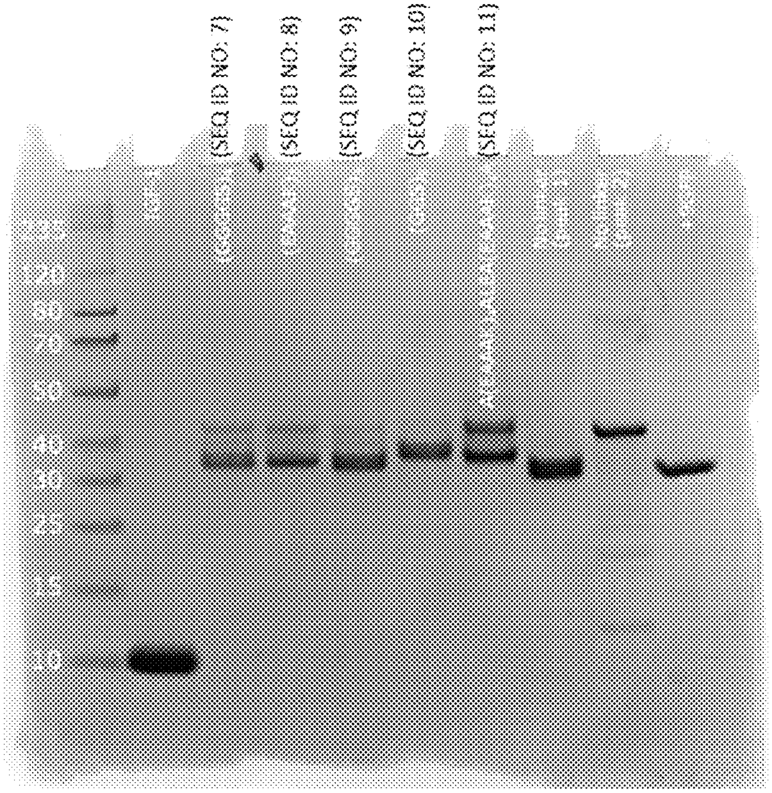
Figure 16A:
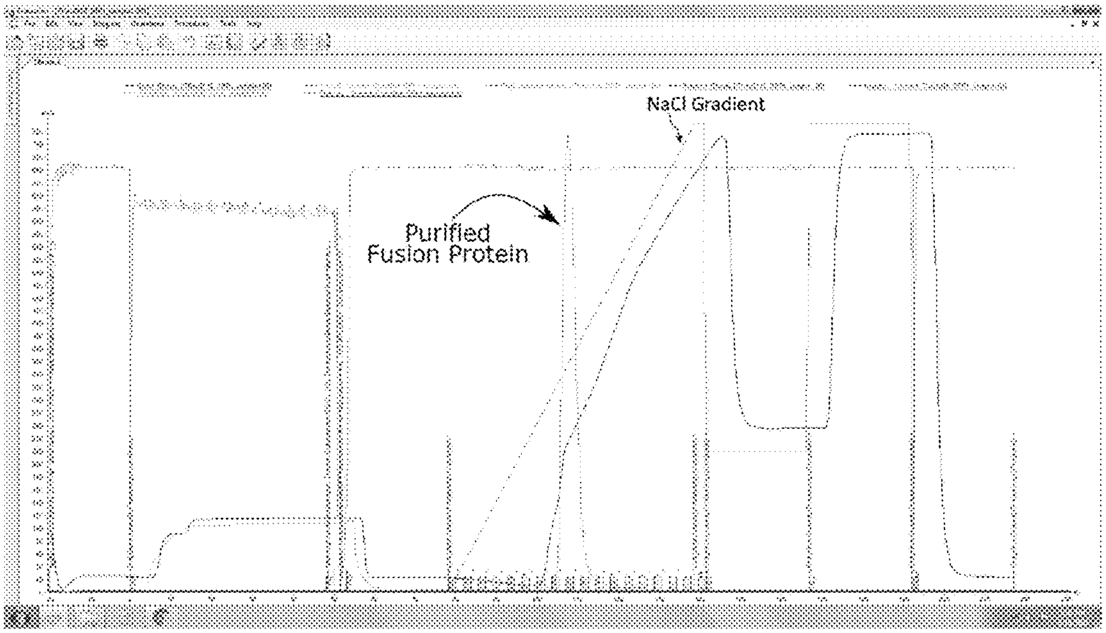
FIGS. 16A-16B show representative FPLC cation exchange chromatography elution profiles. Elution was performed with a linear NaCl gradient (0 to 1 M). Purified Fusion Protein UV readings were taken at 280 nm.
Figure 16B:
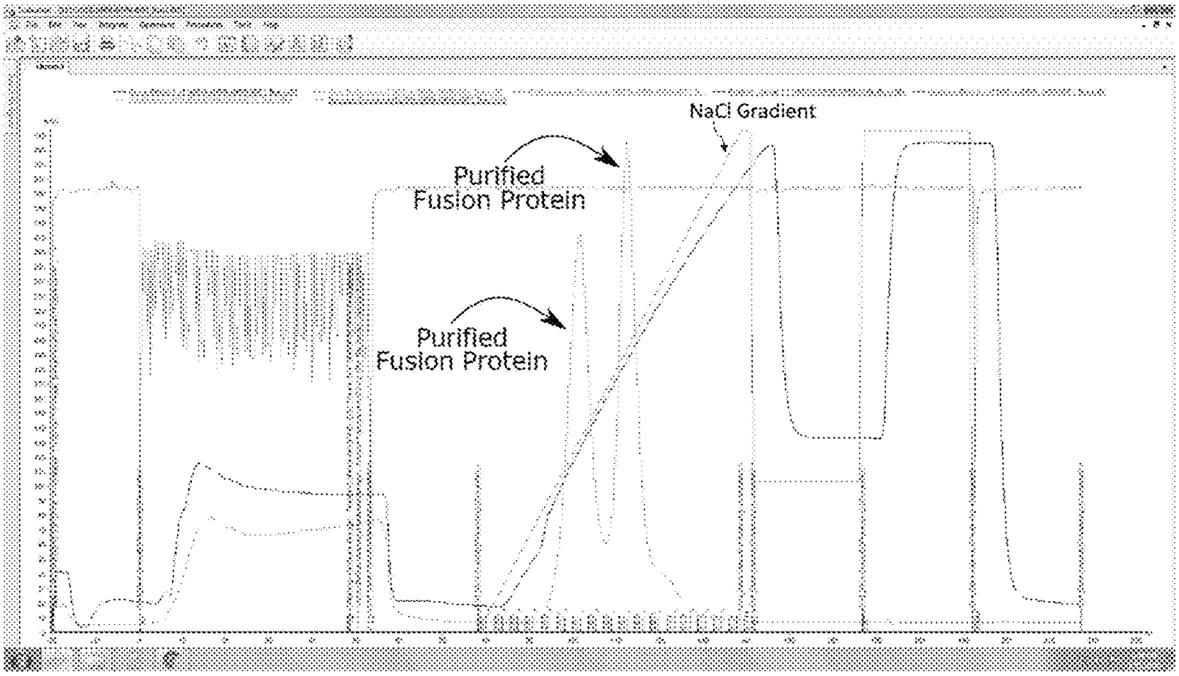

During the FPLC step of protein purification, the fusion proteins with linkers were eluted as a single sharp peak which was collected in several fractions (a representative FPLC trace is shown in FIG. 16A). Fractions containing pure protein (as characterized by SDS PAGE) were pooled. The fusion protein with no linker was eluted as two peaks (FPLC trace is shown in FIG. 16B). Once again, fractions containing pure protein were pooled, but the fractions from each peak were pooled separately. After these pooled samples were concentrated and sterile filtered, the purity of the protein was confirmed through SDS PAGE (FIG. 8C).

Figure 17:
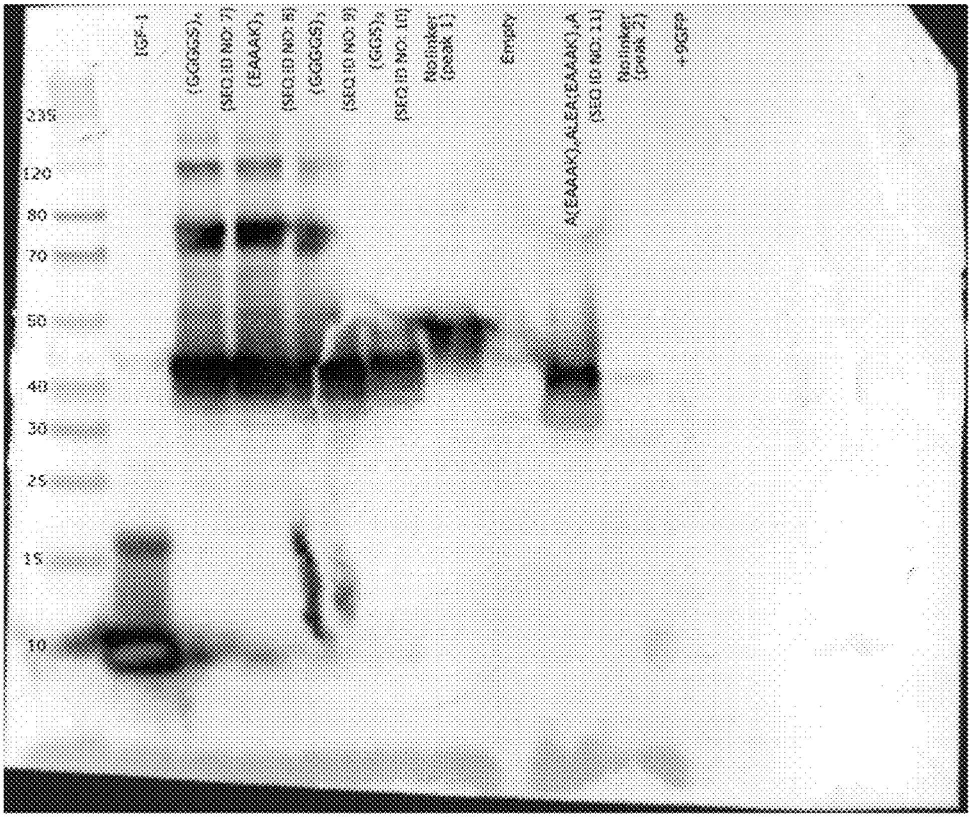
FIG. 17 shows the Western blot analysis of purified and concentrated +9GFP-IGF-1 fusion proteins. Recombinant human IGF-1 (1st lane) and +9GFP (free carrier; last lane) were included as controls.

All the fusion proteins were fluorescent, indicating that the +9 GFP domain was present and had folded properly. To confirm that they also had the IGF-1 domain, a western blot with polyclonal anti-IGF-1 antibody was performed. A control with free IGF-1 and a control with +9 GFP (free carrier control) were also included in the blot. Highly intense bands were found in the lanes with the free IGF-1, the five fusion proteins with linkers, and one of the two elution peaks of the fusion protein without a linker (FIG. 17). The lane with the other peak for the fusion protein without a linker had a faint band and no band was found in the lane with +9 GFP. This confirmed that all the fusion proteins had the IGF-1 domain.

The lanes for three of the fusion proteins had bands with molecular weights that were approximately twice and three times the theoretical molecular weights of the proteins, indicating that these correspond to dimers and trimers. The IGF-1 lane also had a second band which most likely corresponds to a dimer.

Uptake and Penetration of Fusion Proteins in Human Cartilage

1 μM solutions of +9 GFP, two fusion proteins with flexible linkers, (+9GFP)-$(GGGGS)_4$-(IGF-1) (SEQ ID NO: 7), and (+9GFP)-$(GGGGS)_3$-(IGF-1) (SEQ ID NO: 9) and one fusion protein with a rigid linker, (+9GFP)-$(EAAAK)_3$-(IGF-1) (SEQ ID NO: 8) were prepared in PBS+1% BSA. The uptake ratios of these four proteins were quantified in human ankle cartilage after 36-hour and 108-hour incubations (37° C., 5% $CO_2$). At 36 hours, the concentrations of all three fusion proteins was approximately 10 to 20 times higher in cartilage compared to the final bath (FIG. 9A and Table 5). Even though this demonstrated enhanced uptake of the fusion proteins into cartilage, these values were significantly lower than the uptake ratio of +9 GFP.

Similar trends were observed at the 108-hour time point as well (FIG. 9B and Table 5). Additionally, the uptake ratios of each fusion protein were higher after a 108-hour incubation compared to its 36-hour uptake ratio. However, the increase observed in +9 GFP uptake ratio from 36 hours to 108 hours was much higher than the increase observed for any of the fusion proteins.

TABLE 5

Uptake ratios of fusion proteins in human cartilage (Mean ± Standard Deviation; N = 5 explants/condition)

| | PBS + 1% BSA | | | |
|---|---|---|---|---|
| | 36 hr | | 108 hr | |
| Protein | Mean | Std. Dev | Mean | Std. Dev |
| (+9GFP)-$(GGGGS)_4$-(IGF-1) (SEQ ID NO: 7) | 12.7 | 1.5 | 18.3 | 6.7 |
| ((+9GFP)-$(GGGGS)_3$-(IGF-1) (SEQ ID NO: 9) | 19.8 | 1.6 | 37.8 | 3.6 |
| (+9GFP)-$(GGGGS)_3$-(IGF-1) (SEQ ID NO: 9) | 13.1 | 1.7 | 24.2 | 6.4 |
| +9GFP | 42.3 | 10.8 | 113.9 | 34.5 |

To visualize the extent of penetration of the fusion proteins in cartilage, human knee and ankle cartilage explants were treated with a single dose (1 μM) of the proteins and were cultured in serum-free, low glucose medium for 7 to 8 days. Media changes were performed every 2 to 3 days. Subsets of explants were terminated at different time points, washed with PBS, sliced longitudinally and imaged using confocal microscopy. The confocal microscopy images as well as the intensity profiles are shown in FIG. 10A. All three fusion proteins penetrated through the full thickness of cartilage within the first 1 to 2 days.

Single Doses of Two Fusion Proteins Sustain Elevated sGAG Biosynthesis in Human Cartilage for at Least 1 Week In previous studies, treatment with IGF-1 increased the sGAG biosynthesis rate in cartilage and maintaining this increase requires continuous dosage. 39.2 nM doses of (+9GFP)-$(GGGGS)_4$-(IGF-1) (SEQ ID NO: 7) and (+9GFP)-$(EAAAK)_3$-(IGF-1) (SEQ ID NO: 8) (equivalent to 300 ng/ml free IGF-1) did not increase the biosynthesis rate of explants compared to the untreated control (FIGS. 19A-19B). However, 500 nM, 1 μM and 2 μM doses of these fusion proteins ((+9GFP)-$(GGGGS)_4$-(IGF-1) (SEQ ID NO: 7) and (+9GFP)-$(EAAAK)_3$-(IGF-1) (SEQ ID NO: 8)) led to a significant increase in the sGAG biosynthesis rate of both ankle and knee cartilage as measured between Day 0 and Day 3 of the culture. This increase was comparable to the biosynthesis increase caused by treatment with free IGF-1 during the same time period.

For the fusion protein treatment groups, the fusion proteins were not replenished during media changes. Despite this, the elevated biosynthesis rates in the (+9GFP)-$(GGGGS)_4$-(IGF-1) (SEQ ID NO: 7) and (+9GFP)-$(EAAAK)_3$-(IGF-1) (SEQ ID NO: 8) groups were sustained up to Day 7 of the culture. However, a single dose of these proteins could not maintain the elevated biosynthesis rate up to Day 15 of the culture. The increase in biosynthesis caused by continuous 39.2 nM (300 ng/ml) doses of free IGF-1 at Day 3, Day 7 and Day 15 are shown for comparison (FIG. 12).

Figure 21:
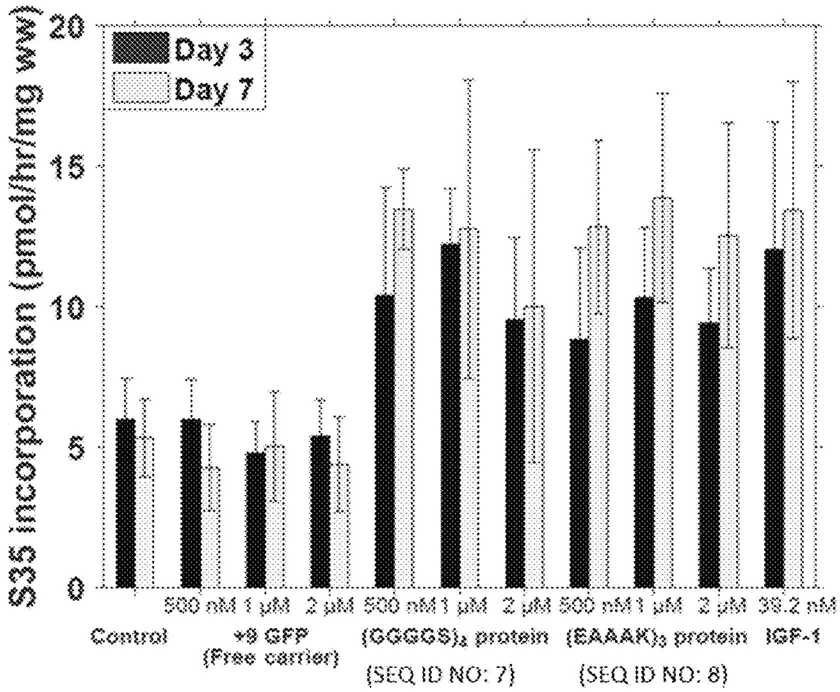
FIG. 21 shows the normalized sulfate incorporation rate of human ankle cartilage explants (66-year-old male donor; Collins grade 0) in a dose response experiment with +9GFP-IGF-1 fusion protein variants. Groups of explants were treated with 500 nM, 1 μM and 2 μM doses of fusion protein variants with the $(GGGGS)_4$ (SEQ ID NO: 27) and $(EAAAK)_3$ (SEQ ID NO: 30) linkers. Groups of explants were also treated with equivalent doses of +9GFP (the drug delivery carrier). An untreated control group and a group with continuous dosage of free IGF-1 were also included in the experiment. All the fusion protein groups had sulfate incorporation rates comparable to the IGF-1 group, while the +9GFP groups were not significantly different from the untreated control. Bars represent mean values±standard deviations; N=7 to 9 explants/condition.
Figure 22:
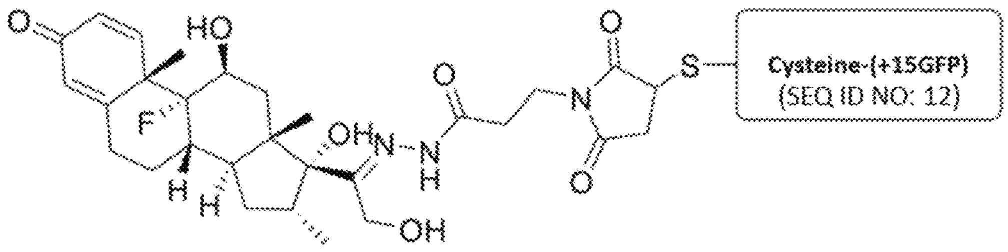
FIG. 22 shows the chemical structure of a dexamethasone-(Cysteine-(+15GFP)) conjugate with a pH-sensitive hydrazone linker.
Figure 23:
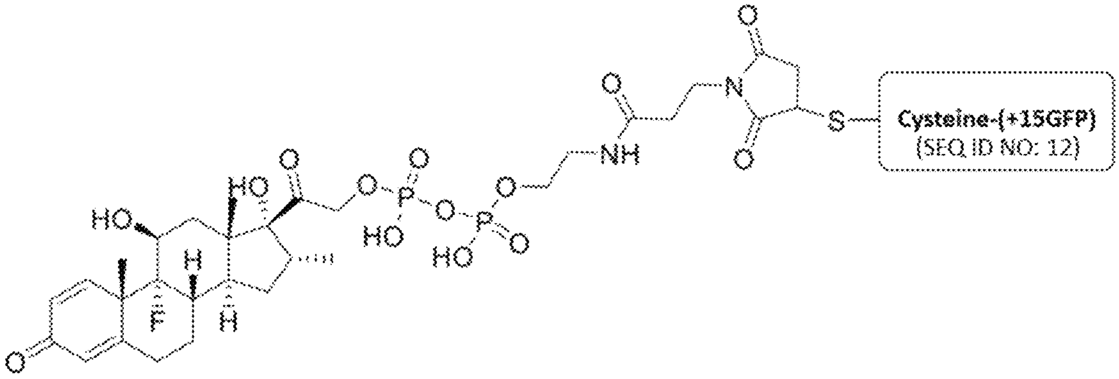
FIG. 23 shows the chemical structure of a dexamethasone-(Cysteine-(+15GFP)) conjugate with a lysosomal enzyme-sensitive pyrophosphate diester linker.
Figure 24:
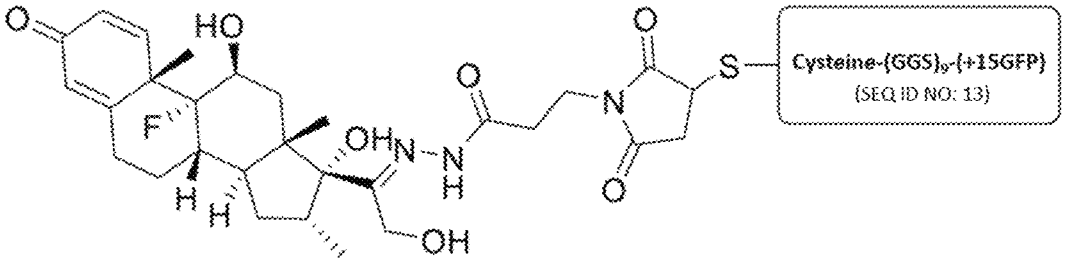
FIG. 24 shows the chemical structure of a dexamethasone-(Cysteine-$(GGS)_9$-(+15GFP)) conjugate with a pH-sensitive hydrazone linker.
Figure 25:
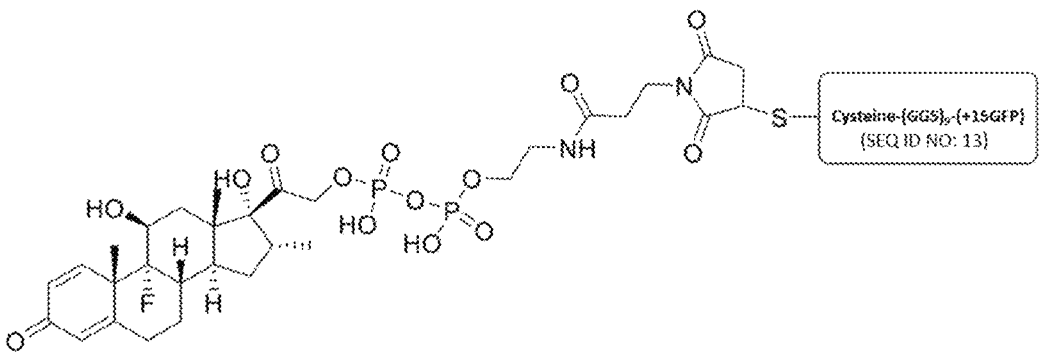
FIG. 25 shows the chemical structure of a dexamethasone-(Cysteine-$(GGS)_9$-(+15GFP)) conjugate with a lysosomal enzyme-sensitive pyrophosphate diester linker.

In one of the experiments, a free carrier control (500 nM, 1 μM and 2 μM of +9 GFP) was included to confirm whether or not the drug delivery carrier had an effect on the sGAG biosynthesis rate. There was no statistically significant difference in the sGAG biosynthesis rate between the explants treated with the different doses of +9 GFP and the untreated control explants (FIG. 21).

TABLE 6

Post hoc comparisons (using Tukey's HSD) for the experiment in FIG. 12A. The tables show p-values for the 3-day long experiment (Table A), 7-day long experiment (Table B), and 15-day long experiment (Table C). Significant p-values (less than 0.05) are shown in bold font.

| | | (+9GFP)-$(GGGGS)_4$-(IGF-1) (SEQ ID NO: 7) | | | (+9GFP)-$(EAAAK)_3$-(IGF-1) (SEQ ID NO: 8) | | | |
|---|---|---|---|---|---|---|---|---|
| | | 500 nM | 1 μM | 2 μM | 500 nM | 1 μM | 2 μM | IGF-1 |
| (A) 3-day experiment; ankle cartilage | | | | | | | | |
| Untreated control | | 0.0677 | **0.0027** | 0.3249 | 0.6014 | 0.1182 | 0.2852 | **0.0026** |
| (+9GFP)-$(GGGGS)_4$- | 500 nM | | 0.9139 | 0.999 | 0.9665 | 1 | 0.9968 | 0.938 |
| (IGF-1) (SEQ ID NO: 7) | 1 μM | | | 0.6634 | 0.3787 | 0.9216 | 0.5418 | 1 |
| | 2 μM | | | | 0.9999 | 0.9996 | 1 | 0.7039 |
| (+9GFP)-$(EAAAK)_3$- | 500 nM | | | | | 0.982 | 0.9999 | 0.4099 |
| (IGF-1) (SEQ ID NO: 8) | 1 μM | | | | | | 0.9988 | 0.9436 |
| | 2 μM | | | | | | | 0.5809 |
| (B) 7-day experiment; ankle cartilage | | | | | | | | |
| Untreated control | | **$<10^{-4}$** | **$<10^{-4}$** | **$<10^{-4}$** | **$<10^{-4}$** | **$<10^{-4}$** | **$<10^{-4}$** | **$<10^{-4}$** |
| (+9GFP)-$(GGGGS)_4$- | 500 nM | | 0.522 | 1 | 0.8818 | 1 | 0.7609 | **$<10^{-4}$** |
| (IGF-1) (SEQ ID NO: 7) | 1 μM | | | 0.5095 | **0.0252*** | 0.7328 | 1 | **$<10^{-4}$** |
| | 2 μM | | | | 0.9453 | 0.9999 | 0.7194 | **$<10^{-4}$** |
| (+9GFP)-$(EAAAK)_3$- | 500 nM | | | | | 0.7368 | 0.0911 | **$<10^{-4}$** |
| (IGF-1) (SEQ ID NO: 8) | 1 μM | | | | | | 0.9008 | **$<10^{-4}$** |
| | 2 μM | | | | | | | **$<10^{-4}$** |
| (C) 15-day experiment; ankle cartilage | | | | | | | | |
| Untreated control | | 0.879 | 0.8587 | 0.5099 | 0.8299 | 0.9845 | 1 | **$<10^{-4}$** |
| (+9GFP)-$(GGGGS)_4$- | 500 nM | | 1 | 0.9929 | 1 | 0.9999 | 0.9861 | **$<10^{-4}$** |
| (IGF-1) (SEQ ID NO: 7) | 1 μM | | | 0.9956 | 1 | 0.9997 | 0.981 | **$<10^{-4}$** |
| | 2 μM | | | | 0.9977 | 0.9421 | 0.7712 | **$<10^{-4}$** |
| (+9GFP)-$(EAAAK)_3$- | 500 nM | | | | | 0.9994 | 0.9727 | **$<10^{-4}$** |
| (IGF-1) (SEQ ID NO: 8) | 1 μM | | | | | | 0.9995 | **$<10^{-4}$** |
| | 2 μM | | | | | | | **$<10^{-4}$** |

TABLE 7

Post hoc comparisons (using Tukey's HSD) for the experiment in FIG. 12B. The tables show p-values for the 3-day long experiment (Table A), 7-day long experiment (Table B), and 15-day long experiment (Table C). Significant p-values (less than 0.05) are shown in bold font.

| | | (+9GFP)-$(GGGGS)_4$-(IGF-1) (SEQ ID NO: 7) | | | (+9GFP)-$(EAAAK)_3$-(IGF-1) (SEQ ID NO: 8) | | | |
|---|---|---|---|---|---|---|---|---|
| | | 500 nM | 1 μM | 2 μM | 500 nM | 1 μM | 2 μM | IGF-1 |
| (A) 3-day experiment; knee cartilage | | | | | | | | |
| Untreated control | | **0.0002** | 0.1715 | **0.0014** | **0.0074** | **0.0117** | **0.0054** | **$<10^{-4}$** |
| (+9GFP)-$(GGGGS)_4$- | 500 nM | | 0.9137 | 0.9984 | 0.9428 | 1 | 0.9651 | 0.4372 |
| (IGF-1) (SEQ ID NO: 7) | 1 μM | | | 0.9943 | 1 | 0.9797 | 0.9999 | 0.0968 |
| | 2 μM | | | | 0.9995 | 1 | 0.9999 | 0.1409 |
| (+9GFP)-$(EAAAK)_3$- | 500 nM | | | | | 0.9969 | 1 | **0.039** |
| (IGF-1) (SEQ ID NO: 8) | 1 μM | | | | | | 0.9986 | 0.6053 |
| | 2 μM | | | | | | | 0.0511 |
| (B) 7-day experiment; knee cartilage | | | | | | | | |
| Untreated control | | **0.0073** | 0.4272 | **$<10^{-4}$** | **0.0084** | **0.0011** | **0.0006** | **$<10^{-4}$** |
| (+9GFP)-$(GGGGS)_4$- | 500 nM | | 0.9338 | 0.8296 | 1 | 0.9779 | 0.9976 | **$<10^{-4}$** |
| (IGF-1) (SEQ ID NO: 7) | 1 μM | | | 0.2151 | 0.944 | 0.479 | 0.6326 | **$<10^{-4}$** |
| | 2 μM | | | | 0.8076 | 1 | 0.9936 | **$<10^{-4}$** |
| (+9GFP)-$(EAAAK)_3$- | 500 nM | | | | | 0.9726 | 0.9965 | **$<10^{-4}$** |
| (IGF-1) (SEQ ID NO: 8) | 1 μM | | | | | | 0.9999 | **$<10^{-4}$** |
| | 2 μM | | | | | | | **$<10^{-4}$** |
| (C) 15-day experiment; knee cartilage | | | | | | | | |
| Untreated control | | 1 | 1 | 1 | 0.5483 | 0.6187 | 0.5488 | **$<10^{-4}$** |
| (+9GFP)-$(GGGGS)_4$- | 500 nM | | 1 | 1 | 0.4718 | 0.5412 | 0.4723 | **$<10^{-4}$** |
| (IGF-1) (SEQ ID NO: 7) | 1 μM | | | 1 | 0.5597 | 0.6301 | 0.5602 | **$<10^{-4}$** |
| | 2 μM | | | | 0.5232 | 0.5936 | 0.5237 | **$<10^{-4}$** |
| (+9GFP)-$(EAAAK)_3$- | 500 nM | | | | | 1 | 1 | **$<10^{-4}$** |
| (IGF-1) (SEQ ID NO: 8) | 1 μM | | | | | | 1 | **$<10^{-4}$** |
| | 2 μM | | | | | | | **$<10^{-4}$** |

Effect of Single Doses of Fusion Proteins on the Final Explant sGAG Content and Cumulative sGAG Loss to Culture Medium Cumulative sGAG lost to the culture medium and the final explant sGAG content were measured for the explants used in FIGS. 12A-12B. The results for these are shown in FIGS. 13A-13D. Treatment with a single dose of fusion proteins did not affect the final explant sGAG content (normalized to explant wet weight) at any of the three time points. The cumulative percent sGAG loss to the culture medium was also comparable to the untreated control group at the 3-day and 7-day time points. However, some of the fusion protein treatment groups had a modest increase in the cumulative GAG loss percent compared to the untreated control by day 15 (statistical comparisons shown in Table 8). The explants treated with free IGF-1 did not have any change in the final explant GAG content or the cumulative GAG loss percent compared to the untreated control at any of the three time points used in these experiments.

sGAG biosynthesis rate measured during the last two days of the experiment decreased with increasing doses of IL-1β. Adding IGF-1 helped in rescuing this biosynthesis loss, but this effect also got weaker with increasing IL-1 doses.

Treatment with IGF-1 in the presence of 10 pg/ml IL-1β resulted in a biosynthesis rate that surpassed the untreated control biosynthesis in both donors. On the other hand, the explants receiving IGF-1 and 500 pg/ml or 1 ng/ml IL-1β in the 58-year-old male donor had significantly lower biosynthesis compared to the untreated control. In both donors, a 100 pg/ml dose of IL-1β resulted in a significant loss of biosynthesis and adding IGF-1 brought back the biosynthesis rate to a level that was not statistically significantly different from the untreated control. Based on these results, 100 pg/ml human IL-1β was used for all other cytokine challenge experiments.

TABLE 8

Figure 13A:
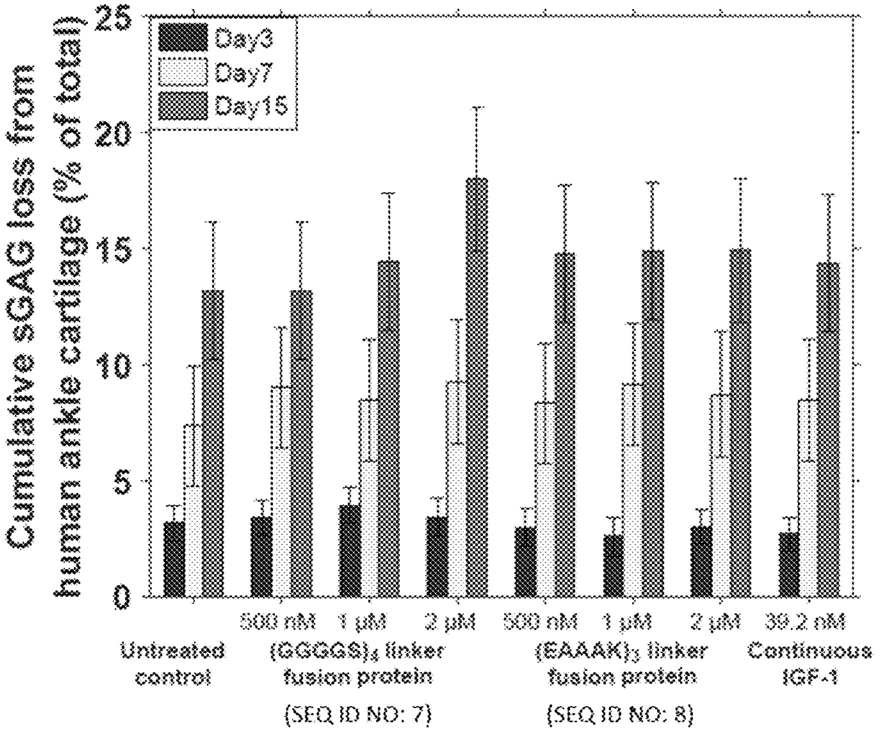
FIGS. 13A-13D show data for the cumulative percent sGAG loss and final explant sGAG content for ankle and knee cartilage dose response experiments.
Figure 13B:
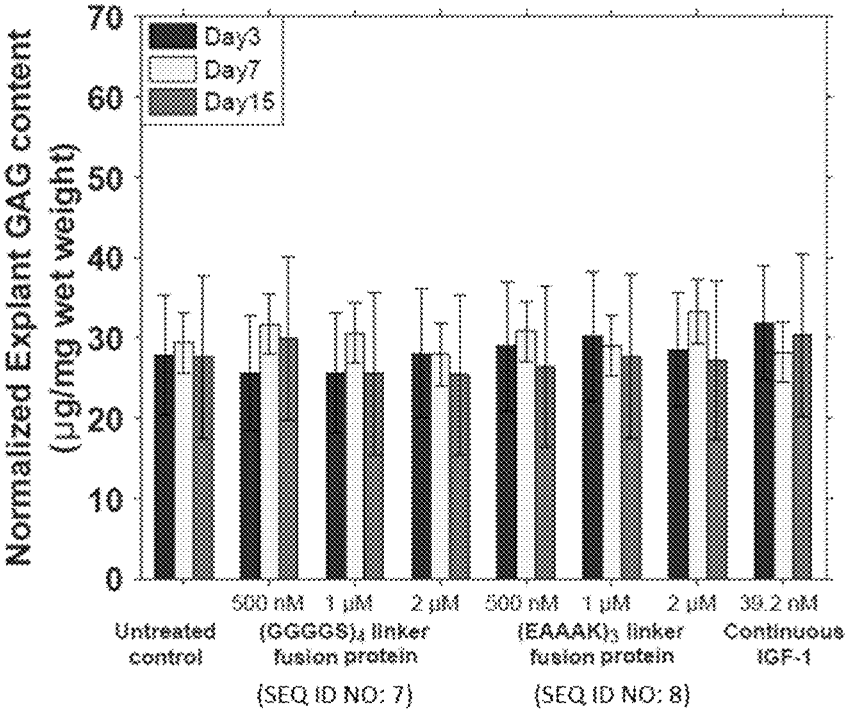
Figure 13C:
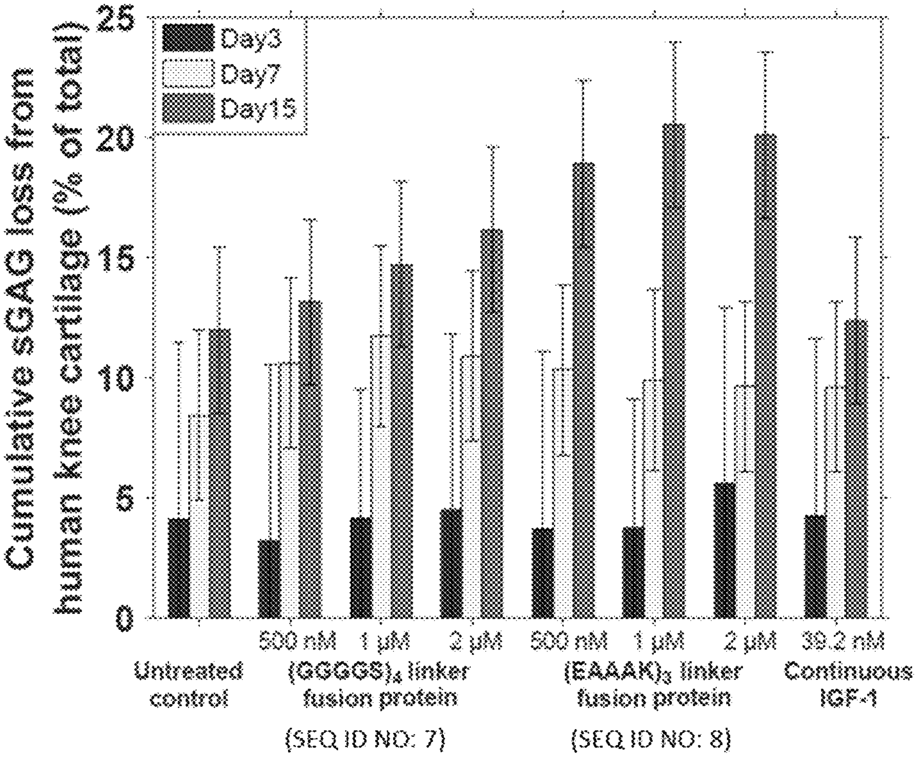
Figure 13D:
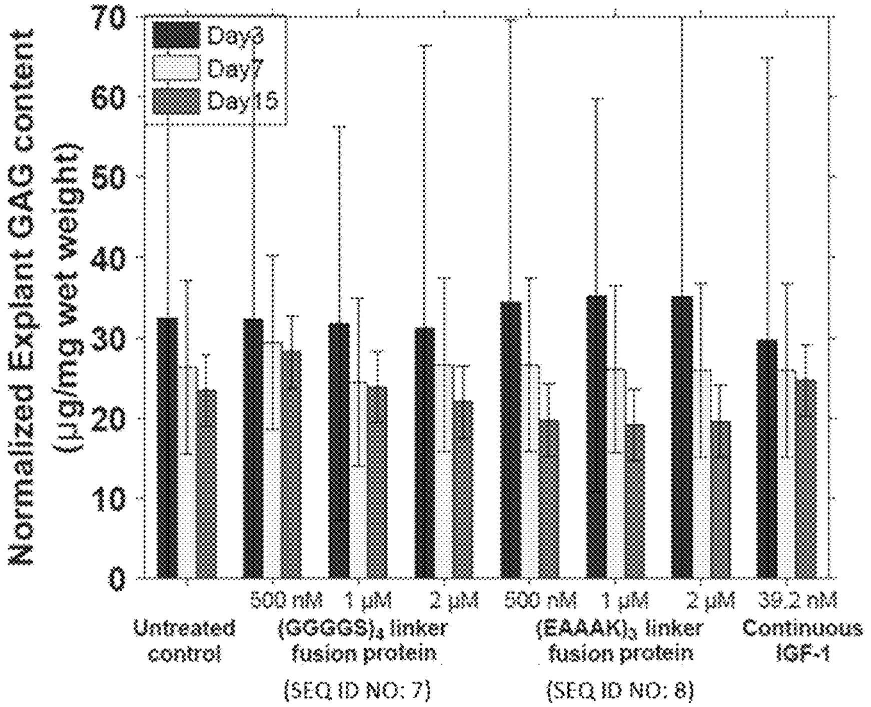

Post hoc comparisons (using Tukey's HSD) for the data in FIGS. 13A and C. p-values for the 15-day cumulative sGAG loss data in FIG. 13A are shown in (Table A). p-values for 15-day cumulative sGAG loss data in FIG. 13C are shown in (Table B). Significant p-values (less than 0.05) are shown in bold font.

| | | (+9GFP)-(GGGGS)$_4$-(IGF-1) (SEQ ID NO: 7) | | | (+9GFP)-(EAAAK)$_3$-(IGF-1) (SEQ ID NO: 8) | | | |
|---|---|---|---|---|---|---|---|---|
| | | 500 nM | 1 μM | 2 μM | 500 nM | 1 μM | 2 μM | IGF-1 |
| (A) 15-day experiment; ankle cartilage | | | | | | | | |
| Untreated control | | 1 | 0.9725 | **0.0168** | 0.9115 | 0.8716 | 0.9185 | 0.9777 |
| (+9GFP)-(GGGGS)$_4$- | 500 nM | | 0.972 | **0.0167** | 0.9104 | 0.8702 | 0.9175 | 0.9772 |
| (IGF-1) (SEQ ID NO: 7) | 1 μM | | | | 1 | 1 | 1 | 1 |
| | 2 μM | | | | 0.3019 | 0.3362 | 0.4625 | 0.1636 |
| (+9GFP)-(EAAAK)$_3$- | 500 nM | | | | | 1 | 1 | 1 |
| (IGF-1) (SEQ ID NO: 8) | 1 μM | | | | | | 1 | 0.9999 |
| | 2 μM | | | | | | | 0.9999 |
| (B) 15-day experiment; knee cartilage | | | | | | | | |
| Untreated control | | 0.9997 | 0.9457 | 0.6701 | 0.1051 | **0.0206** | **0.0329** | 1 |
| (+9GFP)-(GGGGS)$_4$- | 500 nM | | 0.9979 | 0.9144 | 0.2742 | 0.0692 | 0.1044 | 1 |
| (IGF-1) (SEQ ID NO: 7) | 1 μM | | | 0.9988 | 0.6597 | 0.2625 | 0.355 | 0.9765 |
| | 2 μM | | | | 0.9415 | 0.6115 | 0.7254 | 0.7686 |
| (+9GFP)-(EAAAK)$_3$- | 500 nM | | | | | 0.9973 | 0.9997 | 0.1489 |
| (IGF-1) (SEQ ID NO: 8) | 1 μM | | | | | | 1 | **0.0315** |
| | 2 μM | | | | | | | **0.0495** |

Dose Response of Human IL-1β Individually and Combined with Free Human IGF-1

In preliminary experiments, fusion proteins were tested in a cytokine injury model using 10 ng/ml mouse IL-1β. In these experiments, continuous treatment with 39.2 nM doses (equivalent to 300 ng/ml) of recombinant IGF-1 rescued the biosynthesis loss caused by IL-1, but equivalent single doses (39.2 nM) of the fusion proteins did not (FIG. 20). Upon switching to human IL-1β (instead of mouse IL-1β), even the continuous free IGF-1 treatment could not rescue biosynthesis loss even though the IL-1 dose was reduced from 10 ng/ml to 1 ng/ml. Before testing the fusion proteins further in this injury model, dose response experiments were performed to determine optimal human IL-1β dose levels such that the injury caused could be rescued by IGF-1. Ankle cartilage explants from two donors were treated continuously with human IL-1β doses ranging from 10 pg/ml to 1 ng/ml. At each dose level of IL-1β, half the explants were also treated with continuous 300 ng/ml doses of IGF-1. Each experiment included an untreated control group as well. The Single Doses of the Two Bioactive Fusion Proteins Rescue IL-1β Induced Biosynthesis Loss in Human Ankle Cartilage Human ankle cartilage explants from six different donors were treated continuously with 100 pg/ml IL-1β, with media changes performed every 2 to 3 days. The treatment groups received single doses (500 nM, 1 μM or 2 μM) of the two fusion proteins that were found to be bioactive in the experiments in FIGS. 12A-12B. An untreated control, a control with 100 pg/ml IL-1β, and a group with 100 pg/ml IL-1β+300 ng/ml IGF-1 were included in each experiment. Explants from four donors were terminated on day 7 of the experiment, while the experiments from the other two donors were terminated on day 10. The results for the sGAG biosynthesis rate of the explants are shown in FIG. 15A. The data for the cumulative sGAG loss and the explant sGAG content at the end of the experiment are shown in FIG. 15B.

In both the 7-day and 10-day experiments, the biosynthesis rate of the IL-1β group was significantly lower than that of the untreated control. Continuous treatment with free IGF-1 led to a complete rescue of biosynthesis loss, and the free IGF-1 groups in both experiments were significantly higher than the IL-1β group and not significantly different compared to the untreated control.

In the 7-day experiment (FIG. 15A), a single 2 μM dose of (+9GFP)-$(GGGGS)_4$-(IGF-1) (SEQ ID NO: 7) was able to completely rescue the loss of biosynthesis caused by IL-1β. It was significantly higher than the IL-10 group and not significantly different compared to the untreated control. In addition to this, a single 1 μM dose of (+9GFP)-$(EAAAK)_3$-(IGF-1) (SEQ ID NO: 8) achieved a partial rescue of biosynthesis loss. This group was significantly higher than the IL-1β group but also significantly lower than the untreated control.

In the 10-day experiment (FIG. 15B), single doses of (+9GFP)-$(GGGGS)_4$-(IGF-1) (SEQ ID NO: 7) (1 μM and 2 μM) and (+9GFP)-$(EAAAK)_3$-(IGF-1) (SEQ ID NO: 8) (2 μM) partially rescued the biosynthesis loss caused by IL-1β. All three groups were significantly higher than the IL-1β group but also significantly lower than the untreated control.

In both the 7-day and 10-day experiments, there were no differences in the final sGAG content of the explants (FIG. 15D). However, at the 7-day time point, all the fusion protein groups and the free IGF-1 group had higher cumulative sGAG loss to the medium compared to the untreated control (FIG. 15C). (The IL-1 group GAG loss was border line with a p-value of 0.054). At the 10-day time point, the IL-1β group and the groups receiving 500 nM (+9GFP)-$(GGGGS)_4$-(IGF-1) (SEQ ID NO: 7) and 2 μM (+9GFP)-$(EAAAK)_3$-(IGF-1) (SEQ ID NO: 8) had higher cumulative sGAG loss compared to the untreated control.

TABLE 9

Post hoc comparisons (using Tukey's HSD) for the data in FIGS. 15A-15B. p-values for the sGAG biosynthesis rate data in FIG. 15A are shown in (Table A), and p-values for the data in FIG. 15B are shown in (Table B). Significant p-values (less than 0.05) are shown in bold font.

| | | | (+9GFP)-$(GGGGS)_4$-(IGF-1) (SEQ ID NO: 7) | | | (+9GFP)-$(EAAAK)_3$-(IGF-1) (SEQ ID NO: 8) | | | |
|---|---|---|---|---|---|---|---|---|---|
| | | IL-1β | 500 nM | 1 μM | 2 μM | 500 nM | 1 μM | 2 μM | IGF-1 |
| (A) 7-day experiment; ankle cartilage | | | | | | | | | |
| Untreated control | | **<$10^{-4}$** | **<$10^{-4}$** | **<$10^{-4}$** | 0.079 | **<$10^{-4}$** | **0.0004** | **0.0002** | 0.2262 |
| IL-1β | | | 0.9002 | 0.0921 | **<$10^{-4}$** | 0.7649 | **0.0048** | **0.045** | **<$10^{-4}$** |
| (+9GFP)- | 500 nM | | | 0.8471 | **0.0161** | 1 | 0.2592 | 0.6461 | **<$10^{-4}$** |
| $(GGGGS)_4$- | 1 μM | | | | 0.503 | 0.9516 | 0.9908 | 1 | **<$10^{-4}$** |
| (IGF-1) (SEQ ID NO: 7) | 2 μM | | | | | **0.0403** | 0.9607 | 0.8246 | **<$10^{-4}$** |
| (+9GFP)- | 500 nM | | | | | | 0.4403 | 0.8187 | **<$10^{-4}$** |
| $(EAAAK)_3$- | 1 μM | | | | | | | 1 | **<$10^{-4}$** |
| (IGF-1) (SEQ ID NO: 8) | 2 μM | | | | | | | | **<$10^{-4}$** |
| (B) 10-day experiment; ankle cartilage | | | | | | | | | |
| Untreated control | | **<$10^{-4}$** | **<$10^{-4}$** | **0.0014** | **0.0026** | **<$10^{-4}$** | **0.0002** | **0.0038** | 0.9999 |
| IL-1β | | | 0.9778 | **0.0199** | **0.0115** | 0.8855 | 0.081 | **0.008** | **<$10^{-4}$** |
| (+9GFP)- | 500 nM | | | 0.3021 | 0.2175 | 1 | 0.6168 | 0.1727 | **<$10^{-4}$** |
| $(GGGGS)_4$- | 1 μM | | | | 1 | 0.5678 | 0.9999 | 1 | **0.0003** |
| (IGF-1) (SEQ ID NO: 7) | 2 μM | | | | | 0.4545 | 0.9993 | 1 | **0.0007** |
| (+9GFP)- | 500 nM | | | | | | 0.8575 | 0.3858 | **<$10^{-4}$** |
| $(EAAAK)_3$- | 1 μM | | | | | | | 0.9978 | **<$10^{-4}$** |
| (IGF-1)protein (SEQ ID NO: 8) | 2 μM | | | | | | | | **0.001** |

TABLE 10

Post hoc comparisons (using Tukey's HSD) for the data in FIG. 15C. p-values for the cumulative sGAG biosynthesis loss data in the 7-day experiment are shown in (Table A). p-values for the cumulative sGAG biosynthesis loss data in the 10-day experiment are shown in (Table B). Significant p-values (less than 0.05) are shown in bold font.

| | | | (+9GFP)-$(GGGGS)_4$-(IGF-1) (SEQ ID NO: 7) | | | (+9GFP)-$(EAAAK)_3$-(IGF-1) (SEQ ID NO: 8) | | | |
|---|---|---|---|---|---|---|---|---|---|
| | | IL-1β | 500 nM | 1 μM | 2 μM | 500 nM | 1 μM | 2 μM | IGF-1 |
| (A) 7-day experiment; ankle cartilage | | | | | | | | | |
| Untreated control | | 0.054 | **<$10^{-4}$** | **<$10^{-4}$** | **0.0063** | **0.0002** | **0.0042** | **0.0001** | **0.0013** |
| IL-1β | | | 0.155 | 0.4957 | 0.9958 | 0.8436 | 0.9983 | 0.6744 | 0.9828 |
| (+9GFP)- | 500 nM | | | 0.9995 | 0.7423 | 0.9647 | 0.5645 | 0.9984 | 0.7636 |
| $(GGGGS)_4$- | 1 μM | | | | 0.971 | 0.9998 | 0.9163 | 1 | 0.9809 |
| (IGF-1) (SEQ ID NO: 7) | 2 μM | | | | | 0.9996 | 1 | 0.9903 | 1 |
| (+9GFP)- | 500 nM | | | | | | 0.9968 | 1 | 0.9999 |

TABLE 10-continued

Post hoc comparisons (using Tukey's HSD) for the data in FIG. 15C. p-values for the cumulative sGAG biosynthesis loss data in the 7-day experiment are shown in (Table A). p-values for the cumulative sGAG biosynthesis loss data in the 10-day experiment are shown in (Table B). Significant p-values (less than 0.05) are shown in bold font.

| | | | (+9GFP)-$(GGGGS)_4$-(IGF-1) (SEQ ID NO: 7) | | | (+9GFP)-$(EAAAK)_3$-(IGF-1) (SEQ ID NO: 8) | | | |
|---|---|---|---|---|---|---|---|---|---|
| | | IL-1β | 500 nM | 1 μM | 2 μM | 500 nM | 1 μM | 2 μM | IGF-1 |
| $(EAAAK)_3$-(IGF-1) (SEQ ID NO: 8) | 1 μM | | | | | | | 0.97 | 1 |
| | 2 μM | | | | | | | | 0.9953 |
| (B) 10-day experiment; ankle cartilage | | | | | | | | | |
| Untreated control | | **0.0372** | **0.0112** | 0.098 | 0.4045 | 0.2421 | 0.8905 | **0.0316** | 0.7847 |
| IL-1β | | | 1 | 1 | 0.9818 | 0.9986 | 0.6627 | 1 | 0.7978 |
| (+9GFP)-$(GGGGS)_4$-(IGF-1) (SEQ ID NO: 7) | 500 nM | | | 0.9982 | 0.8903 | 0.9759 | 0.4042 | 1 | 0.5517 |
| | 1 μM | | | | 0.9989 | 1 | 0.8649 | 1 | 0.9418 |
| | 2 μM | | | | | 1 | 0.9969 | 0.9749 | 0.9997 |
| (+9GFP)-$(EAAAK)_3$-(IGF-1) (SEQ ID NO: 8) | 500 nM | | | | | | 0.9739 | 0.9977 | 0.9937 |
| | 1 μM | | | | | | | 0.6255 | 1 |
| | 2 μM | | | | | | | | 0.7664 |

Example 4. Modifications of +15 GFP for Chemical Conjugation with Dexamethasone +15 GFP was chosen as the carrier for dexamethasone (a small molecule, anti-catabolic and antiinflammatory glucocorticoid). Two modifications of +15 GFP that had a thiol group at the N-terminus were created. The initial idea is to use maleimide and hydrazide crosslinkers that can react with the thiol group on the +15 GFP and a carbonyl group in dexamethasone to form a pHsensitive conjugate. The conjugate is expected to be relatively stable at physiological pH, and once the conjugate enters the endosomes/lysosomes of cartilage cells, it will break down at the lower pH and release the dexamethasone. In the first modification, a single cysteine group was added to the N-terminus of the +15 GFP (SEQ ID NO: 12). In the second modification, a cysteine group and a flexible protein linker ($(GGS)_9$ (SEQ ID NO: 29)) were included at the N-terminus of the +15 GFP (SEQ ID NO: 13). In both cases, the proteins were expressed in *E. coli* and purified using Ni-NTA resin followed by ion exchange chromatography. The complete details for these proteins is given in the Sequences section.

The two modified +15 GFP proteins were conjugated with dexamethasone via hydrazone and pyrophosphate diester linkers (FIGS. 22-25).

Having thus described several aspects of embodiments of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EMBODIMENTS

1. A method for delivering a payload molecule to a charged avascular tissue and/or a charged partially vascularized tissue in a subject, comprising:

administering to a subject in need thereof an effective amount of a carrier, wherein the carrier is a cationic carrier and/or has a surface charge distribution such that about 40% or greater of a continuous region of the surface is positively charged, and wherein the carrier is linked with a payload molecule, to deliver the payload molecule to the charged avascular tissue and/or the charged partially vascularized tissue.

2 The method of paragraph 1, wherein the carrier is a synthetic carrier or a natural carrier.

3 The method of paragraph 1 or 2, wherein the carrier is a peptide carrier or a nanoparticle.

4. The method of any one of paragraphs 1-3, wherein the charged avascular tissue and/or the partially vascularized tissue is articular cartilage, an intervertebral disc, meniscus, cornea, tracheal cartilage, costal cartilage, nasal cartilage, auricular cartilage, a tendon, or a ligament.

5. The method of any one of paragraphs 1-4, wherein the carrier has a hydrodynamic diameter of less than 15 nm.

6. The method of any one of paragraphs 1-5, wherein the payload molecule is delivered to the extracellular space of the charged avascular tissue or the charged partially vascularized tissue.

7. The method of any one of paragraphs 1-6, wherein the carrier has a net neutral charge.

8. The method of paragraph 7, wherein the carrier has a surface charge distribution such that about 40% or greater of a continuous region of the surface is positively charged.

9. The method of paragraph 8, wherein the carrier is an engineered green fluorescence protein (GFP) having an amino acid sequence that is at least 80% identical to the amino acid sequence of SEQ ID NO: 5.

10. The method of any one of paragraphs 1-6, wherein the carrier has a net positive charge.

11. The method of paragraph 10, wherein the carrier has a net positive charge of +6 to +20.

12. The method of paragraph 11, wherein the carrier has a net positive charge of +9 to +15.

13. The method of paragraph 12, wherein the carrier has a net positive charge of +9.

14. The method of paragraph 13, wherein the carrier is an engineered super charged green fluorescence protein (S-GFP) having an amino acid sequence that is at least 80% identical to the amino acid sequence of SEQ ID NO: 1.

15. The method of paragraph 12, wherein the carrier has a net positive charge of +15.

16. The method of paragraph 15, wherein the synthetic peptide carrier is an engineered super charged green fluorescent protein (S-GFP) having an amino acid sequence that is at least 80% identical to the amino acid sequence of SEQ ID NO: 2, SEQ ID NO: 12, or SEQ ID NO: 13.

17. The method of any one of paragraphs 1-4, wherein the payload molecule is delivered to cells in the charged avascular tissue or the partially vascularized tissue.

18. The method of paragraph 17, wherein the payload molecule is delivered to the cell surface.

19. The method of paragraph 17, wherein the payload molecule is delivered to the intracellular space of the cells.

20. The method of any one of paragraphs 17-19, wherein the carrier has a net positive charge.

21. The method of paragraph 20, wherein the carrier has a net positive charge of +12 to +48.

22. The method of paragraph 21, wherein the carrier has a net positive charge of +15 to +36.

23. The method of paragraph 22, wherein the carrier has a net positive charge of +15.

24. The method of paragraph 22, wherein the carrier has a net positive charge of +25.

25. The method of paragraph 24, wherein the carrier is an engineered super charged green fluorescence protein (S-GFP) having an amino acid sequence that is at least 80% identical to the amino acid sequence of SEQ ID NO: 3.

26. The method of paragraph 22, wherein the carrier has a net positive charge of +36.

27. The method of paragraph 26, wherein the carrier is an engineered super charged green fluorescence protein (GFP) having an amino acid sequence that is at least 80% identical to the amino acid sequence of SEQ ID NO: 4.

28. The method of any one of paragraphs 1-27, wherein the payload molecule is a protein, a small molecule, a nucleic acid, or an imaging molecule.

29. The method of paragraph 28, wherein the payload molecule is a protein.

30. The method of paragraph 29, wherein the protein is an insulin growth factor-1 (IGF-1), a Cas protein, FGF-18, an antibody, or IL-1Ra.

31. The method of paragraph 30, wherein the antibody is an anti-TNF antibody, an anti-SOST antibody, an anti-matrix metalloproteinase antibody, or an anti-aggrecanase antibody.

32. The method of paragraph 28, wherein the payload molecule is a small molecule or a pharmaceutically acceptable salt thereof.

33. The method of paragraph 32, wherein the small molecule is dexamethasone, a corticosteroid (e.g., triamcinolone, prednisolone), a TLR inhibitor (e.g., TAK-242, o-vanillin), a senolytics (e.g., navitoclax), a kinase inhibitors (e.g., SP600125 (JNK1/2 inhibitor), an ERK-5 inhibitor (e.g., XMD8-92), a JAK3 inhibitor (e.g., CP690550), a strontium ranelate, or a kartogenin.

34. The method of paragraph 33, wherein the small molecule is dexamethasone.

35. The method of any one of paragraphs 1-34, wherein the carrier further comprises a cysteine at the N-terminus.

36. The method of any one of paragraphs 1-35, wherein the carrier further comprises a linker.

37. The method of paragraph 36, wherein the linker is a flexible linker or a rigid linker.

38. The method of paragraph 37, wherein the flexible linker is (GGGGS)4 (SEQ ID NO: 27), (GGGGS)3 (SEQ ID NO: 28) or (GGS)9 (SEQ ID NO: 29).

39. The method of paragraph 37, wherein the rigid linker is (EAAAK)3 (SEQ ID NO: 30) or A(EAAAK)4ALEA (EAAAK)4A (SEQ ID NO: 31).

40. The method of paragraph 36, wherein the linker is an acid cleavable linker or an enzyme cleavable linker.

41. The method of any one of paragraphs 36-40, wherein the linker is positioned between the carrier and the payload molecule.

42. The method of any one of paragraphs 36-41, wherein the payload molecule is released from the carrier by cleavage of the linker.

43. The method of any one of paragraphs 1-42, wherein the administration of the carrier is by local injection.

44. The method of any one of paragraphs 1-43, wherein the subject is a human.

45. The method of paragraph 44, wherein the subject has or is at risk of having joint disease, pseudogout, a genetic disorder, an autoimmune disorder, or a cancer.

46. The method of paragraph 45, wherein the joint disease is osteoarthritis, intervertebral disc degeneration or a muscularskeletal disease.

47. The method of paragraph 45, wherein the genetic disorder is chondrodysplasia, or mucopolysaccharidosis.

48. The method of paragraph 45, wherein the autoimmune disorder is relapsing polychondritis.

49. The method of paragraph 46, wherein the joint disease is osteoarthritis, and wherein the method comprises administering the subject a first carrier linked with a pro-anabolic protein and optionally, a second carrier linked with an anti-catabolic and/or anti-inflammatory small molecule.

50. The method of paragraph 49, wherein the first carrier linked with a pro-anabolic protein is a +9 super charged green fluorescent protein (+9 S-GFP) linked with an IGF-1.

51. The method of paragraph 49, wherein the second carrier linked with an anti-catabolic and/or anti-inflammatory small molecule is a +15 super charged green fluorescent protein (+15 S-GFP) linked with dexamethasone.

52. The method of paragraph 50, wherein the carrier comprises an amino acid sequence that is at least 80% identical to the amino acid sequence of any one of SEQ ID Nos. 6-13.

53. The method of paragraph 50, wherein the (+9 S-GFP) linked with an IGF-1 comprises an amino acid sequence that is at least 80% identical to the amino acid sequence of any one of SEQ ID NOs: 6-11.

54. The method of 51, wherein the +15 S-GFP comprises an amino acid sequence that is at least 80% identical to the amino acid sequence of SEQ ID NO: 12 or SEQ ID NO: 13.

55. The method of any one of paragraphs 1-43, wherein the subject is a non-human mammal.

56. A composition, comprising:
   a carrier, wherein the carrier is a cationic carrier and/or has a surface charge distribution such that about 40% or greater of a continuous region of the surface is positively charged, wherein the carrier is linked with a payload molecule.

57. The composition of paragraph 56, wherein the carrier is a synthetic carrier or a natural carrier.

58. The composition of paragraph 56 or 57, wherein the carrier is a peptide carrier or a nanoparticle.

59. The composition of any one of paragraphs 56-58, wherein the carrier is capable of delivering the payload molecule to a charged avascular tissue and/or a partially vascularized tissue.

60. The composition of any one of paragraphs 56-59, wherein the charged avascular tissue or the partially vascularized tissue is articular cartilage, an intervertebral disc, meniscus, cornea, tracheal cartilage, costal cartilage, nasal cartilage, auricular cartilage, a tendon, or a ligament.

63. The composition of any one of paragraphs 56-60, wherein the carrier has a hydrodynamic diameter of less than 15 nm.

64. The composition of any one of paragraphs 56-63, wherein the carrier is capable of delivering the payload molecule to the extracellular space of the charged avascular tissue and/or a partially vascularized tissue.

65. The composition of any one of paragraphs 56-64, wherein the carrier has a net neutral charge.

66. The composition of paragraph 65, wherein the carrier has a surface charge distribution such that about 40% or greater of a continuous region of the surface is positively charged.

67. The composition of paragraph 66, wherein the carrier is a engineered green fluorescence protein (GFP) having an amino acid sequence that is at least 80% identical to the amino acid sequence of SEQ ID NO: 5.

68. The composition of any one of paragraphs 56-64, wherein the carrier has a net positive charge.

69. The composition of paragraph 68, wherein the carrier has a net positive charge of +6 to +20.

70. The composition of paragraph 69, wherein the carrier has a net positive charge of +9 to +15.

71. The composition of paragraph 70, wherein the carrier has a net positive charge of +9.

72. The composition of paragraph 71, wherein the carrier is an engineered super charged green fluorescence protein (S-GFP) having an amino acid sequence that is at least 80% identical to the amino acid sequence of SEQ ID NO: 1.

73. The composition of paragraph 70, wherein the carrier has a net positive charge of +15.

74. The composition of paragraph 73, wherein the carrier is an engineered super charged green fluorescence protein (S-GFP) having an amino acid sequence that is at least 80% identical to the amino acid sequence of SEQ ID NO: 2, SEQ ID NO: 12, or SEQ ID NO: 13.

75. The composition of paragraph 56, wherein the carrier is capable of delivering the payload molecule to cells in the charged avascular tissue or the partially vascularized tissue.

76. The composition of paragraph 75, wherein the carrier is capable of delivering the payload molecule to the cell surface.

77. The composition of paragraph 75, wherein the carrier is capable of delivering the payload molecule to the intracellular space of the cells.

78. The composition of any one of paragraphs 75-77, wherein the carrier has a net positive charge.

79. The composition of paragraph 78, wherein the carrier has a net positive charge of +12 to +48

80. The composition of paragraph 79, wherein the carrier has a net positive charge of +15 to +36.

81. The composition of paragraph 80, wherein the carrier has a net positive charge of +15.

82. The composition of paragraph 80, wherein the carrier has a net positive charge of +25.

83. The composition of paragraph 82, wherein the carrier is an engineered super charged green fluorescence protein (S-GFP) having an amino acid sequence that is at least 80% identical to the amino acid sequence of SEQ ID NO: 3.

84. The composition of paragraph 80, wherein the carrier has a net positive charge of +36.

85. The composition of paragraph 84, wherein the carrier is an engineered super charged green fluorescence protein (S-GFP) having an amino acid sequence that is at least 80% identical to the amino acid sequence of SEQ ID NO: 4.

86. The composition of any one of paragraphs 56-85, wherein the carrier further comprises a cysteine at the N-terminus.

87. The composition of any one of paragraphs 56-86, wherein the payload molecule is a protein, a small molecule, a nucleic acid, or an imaging molecule.

88. The composition of paragraph 87, wherein the payload molecule is a protein.

89. The composition of paragraph 88, wherein the protein is an insulin growth factor-1 (IGF-1), a Cas protein, FGF-18, an antibody, or IL-1Ra.

90. The composition of paragraph 89, wherein the antibody is an anti-TNF antibody, an anti-SOST antibody, an anti-matrix metalloproteinase antibody, or an anti-aggrecanase antibody.

91. The composition of any paragraph 87, wherein the payload molecule is a small molecule or a pharmaceutically acceptable salt thereof.

92. The composition of paragraph 91, wherein the small molecule is dexamethasone, a corticosteroid (e.g., triamcinolone, prednisolone), a TLR inhibitor (e.g., TAK-242, o-vanillin), a senolytics (e.g., navitoclax), a kinase inhibitors (e.g., SP600125 (JNK1/2 inhibitor), an ERK-5 inhibitor (e.g., XMD8-92), a JAK3 inhibitor (e.g., CP690550), a strontium ranelate, or a kartogenin.

93. The composition of paragraph 92, wherein the small molecule is dexamethasone.

94. The composition of any one of paragraphs 56093, wherein the carrier further comprises a linker.

95. The composition of paragraph 94, wherein the linker is a flexible linker or a rigid linker.

96. The composition of paragraph 95, wherein the flexible linker is (GGGGS)4 (SEQ ID NO: 27), (GGGGS)3 (SEQ ID NO: 28) or (GGS)9 (SEQ ID NO: 29).

97. The composition of paragraph 95, wherein the rigid linker is (EAAAK)3 (SEQ ID NO: 30) or A(EAAAK)4ALEA(EAAAK)4A (SEQ ID NO: 31).

98. The composition of paragraph 94, wherein the linker is an acid cleavable linker or an enzyme cleavable linker.

99. The composition of any one of paragraphs 94-98, wherein the linker is positioned between the carrier and the payload molecule.

100. The composition of any one of paragraphs 94-99, wherein the payload molecule is released from the carrier by cleavage of the linker.

101. The composition of paragraph 100, wherein the carrier comprises an amino acid sequence that is at least 80% identical to the amino acid sequence of any one of SEQ ID NOs: 6-13.

102. The composition of any one of paragraphs 56-101, wherein the composition further comprises a pharmaceutically acceptable carrier.

103. The composition of paragraph 102, wherein the composition is formulated for local injection.

104. An isolated nucleic acid comprising a nucleic acid sequence that is at least 80% identical to the nucleotide sequence of any one of SEQ ID NOs: 14-26.

105. A method for treating a disease associated with a charged avascular tissue or a partially vascularized tissue in a subject in need thereof, comprising:

administering to a subject a therapeutically effective amount of the composition of any one of paragraphs 56-103, or the isolated nucleic acid of paragraph 104.

106. A method for identifying a carrier suitable for delivering a payload molecule to a charged avascular tissue or a partially vascularized tissue, comprising:

determining the net surface charge of the carrier for optimized tissue uptake;

determining the surface charge distribution of the carrier for optimized tissue uptake; and determining the linker for optimized tissue uptake.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method for delivering a payload molecule to a charged avascular tissue and/or a charged partially vascularized tissue in a subject, comprising:

intrasynovially administering to a subject in need thereof an effective amount of a carrier, wherein the carrier is an engineered green fluorescence protein (GFP) having an amino acid sequence that is at least 95% identical to the amino acid sequence of SEQ ID NO: 5; and wherein the carrier is linked with a payload molecule, to deliver the payload molecule to the charged avascular tissue and/or the charged partially vascularized tissue.

2. The method of claim 1, wherein the carrier is 100% identical to the amino acid sequence of SEQ ID NO: 5.

3. The method of claim 1, wherein the payload molecule is delivered to cells in the charged avascular tissue or the partially vascularized tissue.

4. The method of claim 1, wherein the payload molecule is a protein, a small molecule or a pharmaceutically acceptable salt thereof, a nucleic acid, or an imaging molecule.

5. The method of claim 4, wherein the payload molecule is a protein selected from an insulin growth factor-1 (IGF-1), a CRISPR associated (Cas) protein, fibroblast growth factor-18 (FGF-18), an antibody, or Interleukin-1 receptor antagonist (IL-1Ra).

6. The method of claim 4, wherein the payload molecule is a small molecule selected from dexamethasone, a corticosteroid, a Toll like receptor (TLR) inhibitor, a senolytic, a kinase inhibitor, a Janus kinase 3 (JAK3) inhibitor, strontium ranelate, and kartogenin.

7. The method of claim 1, wherein the subject has or is at risk of having joint disease, pseudogout, a genetic disorder, an autoimmune disorder, or a cancer.

8. The method of claim 7, wherein the subject has or is at risk of having osteoarthritis, intervertebral disc degeneration, a musculoskeletal disease, chondrodysplasia, mucopolysaccharidosis, or relapsing polychondritis.

9. The method of claim 8, wherein the subject has or is at risk of having osteoarthritis, and wherein the method comprises administering to the subject the carrier according to claim 5 linked with a pro-anabolic protein.

10. The method of claim 3, wherein the payload molecule is delivered to the cell surface or to the intracellular space of the cells.

11. The method of claim 1, wherein the carrier comprises a linker and wherein the linker is (i) a flexible linker selected from the group consisting of: $(GGGGS)_4$, $(GGGGS)_3$ and $(GGS)_9$; or (ii) a rigid linker selected from the group consisting of: $(EAAAK)_3$ and $A(EAAAK)_4ALEA(EAAAK)_4A$.

12. The method of claim 9, wherein the method comprises administering to the subject a second carrier according to claim 5 linked with an anti-catabolic and/or anti-inflammatory small molecule.

* * * * *

SEQUENCE LISTING

```
<160> NUMBER OF SEQ ID NOS: 49

<210> SEQ ID NO 1
```

<211> LENGTH: 248
<212> TYPE: PRT
<213> ORGANISM: Artificial Sequence
<220> FEATURE:
<223> OTHER INFORMATION: Synthetic

<400> SEQUENCE: 1

Met Gly His His His His His His Gly Gly Ala Ser Lys Gly Glu Glu
1 5 10 15

Leu Phe Thr Gly Val Val Pro Ile Leu Val Glu Leu Asp Gly Asp Val
20 25 30

Asn Gly His Lys Phe Ser Val Arg Gly Glu Gly Glu Gly Asp Ala Thr
35 40 45

Asn Gly Lys Leu Thr Leu Lys Phe Ile Cys Thr Thr Gly Lys Leu Pro
50 55 60

Val Pro Trp Pro Thr Leu Val Thr Thr Leu Thr Tyr Gly Val Gln Cys
65 70 75 80

Phe Ser Arg Tyr Pro Asp His Met Lys Arg His Asp Phe Phe Lys Ser
85 90 95

Ala Met Pro Lys Gly Tyr Val Gln Glu Arg Thr Ile Ser Phe Lys Lys
100 105 110

Asp Gly Lys Tyr Lys Thr Arg Ala Glu Val Lys Phe Glu Gly Arg Thr
115 120 125

Leu Val Asn Arg Ile Lys Leu Lys Gly Arg Asp Phe Lys Glu Lys Gly
130 135 140

Asn Ile Leu Gly His Lys Leu Arg Tyr Asn Phe Asn Ser His Lys Val
145 150 155 160

Tyr Ile Thr Ala Asp Lys Gln Lys Asn Gly Ile Lys Ala Asn Phe Lys
165 170 175

Ile Arg His Asn Val Glu Asp Gly Ser Val Gln Leu Ala Asp His Tyr
180 185 190

Gln Gln Asn Thr Pro Ile Gly Asp Gly Pro Val Leu Leu Pro Asp Asn
195 200 205

His Tyr Leu Ser Thr Gln Ser Ala Leu Ser Lys Asp Pro Asn Glu Lys
210 215 220

Arg Asp His Met Val Leu Leu Glu Phe Val Thr Ala Ala Gly Ile Thr
225 230 235 240

His Gly Met Asp Glu Leu Tyr Lys
245

<210> SEQ ID NO 2
<211> LENGTH: 248
<212> TYPE: PRT
<213> ORGANISM: Artificial Sequence
<220> FEATURE:
<223> OTHER INFORMATION: Synthetic

<400> SEQUENCE: 2

Met Gly His His His His His His Gly Gly Ala Ser Lys Gly Glu Arg
1 5 10 15

Leu Phe Thr Gly Val Val Pro Ile Leu Val Glu Leu Asp Gly Asp Val
20 25 30

Asn Gly His Lys Phe Ser Val Arg Gly Glu Gly Glu Gly Asp Ala Thr
35 40 45

Arg Gly Lys Leu Thr Leu Lys Phe Ile Cys Thr Thr Gly Lys Leu Pro
50 55 60

Val Pro Trp Pro Thr Leu Val Thr Thr Leu Thr Tyr Gly Val Gln Cys

-continued

```
65                  70                  75                  80

Phe Ser Arg Tyr Pro Lys His Met Lys Arg His Asp Phe Phe Lys Ser
                85                  90                  95

Ala Met Pro Glu Gly Tyr Val Gln Glu Arg Thr Ile Ser Phe Lys Lys
            100                 105                 110

Asp Gly Thr Tyr Lys Thr Arg Ala Glu Val Lys Phe Glu Gly Arg Thr
        115                 120                 125

Leu Val Asn Arg Ile Glu Leu Lys Gly Arg Asp Phe Lys Glu Lys Gly
    130                 135                 140

Asn Ile Leu Gly His Lys Leu Glu Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Ala Leu Ser Lys Asp Pro Lys Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245


<210> SEQ ID NO 3
<211> LENGTH: 248
<212> TYPE: PRT
<213> ORGANISM: Artificial Sequence
<220> FEATURE:
<223> OTHER INFORMATION: Synthetic

<400> SEQUENCE: 3

Met Gly His His His His His His Gly Gly Ala Ser Lys Gly Glu Arg
1               5                   10                  15

Leu Phe Thr Gly Val Val Pro Ile Leu Val Glu Leu Asp Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Thr Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Asn Val
145                 150                 155                 160

Tyr Ile Thr Ala Asp Lys Arg Lys Asn Gly Ile Lys Ala Asn Phe Lys
                165                 170                 175

Ile Arg His Asn Val Lys Asp Gly Ser Val Gln Leu Ala Asp His Tyr
```

-continued

```
            180                 185                 190

Gln Gln Asn Thr Pro Ile Gly Arg Gly Pro Val Leu Leu Pro Arg Asn
        195                 200                 205

His Tyr Leu Ser Thr Arg Ser Ala Leu Ser Lys Asp Pro Lys Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245


<210> SEQ ID NO 4
<211> LENGTH: 248
<212> TYPE: PRT
<213> ORGANISM: Artificial Sequence
<220> FEATURE:
<223> OTHER INFORMATION: Synthetic

<400> SEQUENCE: 4

Met Gly His His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Asp Glu Arg Tyr Lys
                245


<210> SEQ ID NO 5
<211> LENGTH: 253
<212> TYPE: PRT
<213> ORGANISM: Artificial Sequence
<220> FEATURE:
<223> OTHER INFORMATION: Synthetic
```

<400> SEQUENCE: 5

Met Gly His His His His His His Gly Ser Ala Cys Glu Leu Met Val
1               5                   10                  15

Ser Lys Gly Glu Glu Leu Phe Glu Gly Asp Val Pro Ile Leu Val Glu
            20                  25                  30

Leu Asp Gly Asp Val Asn Gly His Glu Phe Ser Val Arg Gly Glu Gly
        35                  40                  45

Glu Gly Asp Ala Thr Lys Gly Glu Leu Thr Leu Lys Phe Ile Cys Thr
    50                  55                  60

Thr Gly Glu Leu Pro Val Pro Trp Pro Thr Leu Val Thr Thr Leu Thr
65                  70                  75                  80

Tyr Gly Val Gln Cys Phe Ser Arg Tyr Pro Lys His Met Lys Gln His
                85                  90                  95

Asp Phe Phe Lys Ser Ala Met Pro Glu Gly Tyr Val Gln Glu Arg Thr
            100                 105                 110

Ile Ser Phe Lys Asp Asp Gly Thr Tyr Lys Thr Arg Ala Glu Val Lys
        115                 120                 125

Phe Glu Gly Asp Thr Leu Val Asn Arg Ile Glu Leu Lys Gly Lys Asp
    130                 135                 140

Phe Lys Glu Lys Gly Asn Ile Leu Gly His Lys Leu Glu Tyr Asn Phe
145                 150                 155                 160

Asn Ser His Arg Val Tyr Ile Thr Ala Asp Lys Arg Lys Asn Gly Ile
                165                 170                 175

Lys Ala Glu Phe Lys Ile Arg His Asn Val Lys Asp Gly Ser Val Gln
            180                 185                 190

Leu Ala Asp His Tyr Gln Gln Asn Thr Pro Ile Gly Arg Gly Pro Val
        195                 200                 205

Leu Leu Pro Arg Arg His Tyr Leu Ser Thr Arg Ser Ala Leu Ser Lys
    210                 215                 220

Asp Pro Lys Glu Glu Arg Asp His Met Val Leu Leu Glu Phe Val Thr
225                 230                 235                 240

Ala Ala Gly Ile Asp His Gly Met Asp Glu Leu Tyr Lys
                245                 250

<210> SEQ ID NO 6
<211> LENGTH: 316
<212> TYPE: PRT
<213> ORGANISM: Artificial Sequence
<220> FEATURE:
<223> OTHER INFORMATION: Synthetic

<400> SEQUENCE: 6

His His His His His His Gly Gly Ala Ser Lys Gly Glu Glu Leu Phe
1               5                   10                  15

Thr Gly Val Val Pro Ile Leu Val Glu Leu Asp Gly Asp Val Asn Gly
            20                  25                  30

His Lys Phe Ser Val Arg Gly Glu Gly Glu Gly Asp Ala Thr Asn Gly
        35                  40                  45

Lys Leu Thr Leu Lys Phe Ile Cys Thr Thr Gly Lys Leu Pro Val Pro
    50                  55                  60

Trp Pro Thr Leu Val Thr Thr Leu Thr Tyr Gly Val Gln Cys Phe Ser
65                  70                  75                  80

Arg Tyr Pro Asp His Met Lys Arg His Asp Phe Phe Lys Ser Ala Met
                85                  90                  95

-continued

```
Pro Lys Gly Tyr Val Gln Glu Arg Thr Ile Ser Phe Lys Lys Asp Gly
            100                 105                 110

Lys Tyr Lys Thr Arg Ala Glu Val Lys Phe Glu Gly Arg Thr Leu Val
        115                 120                 125

Asn Arg Ile Lys Leu Lys Gly Arg Asp Phe Lys Glu Lys Gly Asn Ile
    130                 135                 140

Leu Gly His Lys Leu Arg Tyr Asn Phe Asn Ser His Lys Val Tyr Ile
145                 150                 155                 160

Thr Ala Asp Lys Gln Lys Asn Gly Ile Lys Ala Asn Phe Lys Ile Arg
                165                 170                 175

His Asn Val Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205

Leu Ser Thr Gln Ser Ala Leu Ser Lys Asp Pro Asn Glu Lys Arg Asp
    210                 215                 220

His Met Val Leu Leu Glu Phe Val Thr Ala Ala Gly Ile Thr His Gly
225                 230                 235                 240

Met Asp Glu Leu Tyr Lys Gly Pro Glu Thr Leu Cys Gly Ala Glu Leu
                245                 250                 255

Val Asp Ala Leu Gln Phe Val Cys Gly Asp Arg Gly Phe Tyr Phe Asn
            260                 265                 270

Lys Pro Thr Gly Tyr Gly Ser Ser Ser Arg Arg Ala Pro Gln Thr Gly
        275                 280                 285

Ile Val Asp Glu Cys Cys Phe Arg Ser Cys Asp Leu Arg Arg Leu Glu
    290                 295                 300

Met Tyr Cys Ala Pro Leu Lys Pro Ala Lys Ser Ala
305                 310                 315
```

<210> SEQ ID NO 7
<211> LENGTH: 336
<212> TYPE: PRT
<213> ORGANISM: Artificial Sequence
<220> FEATURE:
<223> OTHER INFORMATION: Synthetic

<400> SEQUENCE: 7

```
His His His His His His Gly Gly Ala Ser Lys Gly Glu Glu Leu Phe
1               5                   10                  15

Thr Gly Val Val Pro Ile Leu Val Glu Leu Asp Gly Asp Val Asn Gly
            20                  25                  30

His Lys Phe Ser Val Arg Gly Glu Gly Glu Gly Asp Ala Thr Asn Gly
        35                  40                  45

Lys Leu Thr Leu Lys Phe Ile Cys Thr Thr Gly Lys Leu Pro Val Pro
    50                  55                  60

Trp Pro Thr Leu Val Thr Thr Leu Thr Tyr Gly Val Gln Cys Phe Ser
65                  70                  75                  80

Arg Tyr Pro Asp His Met Lys Arg His Asp Phe Phe Lys Ser Ala Met
                85                  90                  95

Pro Lys Gly Tyr Val Gln Glu Arg Thr Ile Ser Phe Lys Lys Asp Gly
            100                 105                 110

Lys Tyr Lys Thr Arg Ala Glu Val Lys Phe Glu Gly Arg Thr Leu Val
        115                 120                 125

Asn Arg Ile Lys Leu Lys Gly Arg Asp Phe Lys Glu Lys Gly Asn Ile
    130                 135                 140
```

```
Leu Gly His Lys Leu Arg Tyr Asn Phe Asn Ser His Lys Val Tyr Ile
145                 150                 155                 160

Thr Ala Asp Lys Gln Lys Asn Gly Ile Lys Ala Asn Phe Lys Ile Arg
                165                 170                 175

His Asn Val Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205

Leu Ser Thr Gln Ser Ala Leu Ser Lys Asp Pro Asn Glu Lys Arg Asp
    210                 215                 220

His Met Val Leu Leu Glu Phe Val Thr Ala Ala Gly Ile Thr His Gly
225                 230                 235                 240

Met Asp Glu Leu Tyr Lys Gly Gly Gly Gly Ser Gly Gly Gly Gly Ser
                245                 250                 255

Gly Gly Gly Gly Ser Gly Gly Gly Gly Ser Gly Pro Glu Thr Leu Cys
            260                 265                 270

Gly Ala Glu Leu Val Asp Ala Leu Gln Phe Val Cys Gly Asp Arg Gly
        275                 280                 285

Phe Tyr Phe Asn Lys Pro Thr Gly Tyr Gly Ser Ser Ser Arg Arg Ala
    290                 295                 300

Pro Gln Thr Gly Ile Val Asp Glu Cys Cys Phe Arg Ser Cys Asp Leu
305                 310                 315                 320

Arg Arg Leu Glu Met Tyr Cys Ala Pro Leu Lys Pro Ala Lys Ser Ala
                325                 330                 335
```

<210> SEQ ID NO 8
<211> LENGTH: 331
<212> TYPE: PRT
<213> ORGANISM: Artificial Sequence
<220> FEATURE:
<223> OTHER INFORMATION: Synthetic

<400> SEQUENCE: 8

```
His His His His His His Gly Gly Ala Ser Lys Gly Glu Glu Leu Phe
1               5                   10                  15

Thr Gly Val Val Pro Ile Leu Val Glu Leu Asp Gly Asp Val Asn Gly
            20                  25                  30

His Lys Phe Ser Val Arg Gly Glu Gly Glu Gly Asp Ala Thr Asn Gly
        35                  40                  45

Lys Leu Thr Leu Lys Phe Ile Cys Thr Thr Gly Lys Leu Pro Val Pro
    50                  55                  60

Trp Pro Thr Leu Val Thr Thr Leu Thr Tyr Gly Val Gln Cys Phe Ser
65                  70                  75                  80

Arg Tyr Pro Asp His Met Lys Arg His Asp Phe Phe Lys Ser Ala Met
                85                  90                  95

Pro Lys Gly Tyr Val Gln Glu Arg Thr Ile Ser Phe Lys Lys Asp Gly
            100                 105                 110

Lys Tyr Lys Thr Arg Ala Glu Val Lys Phe Glu Gly Arg Thr Leu Val
        115                 120                 125

Asn Arg Ile Lys Leu Lys Gly Arg Asp Phe Lys Glu Lys Gly Asn Ile
    130                 135                 140

Leu Gly His Lys Leu Arg Tyr Asn Phe Asn Ser His Lys Val Tyr Ile
145                 150                 155                 160

Thr Ala Asp Lys Gln Lys Asn Gly Ile Lys Ala Asn Phe Lys Ile Arg
                165                 170                 175
```

```
His Asn Val Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205

Leu Ser Thr Gln Ser Ala Leu Ser Lys Asp Pro Asn Glu Lys Arg Asp
    210                 215                 220

His Met Val Leu Leu Glu Phe Val Thr Ala Ala Gly Ile Thr His Gly
225                 230                 235                 240

Met Asp Glu Leu Tyr Lys Glu Ala Ala Ala Lys Glu Ala Ala Ala Lys
                245                 250                 255

Glu Ala Ala Ala Lys Gly Pro Glu Thr Leu Cys Gly Ala Glu Leu Val
            260                 265                 270

Asp Ala Leu Gln Phe Val Cys Gly Asp Arg Gly Phe Tyr Phe Asn Lys
        275                 280                 285

Pro Thr Gly Tyr Gly Ser Ser Ser Arg Arg Ala Pro Gln Thr Gly Ile
    290                 295                 300

Val Asp Glu Cys Cys Phe Arg Ser Cys Asp Leu Arg Arg Leu Glu Met
305                 310                 315                 320

Tyr Cys Ala Pro Leu Lys Pro Ala Lys Ser Ala
                325                 330
```

<210> SEQ ID NO 9
<211> LENGTH: 331
<212> TYPE: PRT
<213> ORGANISM: Artificial Sequence
<220> FEATURE:
<223> OTHER INFORMATION: Synthetic

<400> SEQUENCE: 9

```
His His His His His His Gly Gly Ala Ser Lys Gly Glu Glu Leu Phe
1               5                   10                  15

Thr Gly Val Val Pro Ile Leu Val Glu Leu Asp Gly Asp Val Asn Gly
            20                  25                  30

His Lys Phe Ser Val Arg Gly Glu Gly Glu Gly Asp Ala Thr Asn Gly
        35                  40                  45

Lys Leu Thr Leu Lys Phe Ile Cys Thr Thr Gly Lys Leu Pro Val Pro
    50                  55                  60

Trp Pro Thr Leu Val Thr Thr Leu Thr Tyr Gly Val Gln Cys Phe Ser
65                  70                  75                  80

Arg Tyr Pro Asp His Met Lys Arg His Asp Phe Phe Lys Ser Ala Met
                85                  90                  95

Pro Lys Gly Tyr Val Gln Glu Arg Thr Ile Ser Phe Lys Lys Asp Gly
            100                 105                 110

Lys Tyr Lys Thr Arg Ala Glu Val Lys Phe Glu Gly Arg Thr Leu Val
        115                 120                 125

Asn Arg Ile Lys Leu Lys Gly Arg Asp Phe Lys Glu Lys Gly Asn Ile
    130                 135                 140

Leu Gly His Lys Leu Arg Tyr Asn Phe Asn Ser His Lys Val Tyr Ile
145                 150                 155                 160

Thr Ala Asp Lys Gln Lys Asn Gly Ile Lys Ala Asn Phe Lys Ile Arg
                165                 170                 175

His Asn Val Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205
```

```
Leu Ser Thr Gln Ser Ala Leu Ser Lys Asp Pro Asn Glu Lys Arg Asp
    210                 215                 220

His Met Val Leu Leu Glu Phe Val Thr Ala Ala Gly Ile Thr His Gly
225                 230                 235                 240

Met Asp Glu Leu Tyr Lys Gly Gly Gly Gly Ser Gly Gly Gly Gly Ser
                245                 250                 255

Gly Gly Gly Gly Ser Gly Pro Glu Thr Leu Cys Gly Ala Glu Leu Val
            260                 265                 270

Asp Ala Leu Gln Phe Val Cys Gly Asp Arg Gly Phe Tyr Phe Asn Lys
        275                 280                 285

Pro Thr Gly Tyr Gly Ser Ser Ser Arg Arg Ala Pro Gln Thr Gly Ile
    290                 295                 300

Val Asp Glu Cys Cys Phe Arg Ser Cys Asp Leu Arg Arg Leu Glu Met
305                 310                 315                 320

Tyr Cys Ala Pro Leu Lys Pro Ala Lys Ser Ala
                325                 330


<210> SEQ ID NO 10
<211> LENGTH: 343
<212> TYPE: PRT
<213> ORGANISM: Artificial Sequence
<220> FEATURE:
<223> OTHER INFORMATION: Synthetic

<400> SEQUENCE: 10

His His His His His His Gly Gly Ala Ser Lys Gly Glu Glu Leu Phe
1               5                   10                  15

Thr Gly Val Val Pro Ile Leu Val Glu Leu Asp Gly Asp Val Asn Gly
            20                  25                  30

His Lys Phe Ser Val Arg Gly Glu Gly Glu Gly Asp Ala Thr Asn Gly
        35                  40                  45

Lys Leu Thr Leu Lys Phe Ile Cys Thr Thr Gly Lys Leu Pro Val Pro
    50                  55                  60

Trp Pro Thr Leu Val Thr Thr Leu Thr Tyr Gly Val Gln Cys Phe Ser
65                  70                  75                  80

Arg Tyr Pro Asp His Met Lys Arg His Asp Phe Phe Lys Ser Ala Met
                85                  90                  95

Pro Lys Gly Tyr Val Gln Glu Arg Thr Ile Ser Phe Lys Lys Asp Gly
            100                 105                 110

Lys Tyr Lys Thr Arg Ala Glu Val Lys Phe Glu Gly Arg Thr Leu Val
        115                 120                 125

Asn Arg Ile Lys Leu Lys Gly Arg Asp Phe Lys Glu Lys Gly Asn Ile
    130                 135                 140

Leu Gly His Lys Leu Arg Tyr Asn Phe Asn Ser His Lys Val Tyr Ile
145                 150                 155                 160

Thr Ala Asp Lys Gln Lys Asn Gly Ile Lys Ala Asn Phe Lys Ile Arg
                165                 170                 175

His Asn Val Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205

Leu Ser Thr Gln Ser Ala Leu Ser Lys Asp Pro Asn Glu Lys Arg Asp
    210                 215                 220

His Met Val Leu Leu Glu Phe Val Thr Ala Ala Gly Ile Thr His Gly
225                 230                 235                 240
```

```
Met Asp Glu Leu Tyr Lys Gly Gly Ser Gly Gly Ser Gly Gly Ser Gly
                245                 250                 255

Gly Ser Gly Gly Ser Gly Gly Ser Gly Gly Ser Gly Gly Ser Gly Gly
            260                 265                 270

Ser Gly Pro Glu Thr Leu Cys Gly Ala Glu Leu Val Asp Ala Leu Gln
        275                 280                 285

Phe Val Cys Gly Asp Arg Gly Phe Tyr Phe Asn Lys Pro Thr Gly Tyr
    290                 295                 300

Gly Ser Ser Ser Arg Arg Ala Pro Gln Thr Gly Ile Val Asp Glu Cys
305                 310                 315                 320

Cys Phe Arg Ser Cys Asp Leu Arg Arg Leu Glu Met Tyr Cys Ala Pro
                325                 330                 335

Leu Lys Pro Ala Lys Ser Ala
            340
```

<210> SEQ ID NO 11
<211> LENGTH: 362
<212> TYPE: PRT
<213> ORGANISM: Artificial Sequence
<220> FEATURE:
<223> OTHER INFORMATION: Synthetic

<400> SEQUENCE: 11

```
His His His His His His Gly Gly Ala Ser Lys Gly Glu Glu Leu Phe
1               5                   10                  15

Thr Gly Val Val Pro Ile Leu Val Glu Leu Asp Gly Asp Val Asn Gly
            20                  25                  30

His Lys Phe Ser Val Arg Gly Glu Gly Glu Gly Asp Ala Thr Asn Gly
        35                  40                  45

Lys Leu Thr Leu Lys Phe Ile Cys Thr Thr Gly Lys Leu Pro Val Pro
    50                  55                  60

Trp Pro Thr Leu Val Thr Thr Leu Thr Tyr Gly Val Gln Cys Phe Ser
65                  70                  75                  80

Arg Tyr Pro Asp His Met Lys Arg His Asp Phe Phe Lys Ser Ala Met
                85                  90                  95

Pro Lys Gly Tyr Val Gln Glu Arg Thr Ile Ser Phe Lys Lys Asp Gly
            100                 105                 110

Lys Tyr Lys Thr Arg Ala Glu Val Lys Phe Glu Gly Arg Thr Leu Val
        115                 120                 125

Asn Arg Ile Lys Leu Lys Gly Arg Asp Phe Lys Glu Lys Gly Asn Ile
    130                 135                 140

Leu Gly His Lys Leu Arg Tyr Asn Phe Asn Ser His Lys Val Tyr Ile
145                 150                 155                 160

Thr Ala Asp Lys Gln Lys Asn Gly Ile Lys Ala Asn Phe Lys Ile Arg
                165                 170                 175

His Asn Val Glu Asp Gly Ser Val Gln Leu Ala Asp His Tyr Gln Gln
            180                 185                 190

Asn Thr Pro Ile Gly Asp Gly Pro Val Leu Leu Pro Asp Asn His Tyr
        195                 200                 205

Leu Ser Thr Gln Ser Ala Leu Ser Lys Asp Pro Asn Glu Lys Arg Asp
    210                 215                 220

His Met Val Leu Leu Glu Phe Val Thr Ala Ala Gly Ile Thr His Gly
225                 230                 235                 240

Met Asp Glu Leu Tyr Lys Ala Glu Ala Ala Ala Lys Glu Ala Ala Ala
                245                 250                 255
```

-continued

```
Lys Glu Ala Ala Ala Lys Glu Ala Ala Ala Lys Ala Leu Glu Ala Glu
            260                 265                 270

Ala Ala Ala Lys Glu Ala Ala Ala Lys Glu Ala Ala Ala Lys Glu Ala
        275                 280                 285

Ala Ala Lys Ala Gly Pro Glu Thr Leu Cys Gly Ala Glu Leu Val Asp
    290                 295                 300

Ala Leu Gln Phe Val Cys Gly Asp Arg Gly Phe Tyr Phe Asn Lys Pro
305                 310                 315                 320

Thr Gly Tyr Gly Ser Ser Ser Arg Arg Ala Pro Gln Thr Gly Ile Val
                325                 330                 335

Asp Glu Cys Cys Phe Arg Ser Cys Asp Leu Arg Arg Leu Glu Met Tyr
            340                 345                 350

Cys Ala Pro Leu Lys Pro Ala Lys Ser Ala
        355                 360


<210> SEQ ID NO 12
<211> LENGTH: 247
<212> TYPE: PRT
<213> ORGANISM: Artificial Sequence
<220> FEATURE:
<223> OTHER INFORMATION: Synthetic

<400> SEQUENCE: 12

Cys His His His His His His Gly Gly Ala Ser Lys Gly Glu Arg Leu
1               5                   10                  15

Phe Thr Gly Val Val Pro Ile Leu Val Glu Leu Asp Gly Asp Val Asn
            20                  25                  30

Gly His Lys Phe Ser Val Arg Gly Glu Gly Glu Gly Asp Ala Thr Arg
        35                  40                  45

Gly Lys Leu Thr Leu Lys Phe Ile Cys Thr Thr Gly Lys Leu Pro Val
    50                  55                  60

Pro Trp Pro Thr Leu Val Thr Thr Leu Thr Tyr Gly Val Gln Cys Phe
65                  70                  75                  80

Ser Arg Tyr Pro Lys His Met Lys Arg His Asp Phe Phe Lys Ser Ala
                85                  90                  95

Met Pro Glu Gly Tyr Val Gln Glu Arg Thr Ile Ser Phe Lys Lys Asp
            100                 105                 110

Gly Thr Tyr Lys Thr Arg Ala Glu Val Lys Phe Glu Gly Arg Thr Leu
        115                 120                 125

Val Asn Arg Ile Glu Leu Lys Gly Arg Asp Phe Lys Glu Lys Gly Asn
    130                 135                 140

Ile Leu Gly His Lys Leu Glu Tyr Asn Phe Asn Ser His Asn Val Tyr
145                 150                 155                 160

Ile Thr Ala Asp Lys Arg Lys Asn Gly Ile Lys Ala Asn Phe Lys Ile
                165                 170                 175

Arg His Asn Val Lys Asp Gly Ser Val Gln Leu Ala Asp His Tyr Gln
            180                 185                 190

Gln Asn Thr Pro Ile Gly Arg Gly Pro Val Leu Leu Pro Arg Asn His
        195                 200                 205

Tyr Leu Ser Thr Arg Ser Ala Leu Ser Lys Asp Pro Lys Glu Lys Arg
    210                 215                 220

Asp His Met Val Leu Leu Glu Phe Val Thr Ala Ala Gly Ile Thr His
225                 230                 235                 240

Gly Met Asp Glu Leu Tyr Lys
                245
```

<210> SEQ ID NO 13
<211> LENGTH: 274
<212> TYPE: PRT
<213> ORGANISM: Artificial Sequence
<220> FEATURE:
<223> OTHER INFORMATION: Synthetic

<400> SEQUENCE: 13

```
Cys His His His His His His Gly Gly Ser Gly Gly Ser Gly Gly Ser
1               5                   10                  15

Gly Gly Ser Gly Gly Ser Gly Gly Ser Gly Gly Ser Gly Gly Ser Gly
            20                  25                  30

Gly Ser Gly Gly Ala Ser Lys Gly Glu Arg Leu Phe Thr Gly Val Val
        35                  40                  45

Pro Ile Leu Val Glu Leu Asp Gly Asp Val Asn Gly His Lys Phe Ser
    50                  55                  60

Val Arg Gly Glu Gly Glu Gly Asp Ala Thr Arg Gly Lys Leu Thr Leu
65                  70                  75                  80

Lys Phe Ile Cys Thr Thr Gly Lys Leu Pro Val Pro Trp Pro Thr Leu
                85                  90                  95

Val Thr Thr Leu Thr Tyr Gly Val Gln Cys Phe Ser Arg Tyr Pro Lys
            100                 105                 110

His Met Lys Arg His Asp Phe Phe Lys Ser Ala Met Pro Glu Gly Tyr
        115                 120                 125

Val Gln Glu Arg Thr Ile Ser Phe Lys Lys Asp Gly Thr Tyr Lys Thr
    130                 135                 140

Arg Ala Glu Val Lys Phe Glu Gly Arg Thr Leu Val Asn Arg Ile Glu
145                 150                 155                 160

Leu Lys Gly Arg Asp Phe Lys Glu Lys Gly Asn Ile Leu Gly His Lys
                165                 170                 175

Leu Glu Tyr Asn Phe Asn Ser His Asn Val Tyr Ile Thr Ala Asp Lys
            180                 185                 190

Arg Lys Asn Gly Ile Lys Ala Asn Phe Lys Ile Arg His Asn Val Lys
        195                 200                 205

Asp Gly Ser Val Gln Leu Ala Asp His Tyr Gln Gln Asn Thr Pro Ile
    210                 215                 220

Gly Arg Gly Pro Val Leu Leu Pro Arg Asn His Tyr Leu Ser Thr Arg
225                 230                 235                 240

Ser Ala Leu Ser Lys Asp Pro Lys Glu Lys Arg Asp His Met Val Leu
                245                 250                 255

Leu Glu Phe Val Thr Ala Ala Gly Ile Thr His Gly Met Asp Glu Leu
            260                 265                 270

Tyr Lys
```

<210> SEQ ID NO 14
<211> LENGTH: 744
<212> TYPE: DNA
<213> ORGANISM: Artificial Sequence
<220> FEATURE:
<223> OTHER INFORMATION: Synthetic

<400> SEQUENCE: 14

```
atgggtcatc accaccacca tcacggtggc gctagcaaag gtgaagagct gtttacgggt      60

gtagtaccga tcttagtgga attagacggc gacgtgaacg gtcacaaatt tagcgtgcgc     120

ggcgaaggcg aaggtgacgc taccaatggt aaattgaccc tgaagtttat ttgcacaaca     180
```

ggcaaattac ccgttccgtg gcccacctta gtgaccaccc tgacctatgg cgttcagtgc 240
ttcagtcgtt acccagatca tatgaaacgt cacgattttt tcaaatcagc catgcctaaa 300
ggatatgttc aagagcgtac aatcagcttc aagaaggatg gcaaatataa aacgcgtgcg 360
gaagtgaaat ttgaaggccg cacattagta aatcgtatca aactgaaagg tcgtgacttc 420
aaagaaaaag gcaacatttt aggccataaa ctgcgttata actttaattc tcataaggtg 480
tatattacgg ccgataaaca gaaaaacggt atcaaggcaa atttcaaaat tcgccataac 540
gtggaagacg gcagcgttca attagcggat cattatcaac aaaacacgcc gattggtgac 600
gggcctgtac tgttacctga caaccactac ctgagcaccc agtcagcact gagcaaagat 660
ccgaacgaaa aacgcgatca catggttctg ttagaattcg tgaccgctgc aggcattact 720
cacggaatgg acgaactcta caag 744

<210> SEQ ID NO 15
<211> LENGTH: 744
<212> TYPE: DNA
<213> ORGANISM: Artificial Sequence
<220> FEATURE:
<223> OTHER INFORMATION: Synthetic

<400> SEQUENCE: 15
atgggtcatc accaccacca tcacggtggc gctagcaaag gtgaacgtct gtttacgggt 60
gtagtaccga tcttagtgga attagacggc gacgtgaacg gtcacaaatt tagcgtgcgc 120
ggcgaaggcg aaggtgacgc tacccgtggt aaattgaccc tgaagtttat ttgcacaaca 180
ggcaaattac ccgttccgtg gcccacctta gtgaccaccc tgacctatgg cgttcagtgc 240
ttcagtcgtt accctaaaca tatgaaacgt cacgattttt tcaaatcagc catgcctgaa 300
ggatatgttc aagagcgtac aatcagcttc aagaaggatg gcacctataa aacgcgtgcg 360
gaagtgaaat ttgaaggccg cacattagta aaccgtatcg aactgaaagg tcgtgacttc 420
aaagaaaaag gcaacatttt aggccataag ctggaatata actttaattc tcataacgtg 480
tatattacgg ccgataaacg caagaatggt atcaaggcaa atttcaaaat tcgccataac 540
gtgaaagacg gcagcgttca attagcggat cattatcaac aaaacacgcc gattggtcgc 600
gggcctgtac tgttacctcg caaccactac ctgagcaccc gttcagcact gagcaaagat 660
ccgaaagaaa aacgcgatca catggttctg ttagaattcg tgaccgctgc aggcattact 720
cacggaatgg acgaactcta caag 744

<210> SEQ ID NO 16
<211> LENGTH: 744
<212> TYPE: DNA
<213> ORGANISM: Artificial Sequence
<220> FEATURE:
<223> OTHER INFORMATION: Synthetic

<400> SEQUENCE: 16
atgggtcatc accaccacca tcacggtggc gctagcaaag gtgaacgtct gtttacgggt 60
gtagtaccga tcttagtgga attagacggc gacgtgaacg gtcataaatt tagcgtgcgc 120
ggcaaaggca aaggtgacgc tacccgtggt aaattgaccc tgaagtttat ttgcacaaca 180
ggcaaattac ccgttccgtg gcccacctta gtgaccaccc tgacctatgg cgttcagtgc 240
ttcagtcgtt accctaaaca tatgaaacgt cacgattttt tcaaatcagc catgcctaaa 300
ggatatgttc aagagcgtac aatcagcttc aagaaggatg gcacctataa aacgcgtgcg 360
gaagtgaaat ttgaaggccg cacattagta aatcgtatca aactgaaagg tcgtgacttc 420
aaagaaaaag gcaacatttt aggccataag ctgcgttata actttaattc tcataacgtg 480
tatattacgg ccgataaacg caagaatggt atcaaggcaa atttcaaaat tcgccataac 540
gtgaaagacg gcagcgttca attagcggat cattatcaac aaaacacgcc gattggtcgc 600
gggcctgtac tgttacctcg caaccactac ctgagcaccc gttcagcact gagcaaagat 660
ccgaaagaaa aacgcgatca catggttctg ttagaattcg tgaccgctgc aggcattact 720
cacggaatgg acgaactcta caag 744

<210> SEQ ID NO 17
<211> LENGTH: 744
<212> TYPE: DNA
<213> ORGANISM: Artificial Sequence
<220> FEATURE:
<223> OTHER INFORMATION: Synthetic

<400> SEQUENCE: 17
atgggtcatc accaccacca tcacggtggc gctagcaaag gtgaacgtct gtttcgtggt 60
aaagtaccga tcttagtgga attaaagggc gacgtgaacg gtcataaatt tagcgtgcgc 120
ggcaaaggca aaggtgacgc tacccgtggt aaattgaccc tgaagtttat ttgcacaaca 180
ggcaaattac ccgttccgtg gcccacctta gtgaccaccc tgacctatgg cgttcagtgc 240
ttcagtcgtt accctaaaca tatgaaacgt cacgattttt tcaaatcagc catgcctaaa 300
ggatatgttc aagagcgtac aatcagcttc aagaaggatg gcaaatataa aacgcgtgcg 360
gaagtgaaat ttgaaggccg cacattagta aatcgtatca aactgaaagg tcgtgacttc 420
aaagaaaaag gcaacatttt aggccataaa ctgcgttata actttaattc tcataaggtg 480
tatattacgg ccgataaacg caagaatggt atcaaggcaa aattcaaaat tcgccataac 540
gtgaaagacg gcagcgttca attagcggat cattatcaac aaaacacgcc gattggtcgc 600
gggcctgtac tgttacctcg caaccactac ctgagcaccc gttctaaact gagcaaagat 660
ccgaaagaaa aacgcgatca catggttctg ttagaattcg tgaccgctgc aggcattaag 720
cacggacgcg acgaacgcta caag 744

<210> SEQ ID NO 18
<211> LENGTH: 759
<212> TYPE: DNA
<213> ORGANISM: Artificial Sequence
<220> FEATURE:
<223> OTHER INFORMATION: Synthetic

<400> SEQUENCE: 18
atgggtcacc accaccacca ccacggtagc gcgtgcgagc tgatggttag caaaggcgag 60
gaactgttcg agggtgacgt gccgatcctg gttgaactgg acggcgatgt gaacggtcac 120
gaatttagcg ttcgtggtga gggcgaaggt gatgcgacca agggcgagct gaccctgaaa 180
ttcatttgca ccaccggtga actgccggtg ccgtggccga ccctggttac caccctgacc 240
tacggtgtgc agtgctttag ccgttatccg aagcacatga aacaacacga cttctttaag 300
agcgcgatgc cggagggcta cgttcaggaa cgtaccatca gcttcaagga cgatggtacc 360
tataaaaccc gtgcggaagt gaagtttgaa ggcgacaccc tggttaaccg tatcgagctg 420
aagggtaaag atttcaagga aaaaggcaac attctgggtc acaaactgga gtacaacttt 480
aacagccacc gtgtgtatat caccgcggat aagcgtaaaa acggcatcaa ggcggaattt 540
aaaattcgtc acaacgtgaa ggacggtagc gttcaactgg cggatcacta ccagcaaaac 600

-continued

```
accccgattg gtcgtggtcc ggttctgctg ccgcgtcgtc actatctgag cacccgtagc    660

gcgctgagca aggacccgaa agaggaacgt gatcacatgg tgctgctgga gttcgttacc    720

gcggcgggca ttgaccacgg tatggatgaa ctgtacaaa                           759
```

<210> SEQ ID NO 19
<211> LENGTH: 963
<212> TYPE: DNA
<213> ORGANISM: Artificial Sequence
<220> FEATURE:
<223> OTHER INFORMATION: Synthetic

<400> SEQUENCE: 19

```
catatgcatc atcatcatca tcatggcggt gcgagcaagg gcgaagaact gtttaccggc     60

gttgtgccga ttctggttga actggacggc gatgtgaacg gccacaagtt cagcgttcgt    120

ggtgagggcg aaggtgatgc gaccaacggc aagctgaccc tgaaatttat ctgcaccacc    180

ggtaaactgc cggtgccgtg gccgaccctg gttaccaccc tgacctacgg tgtgcagtgc    240

ttcagccgtt atccggacca catgaagcgt cacgatttct ttaagagcgc gatgccgaaa    300

ggctacgttc aagaacgtac cattagcttc aagaaagacg gcaagtataa aacccgtgcg    360

gaagtgaaat ttgaaggccg taccctggtt aaccgtatca agctgaaagg tcgtgatttc    420

aaggagaaag gcaacattct gggtcacaag ctgcgttaca actttaacag ccacaaagtg    480

tatatcaccg cggacaagca gaaaaacggc atcaaggcga actttaaaat tcgtcacaac    540

gtggaagacg gtagcgttca actggcggat cactaccagc aaaacacccc gattggcgac    600

ggtccggttc tgctgccgga taaccactat ctgagcaccc agagcgcgct gagcaaggac    660

ccgaacgaaa aacgtgatca catggtgctg ctggagttcg ttaccgcggc gggcatcacc    720

cacggtatgg atgagctcta caaaggtccg gaaaccctgt gcggtgcgga gctggtcgac    780

gcgctgcagt ttgtttgcgg cgatcgtggt ttctacttta acaaaccgac cggctatggt    840

agcagcagcc gtcgtgcgcc gcagaccggt attgtggacg agtgctgctt ccgtagctgc    900

gacctgcgtc gtctggaaat gtactgcgcg ccgctgaaac cggcgaaaag cgcgtaactc    960

gag                                                                  963
```

<210> SEQ ID NO 20
<211> LENGTH: 756
<212> TYPE: DNA
<213> ORGANISM: Artificial Sequence
<220> FEATURE:
<223> OTHER INFORMATION: Synthetic

<400> SEQUENCE: 20

```
catatgtgcc atcatcatca tcatcacggc ggcgctagca agggcgagcg tctgtttacc     60

ggtgtggttc cgattctggt tgagctggac ggcgacgtga acggccacaa gttcagcgtt    120

cgtggtgagg gcgaaggtga tgcgacccgt ggcaagctga ccctgaaatt tatctgcacc    180

accggtaaac tgccggtgcc gtggccgacc ctggttacca ccctgaccta cggtgtgcag    240

tgcttcagcc gttatccgaa gcacatgaaa cgtcacgact tctttaagag cgcgatgccg    300

gagggctacg ttcaagaacg taccattagc ttcaagaaag atggtaccta taagacccgt    360

gcggaagtga aatttgaagg ccgtaccctg gttaaccgta tcgagctgaa gggtcgtgac    420

ttcaaggaaa aaggcaacat tctgggtcac aaactggagt acaactttaa cagccacaac    480

gtgtatatca ccgcggataa gcgtaaaaac ggcatcaagg cgaactttaa aattcgtcac    540

aacgtgaagg acggtagcgt tcagctggcg gatcactacc agcaaaacac cccgattggt    600
```

```
cgtggtccgg tgctgctgcc gcgtaaccac tatctgagca cccgtagcgc gctgagcaaa    660

gacccgaagg aaaaacgtga tcacatggtt ctgctggagt ttgtgaccgc ggcgggcatt    720

acccacggca tggacgaact gtataaataa ctcgag                              756
```

<210> SEQ ID NO 21
<211> LENGTH: 951
<212> TYPE: DNA
<213> ORGANISM: Artificial Sequence
<220> FEATURE:
<223> OTHER INFORMATION: Synthetic

<400> SEQUENCE: 21

```
catcatcatc atcatcatgg cggtgcgagc aagggcgaag aactgtttac cggcgttgtg     60

ccgattctgg ttgaactgga cggcgatgtg aacggccaca agttcagcgt tcgtggtgag    120

ggcgaaggtg atgcgaccaa cggcaagctg accctgaaat ttatctgcac caccggtaaa    180

ctgccggtgc cgtggccgac cctggttacc accctgacct acggtgtgca gtgcttcagc    240

cgttatccgg accacatgaa gcgtcacgat ttctttaaga gcgcgatgcc gaaaggctac    300

gttcaagaac gtaccattag cttcaagaaa gacggcaagt ataaaacccg tgcggaagtg    360

aaatttgaag gccgtaccct ggttaaccgt atcaagctga aaggtcgtga tttcaaggag    420

aaaggcaaca ttctgggtca caagctgcgt tacaacttta acagccacaa agtgtatatc    480

accgcggaca agcagaaaaa cggcatcaag gcgaacttta aaattcgtca caacgtggaa    540

gacggtagcg ttcaactggc ggatcactac cagcaaaaca ccccgattgg cgacggtccg    600

gttctgctgc cggataacca ctatctgagc acccagagcg cgctgagcaa ggacccgaac    660

gaaaaacgtg atcacatggt gctgctggag ttcgttaccg cggcgggcat cacccacggt    720

atggatgagc tctacaaagg tccggaaacc ctgtgcggtg cggagctggt cgacgcgctg    780

cagtttgttt gcggcgatcg tggtttctac tttaacaaac cgaccggcta tggtagcagc    840

agccgtcgtg cgccgcagac cggtattgtg gacgagtgct gcttccgtag ctgcgacctg    900

cgtcgtctgg aaatgtactg cgcgccgctg aaaccggcga aaagcgcgta a             951
```

<210> SEQ ID NO 22
<211> LENGTH: 1011
<212> TYPE: DNA
<213> ORGANISM: Artificial Sequence
<220> FEATURE:
<223> OTHER INFORMATION: Synthetic

<400> SEQUENCE: 22

```
catcatcatc atcatcatgg cggtgcgagc aagggcgaag aactgtttac cggcgttgtg     60

ccgattctgg ttgaactgga cggcgatgtg aacggccaca agttcagcgt tcgtggtgag    120

ggcgaaggtg atgcgaccaa cggcaagctg accctgaaat ttatctgcac caccggtaaa    180

ctgccggtgc cgtggccgac cctggttacc accctgacct acggtgtgca gtgcttcagc    240

cgttatccgg accacatgaa gcgtcacgat ttctttaaga gcgcgatgcc gaaaggctac    300

gttcaagaac gtaccattag cttcaagaaa gacggcaagt ataaaacccg tgcggaagtg    360

aaatttgaag gccgtaccct ggttaaccgt atcaagctga aaggtcgtga tttcaaggag    420

aaaggcaaca ttctgggtca caagctgcgt tacaacttta acagccacaa agtgtatatc    480

accgcggaca agcagaaaaa cggcatcaag gcgaacttta aaattcgtca caacgtggaa    540

gacggtagcg ttcaactggc ggatcactac cagcaaaaca ccccgattgg cgacggtccg    600
```

gttctgctgc cggataacca ctatctgagc acccagagcg cgctgagcaa ggacccgaac 660
gaaaaacgtg atcacatggt gctgctggag ttcgttaccg cggcgggcat cacccacggt 720
atggatgagc tctacaaggg tggcggtggc agcggtggcg gtggcagcgg tggcggtggc 780
agcggtggcg gtggcagcgg gccggagacc ctgtgcggcg cggaactggt cgacgcgctg 840
cagtttgttt gcggcgatcg tggtttctac tttaacaaac cgaccggcta tggtagcagc 900
agccgtcgtg cgccgcagac cggtattgtg gacgagtgct gcttccgtag ctgcgacctg 960
cgtcgtctgg aaatgtactg cgcgccgctg aaaccggcga aaagcgcgta a 1011

<210> SEQ ID NO 23
<211> LENGTH: 995
<212> TYPE: DNA
<213> ORGANISM: Artificial Sequence
<220> FEATURE:
<223> OTHER INFORMATION: Synthetic

<400> SEQUENCE: 23
catcatcatc atcatcatgg cggtgcgagc aagggcgaag aactgtttac cggcgttgtg 60
ccgattctgg ttgaactgga cggcgatgtg aacggccaca agttcagcgt tcgtggtgag 120
ggcgaaggtg atgcgaccaa cggcaagctg accctgaaat ttatctgcac caccggtaaa 180
ctgccggtgc cgtggccgac cctggttacc accctgacct acggtgtgca gtgcttcagc 240
cgttatccgg accacatgaa gcgtcacgat ttctttaaga gcgcgatgcc gaaaggctac 300
gttcaagaac gtaccattag cttcaagaaa gacggcaagt ataaaacccg tgcggaagtg 360
aaatttgaag gccgtaccct ggttaaccgt atcaagctga aaggtcgtga tttcaaggag 420
aaaggcaaca ttctgggtca caagctgcgt tacaacttta acagccacaa agtgtatatc 480
accgcggaca agcagaaaaa cggcatcaag gcgaacttta aaattcgtca caacgtggaa 540
gacggtagcg ttcaactggc ggatcactac cagcaaaaca ccccgattgg cgacggtccg 600
gttctgctgc cggataacca ctatctgagc acccagagcg cgctgagcaa ggacccgaac 660
gaaaaacgtg atcacatggt gctgctggag ttcgttaccg cggcgggcat cacccacggt 720
atggatgagc tctacaaggg tggcggtggc agcggtggcg gtggcagcgg tggcggtggc 780
agcgggccgg agaccctgtg cggcgcggaa ctggtcgacg cgctgcagtt tgtttgcggc 840
gatcgtggtt tctactttaa caaaccgacc ggctatggta gcagcagccg tcgtgcgccg 900
cagaccggta ttgtggacga gtgctgcttc cgtagctgcg acctgcgtcg tctggaaatg 960
tactgcgcgc cgctgaaacc ggcgaaaagc gcgta 995

<210> SEQ ID NO 24
<211> LENGTH: 1032
<212> TYPE: DNA
<213> ORGANISM: Artificial Sequence
<220> FEATURE:
<223> OTHER INFORMATION: Synthetic

<400> SEQUENCE: 24
catcatcatc atcatcatgg cggtgcgagc aagggcgaag aactgtttac cggcgttgtg 60
ccgattctgg ttgaactgga cggcgatgtg aacggccaca agttcagcgt tcgtggtgag 120
ggcgaaggtg atgcgaccaa cggcaagctg accctgaaat ttatctgcac caccggtaaa 180
ctgccggtgc cgtggccgac cctggttacc accctgacct acggtgtgca gtgcttcagc 240
cgttatccgg accacatgaa gcgtcacgat ttctttaaga gcgcgatgcc gaaaggctac 300
gttcaagaac gtaccattag cttcaagaaa gacggcaagt ataaaacccg tgcggaagtg 360

```
aaatttgaag gccgtaccct ggttaaccgt atcaagctga aaggtcgtga tttcaaggag    420

aaaggcaaca ttctgggtca caagctgcgt tacaacttta acagccacaa agtgtatatc    480

accgcggaca agcagaaaaa cggcatcaag gcgaacttta aaattcgtca caacgtggaa    540

gacggtagcg ttcaactggc ggatcactac cagcaaaaca ccccgattgg cgacggtccg    600

gttctgctgc cggataacca ctatctgagc acccagagcg cgctgagcaa ggacccgaac    660

gaaaaacgtg atcacatggt gctgctggag ttcgttaccg cggcgggcat cacccacggt    720

atggatgagc tctacaaggg tggcagcggt ggcagcggtg gcagcggtgg cagcggtggc    780

agcggtggca gcggtggcag cggtggcagc ggtggcagcg ggccggagac cctgtgcggc    840

gcggaactgg tcgacgcgct gcagtttgtt tgcggcgatc gtggtttcta ctttaacaaa    900

ccgaccggct atggtagcag cagccgtcgt gcgccgcaga ccggtattgt ggacgagtgc    960

tgcttccgta gctgcgacct gcgtcgtctg gaaatgtact gcgcgccgct gaaaccggcg   1020

aaaagcgcgt aa                                                       1032
```

<210> SEQ ID NO 25
<211> LENGTH: 996
<212> TYPE: DNA
<213> ORGANISM: Artificial Sequence
<220> FEATURE:
<223> OTHER INFORMATION: Synthetic

<400> SEQUENCE: 25

```
catcatcatc atcatcatgg cggtgcgagc aagggcgaag aactgtttac cggcgttgtg     60

ccgattctgg ttgaactgga cggcgatgtg aacggccaca agttcagcgt tcgtggtgag    120

ggcgaaggtg atgcgaccaa cggcaagctg accctgaaat ttatctgcac caccggtaaa    180

ctgccggtgc cgtggccgac cctggttacc accctgacct acggtgtgca gtgcttcagc    240

cgttatccgg accacatgaa gcgtcacgat ttctttaaga gcgcgatgcc gaaaggctac    300

gttcaagaac gtaccattag cttcaagaaa gacggcaagt ataaaacccg tgcggaagtg    360

aaatttgaag gccgtaccct ggttaaccgt atcaagctga aaggtcgtga tttcaaggag    420

aaaggcaaca ttctgggtca caagctgcgt tacaacttta acagccacaa agtgtatatc    480

accgcggaca agcagaaaaa cggcatcaag gcgaacttta aaattcgtca caacgtggaa    540

gacggtagcg ttcaactggc ggatcactac cagcaaaaca ccccgattgg cgacggtccg    600

gttctgctgc cggataacca ctatctgagc acccagagcg cgctgagcaa ggacccgaac    660

gaaaaacgtg atcacatggt gctgctggag ttcgttaccg cggcgggcat cacccacggt    720

atggatgagc tctacaaaga ggcggcggcg aaagaagcgg cggcgaaaga ggcggcggcg    780

aagggtccgg aaaccctgtg cggcgcggag ctggtcgacg cgctgcagtt tgtttgcggc    840

gatcgtggtt tctactttaa caaaccgacc ggctatggta gcagcagccg tcgtgcgccg    900

cagaccggta ttgtggacga gtgctgcttc cgtagctgcg acctgcgtcg tctggaaatg    960

tactgcgcgc cgctgaaacc ggcgaaaagc gcgtaa                             996
```

<210> SEQ ID NO 26
<211> LENGTH: 1089
<212> TYPE: DNA
<213> ORGANISM: Artificial Sequence
<220> FEATURE:
<223> OTHER INFORMATION: Synthetic

<400> SEQUENCE: 26

```
catcatcatc atcatcatgg cggtgcgagc aagggcgaag aactgtttac cggcgttgtg      60

ccgattctgg ttgaactgga cggcgatgtg aacggccaca agttcagcgt tcgtggtgag     120

ggcgaaggtg atgcgaccaa cggcaagctg accctgaaat ttatctgcac caccggtaaa     180

ctgccggtgc cgtggccgac cctggttacc accctgacct acggtgtgca gtgcttcagc     240

cgttatccgg accacatgaa gcgtcacgat ttctttaaga gcgcgatgcc gaaaggctac     300

gttcaagaac gtaccattag cttcaagaaa gacggcaagt ataaaacccg tgcggaagtg     360

aaatttgaag gccgtaccct ggttaaccgt atcaagctga aaggtcgtga tttcaaggag     420

aaaggcaaca ttctgggtca caagctgcgt tacaacttta acagccacaa agtgtatatc     480

accgcggaca agcagaaaaa cggcatcaag gcgaacttta aaattcgtca caacgtggaa     540

gacggtagcg ttcaactggc ggatcactac cagcaaaaca ccccgattgg cgacggtccg     600

gttctgctgc cggataacca ctatctgagc acccagagcg cgctgagcaa ggacccgaac     660

gaaaaacgtg atcacatggt gctgctggag ttcgttaccg cggcgggcat cacccacggt     720

atggatgagc tctacaaagc ggaggcggct gcgaaggaag cggcggcgaa agaggcggct     780

gctaaggaag cggcggcgaa ggcgctggag gcggaggctg ctgcgaaaga ggcggcggcg     840

aaagaagcgg ctgctaaaga ggcggcggcg aaggcgggtc cggaaaccct gtgcggcgcg     900

gagctggtcg acgcgctgca gtttgtttgc ggcgatcgtg gtttctactt taacaaaccg     960

accggctatg gtagcagcag ccgtcgtgcg ccgcagaccg gtattgtgga cgagtgctgc    1020

ttccgtagct gcgacctgcg tcgtctggaa atgtactgcg cgccgctgaa accggcgaaa    1080

agcgcgtaa                                                            1089


<210> SEQ ID NO 27
<211> LENGTH: 20
<212> TYPE: PRT
<213> ORGANISM: Artificial Sequence
<220> FEATURE:
<223> OTHER INFORMATION: Synthetic

<400> SEQUENCE: 27

Gly Gly Gly Gly Ser Gly Gly Gly Gly Ser Gly Gly Gly Gly Ser Gly
1               5                   10                  15

Gly Gly Gly Ser
            20


<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Gly Gly Gly Gly Ser Gly Gly Gly Gly Ser Gly Gly Gly Gly Ser
1               5                   10                  15


<210> SEQ ID NO 29
<211> LENGTH: 27
<212> TYPE: PRT
<213> ORGANISM: Artificial Sequence
<220> FEATURE:
<223> OTHER INFORMATION: Synthetic

<400> SEQUENCE: 29

Gly Gly Ser Gly Gly Ser Gly Gly Ser Gly Gly Ser Gly Gly Ser Gly
1               5                   10                  15
```

Gly Ser Gly Gly Ser Gly Gly Ser Gly Gly Ser
20 25

<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Glu Ala Ala Ala Lys Glu Ala Ala Ala Lys Glu Ala Ala Ala Lys
1 5 10 15

<210> SEQ ID NO 31
<211> LENGTH: 46
<212> TYPE: PRT
<213> ORGANISM: Artificial Sequence
<220> FEATURE:
<223> OTHER INFORMATION: Synthetic

<400> SEQUENCE: 31

Ala Glu Ala Ala Ala Lys Glu Ala Ala Ala Lys Glu Ala Ala Ala Lys
1 5 10 15

Glu Ala Ala Ala Lys Ala Leu Glu Ala Glu Ala Ala Ala Lys Glu Ala
20 25 30

Ala Ala Lys Glu Ala Ala Ala Lys Glu Ala Ala Ala Lys Ala
35 40 45

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

His His His His His His
1 5

<210> SEQ ID NO 33
<211> LENGTH: 5
<212> TYPE: PRT
<213> ORGANISM: Artificial Sequence
<220> FEATURE:
<223> OTHER INFORMATION: Synthetic

<400> SEQUENCE: 33

Pro Ala Pro Ala Pro
1 5

<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Ala Glu Ala Ala Ala Lys Glu Ala Ala Ala Lys Ala
1 5 10

<210> SEQ ID NO 35
<211> LENGTH: 18
<212> TYPE: PRT

<213> ORGANISM: Artificial Sequence
<220> FEATURE:
<223> OTHER INFORMATION: Synthetic

<400> SEQUENCE: 35

Lys Glu Ser Gly Ser Val Ser Ser Glu Gln Leu Ala Gln Phe Arg Ser
1 5 10 15

Leu Asp

<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Glu Gly Lys Ser Ser Gly Ser Gly Ser Glu Ser Lys Ser Thr
1 5 10

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Gly Gly Gly Gly Gly Gly Gly Gly
1 5

<210> SEQ ID NO 38
<211> LENGTH: 6
<212> TYPE: PRT
<213> ORGANISM: Artificial Sequence
<220> FEATURE:
<223> OTHER INFORMATION: Synthetic

<400> SEQUENCE: 38

Gly Gly Gly Gly Gly Gly
1 5

<210> SEQ ID NO 39
<211> LENGTH: 12
<212> TYPE: PRT
<213> ORGANISM: Artificial Sequence
<220> FEATURE:
<223> OTHER INFORMATION: Synthetic

<400> SEQUENCE: 39

Gly Ser Ala Gly Ser Ala Ala Gly Ser Gly Glu Phe
1 5 10

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Val Ser Gln Thr Ser Lys Leu Thr Arg Ala Glu Thr Val Phe Pro Asp
1 5 10 15

Val

-continued

<210> SEQ ID NO 41
<211> LENGTH: 6
<212> TYPE: PRT
<213> ORGANISM: Artificial Sequence
<220> FEATURE:
<223> OTHER INFORMATION: Synthetic

<400> SEQUENCE: 41

Pro Leu Gly Leu Trp Ala
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Arg Val Leu Ala Glu Ala
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic

<400> SEQUENCE: 43

Glu Asp Val Val Cys Cys Ser Met Ser Tyr
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic

<400> SEQUENCE: 44

Gly Gly Ile Glu Gly Arg Gly Ser
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

Thr Arg His Arg Gln Pro Arg Gly Trp Glu
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic

<400> SEQUENCE: 46

Ala Gly Asn Arg Val Arg Arg Ser Val Gly
1               5                   10

<210> SEQ ID NO 47

-continued

```
<211> LENGTH: 9
<212> TYPE: PRT
<213> ORGANISM: Artificial Sequence
<220> FEATURE:
<223> OTHER INFORMATION: Synthetic

<400> SEQUENCE: 47

Arg Arg Arg Arg Arg Arg Arg Arg Arg
1               5


<210> SEQ ID NO 48
<211> LENGTH: 4
<212> TYPE: PRT
<213> ORGANISM: Artificial Sequence
<220> FEATURE:
<223> OTHER INFORMATION: Synthetic

<400> SEQUENCE: 48

Gly Phe Leu Gly
1


<210> SEQ ID NO 49
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(20)
<223> OTHER INFORMATION: may be absent

<400> SEQUENCE: 49

Gly Gly Gly Gly Ser Gly Gly Gly Gly Ser Gly Gly Gly Gly Ser Gly
1               5                   10                  15

Gly Gly Gly Ser
            20
```